United States Patent
Hicklin et al.

(10) Patent No.: US 10,227,413 B2
(45) Date of Patent: Mar. 12, 2019

(54) ANTI-NEUROPILIN ANTIGEN-BINDING PROTEINS AND METHODS OF USE THEREOF

(71) Applicant: Potenza Therapeutics, Inc., Cambridge, MA (US)

(72) Inventors: Daniel Hicklin, Montclair, NJ (US); Cynthia Seidel-Dugan, Belmont, MA (US); William Winston, Newton, MA (US); Jose-Andres Salmeron-Garcia, Westminster, MA (US); Nels P. Nielson, Lebanon, NH (US); Heather Brodkin, West Newton, MA (US)

(73) Assignee: Potenza Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/900,158

(22) Filed: Feb. 20, 2018

(65) Prior Publication Data

US 2018/0186886 A1    Jul. 5, 2018

Related U.S. Application Data

(63) Continuation of application No. PCT/US2017/067782, filed on Dec. 21, 2017.

(60) Provisional application No. 62/438,733, filed on Dec. 23, 2016.

(51) Int. Cl.
*C07K 16/28* (2006.01)
*A61P 35/00* (2006.01)
*A61K 39/00* (2006.01)

(52) U.S. Cl.
CPC .......... *C07K 16/2863* (2013.01); *A61P 35/00* (2018.01); *C07K 16/2818* (2013.01); *C07K 16/2827* (2013.01); *A61K 2039/505* (2013.01); *A61K 2039/507* (2013.01); *C07K 2317/21* (2013.01); *C07K 2317/30* (2013.01); *C07K 2317/31* (2013.01); *C07K 2317/33* (2013.01); *C07K 2317/34* (2013.01); *C07K 2317/524* (2013.01); *C07K 2317/55* (2013.01); *C07K 2317/565* (2013.01); *C07K 2317/622* (2013.01); *C07K 2317/76* (2013.01); *C07K 2317/92* (2013.01)

(58) Field of Classification Search
CPC ...................... C07K 2317/565; C07K 2317/21
USPC ............................................ 424/133.1, 178.1
See application file for complete search history.

(56) References Cited

FOREIGN PATENT DOCUMENTS

| WO | WO 2007/056470 A2 | 5/2007 |
|---|---|---|
| WO | WO 2008/143666 A2 | 11/2008 |
| WO | WO 2012/006503 A1 | 1/2012 |
| WO | WO 2014/058915 A2 | 4/2014 |

OTHER PUBLICATIONS

Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol (2010) 87:401-410).*
Akagi et al. (British Journal of Cancer (2003) 88, 796-802).*
Liu et al. (Cytokine 32 (2005) 206-212).*
PCT Invitation to Pay Additional Fees, PCT Application No. PCT/US2017/067782, Apr. 9, 2018, 28 pages.
Liang, W.C. et al., "Function Blocking Antibodies to Neuropilin-1 Generated from a Designed Human Synthetic Antibody Phage Library," Journal of Molecular Biology, Feb. 23, 2007, pp. 815-829.
Appleton, B.A. et al., "Structural Studies of Neuropilin/Antibody Complexes Provide Insights into Semaphorin and VEGF Binding," EMBO (European Molecular Biology Organization) Journal, Nov. 28, 2007, pp. 4902-4912, vol. 26, No. 23.
Delgoffe, G.M. et al., "Stability and Function of Regulatory T Cells is Maintained by a Neuropilin-1-Semaphorin-4a Axis," Nature, Aug. 4, 2013, pp. 252-256, vol. 501, No. 7466.
Delgoffe, G.M. et al., "Supplementary Information: Stability and Function of Regulatory T Cells is Maintained by a Neuropilin-1-Semaphorin-4a Axis," Nature, Aug. 4, 2013, pp. 252-256, vol. 501, No. 7466.
Shin, T.H. et al., "Enhancement of the Tumor Penetration of Monoclonal Antibody by the Fusion of a Neuropilin-Targeting Peptide Improves the Antitumor Efficacy," Molecular Cancer Therapeutics, Jan. 16, 2014, pp. 651-661, vol. 13, No. 3.
PCT International Search Report and Written Opinion, PCT Application No. PCT/US2017/067782, Jun. 5, 2018, 31 pages.
Antipenko, A. et al., "Structure of the Semaphorin-3A Receptor Binding Module," Neuron, Cell Press, Aug. 14, 2003, pp. 289-298, vol. 39.
Appleton, B.A. et al., "Structural Studies of Neuropilin/Antibody Complexes Provide Insights Into Semaphorin and VEGF Binding," The EMBO Journal, European Molecular Biology Organization, 2007, pp. 4902-4912, vol. 26.
Bachelder, R.E. et al., "Vascular Endothelial Growth Factor Is an Autocrine Survival Factor for Neuropilin-Expressing Breast Carcinoma Cells," Cancer Research, Aug. 1, 2001, pp. 5736-5740, vol. 61.
Bagci, T. et al., Autocrine Semaphorin 3A Signaling Promotes Glioblastoma Dispersal, Oncogene, 2009, pp. 3537-3550, vol. 28.
Ball, S.G. et al., "Neuropilin-1 Regulates Platelet-Derived Growth Factor Receptor Signalling in Mesenchymal Stem Cells," Biochem. J., 2010, pp. 29-40, vol. 427.
Barr, M. P. et al., "A Peptide Corresponding to the Neuropilin-1-Binding Site on $VEGF_{165}$ Induces Apoptosis of Neuropilin-1-Expressing Brest Tumour Cells," British Journal of Cancer, 2005, pp. 328-333, vol. 92.

(Continued)

*Primary Examiner* — Lynn A Bristol
(74) *Attorney, Agent, or Firm* — Fenwick & West LLP

(57) ABSTRACT

Provided herein are antigen-binding proteins (ABPs) that selectively bind to NRP-1 and its isoforms and homologs, and compositions comprising the ABPs. Also provided are methods of using the ABPs, such as therapeutic and diagnostic methods.

20 Claims, 7 Drawing Sheets

Specification includes a Sequence Listing.

(56) References Cited

OTHER PUBLICATIONS

Barr, M. P. et al., "Vascular Endothelial Growth Factor is an Autocrine Growth Factor, Signaling Through Neuropilin-1 in Non-Small Cell Lung Cancer," Molecular Cancer, 2015, 16 pages, vol. 14, No. 45.
Battaglia, A. et al., "Neuropilin-1 Expression Identifies a Subset of Regulatory T Cells in Human Lymph Nodes That is Modulated by Preoperative Chemoradiation Therapy in Cervical Cancer," Immunology, 2007, pp. 129-138, vol. 123.
Berger, I. et al., "VEGF Receptors on PC12 Cells Mediate Transient Activation of ERKI/2 and Akt: Comparison of Nerve Growth Factor and Vascular Endothelial Growth Factor," Journal of Negative Results in BioMedicine, 2006, pp. 1-6, vol. 5, No. 8.
Bos, P.D. et al., "Transient Regulatory T Cell Ablation Deters Oncogene-Driven Breast Cancer and Enhances Radiotherapy," The Journal of Experimental Medicine, 2013, pp. 2435-2446, vol. 210, No. 11.
Bourbie-Vaudaine, S. et al., "Dendritic Cells Can Turn CD4+ T Lymphocytes Into Vascular Endothelial Growth Factor-Carrying Cells by Inercellular Neuropilin-1 Transfer," The Journal of Immunology, 2006, pp. 1460-1469, vol. 177.
Bouvree, K. et al., "Semaphorin3A, Neuropilin-1, and PlexinA1 Are Required for Lymphatic Valve Formation," Circ. Res., Aug. 3, 2012, pp. 1-20, vol. 111, No. 4.
Bruder, D. et al., "Frontline: Neuropilin-1: A Surface Marker of Regulatory T Cells," European Journal of Immunology, 2004, pp. 623-630, vol. 34.
Bumbaca, D. et al., "Maximizing Tumour Exposure to Anti-Neuropilin-1 Antibody Requires Saturation of Non-Tumour Tissue Antigenic Sinks in Mice," British Journal of Pharmacology, 2012, pp. 368-377, vol. 166.
Cackowski, F.C. et al., "Identification of Two Novel Alternatively Spliced Neuropilin-1 Isoforms," Genomics, Jul. 2004, pp. 82-94, vol. 84, No. 1.
Campos-Mora, M. et al., "Neuropilin-1 in Transplantation Tolerance," Frontiers in Immunology, Nov. 25, 2013, pp. 1-9, vol. 4, Article 405.
Cao, Y. et al., "Neuropilin-1 Mediates Divergent R-Smad Signaling and the Myofibroblast Phenotype," The Journal of Biological Chemistry, Oct. 8, 2010, pp. 31840-31848, vol. 285, No. 41.
Casazza, A. et al. "Impeding Macrophage Entry into Hypoxic Tumor Areas by Sema3A/Nrp1 Signaling Blockade Inhibits Angiogenesis and Restores Antitumor Immunity," Cancer Cell, Dec. 9, 2013, pp. 695-709, vol. 24.
Catalano, "Supplementary Figure Legend," Journal of Immunology, 2010, pp. 1-5.
Catalano, A. et al., "Semaphorin-3A is Expressed by Tumor Cells and Alters T-Cell Signal Transduction and Function," Blood, Apr. 15, 2006, pp. 3321-3329, vol. 107, No. 8.
Chaudhary, B. et al., "Neuropilin 1: Function and Therapeutic Potential in Cancer," Cancer Immunol. Immunother., 2014, pp. 81-99, vol. 63.
Chaudhary, B. et al., "Regulatory T Cells in the Tumor Microenvironment and Cancer Progression: Role and Therapeutic Targeting," Vaccines, 2016, pp. 1-25, vol. 4, No. 28.
Chen, H. et al., "Neuropilin-2, a Novel Member of the Neuropilin Family, Is a High Affinity Receptor for the Semaphorins Sema E and Sema IV but Not Sema III," Neuron, Sep. 1997, pp. 547-559, vol. 19.
Chen, H. et al., "Semaphorin-Neuropilin Interactions Underlying Sympathetic Axon Responses to Class III Semaphorins," Neuron, Dec. 1998, pp. 1283-1290, vol. 21.
Collison, L.W. et al., "In Vitro Treg Suppression Assays," Methods Mol. Biol., 2011, pp. 21-347, vol. 707.
Dai, X. et al., "Ablation of Neuropilin 1 in Myeloid Cells Exacerbates High-Fat Diet-Induced Insulin Resistance Through Nlrp3 Inflammasome In Vivo," Diabetes, Sep. 2017, pp. 2424-2435, Includes Supplementary Data, total of 23 pages, vol. 66.

Dai, X. et al., "Myeloid Cell Neuropilin 1 Ameliorates High-Fat Diet-Induced Insulin Resistance Via Suppression of Nlrp3 Inflammasome," Macrophage, 2017, pp. 1-3, vol. 4, e1594.
Delaire, S. et al., "Biological Activity of Soluble CD100.II. Soluble CD100, Similarly to H-SemaIII, Inhibits Immune Cell Migration," The Journal of Immunology, 2001, pp. 4348-4354, vol. 166.
Delgoffe, G.M. et al., "Regulatory T Cell Stability is Maintained by a Neuropilin-1: Semaphorin-4a Axis," Nature, Sep. 12, 2013, pp. 1-31, vol. 501, No. 7466.
Ellis, L.M., "The Role of Neuropilins in Cancer," Mol. Cancer Ther., May 2006, pp. 1099-1107, vol. 5, No. 5.
Fleissner, D. et al., "Local Induction of Immunosuppressive CD8+ T Cells in the Gut-Associated Lymphoid Tissues," PloSOne, Oct. 2010, pp. 1-8, vol. 5, Issue 10, e15373.
Fuh, G. et al., "Molecular Basis of Cell and Developmental Biology: The Interaction of Neuropilin-1 with Vascular Endothelial Growth Factor and Its Receptor Flt-1," The Journal of Biological Chemistry, 2000, pp. 26690-26695, vol. 275.
Gao, Y.-L. et al., "Tuftsin Prevents the Negative Immunoregulation of Neuropilin-$1^{high}$CD4+CD25+ Regulatory T Cells and Improves Survival Rate in Septic Mice," Oncotarget, 2016, pp. 81791-81805, vol. 7, No. 49.
Gaultier, A. et al., "LDL Receptor-Related Protein 1 Regulates the Abundance of Diverse Cell-Signaling Proteins in the Plasma Membrane Proteome," J. Proteome Res., Dec. 2010, pp. 6689-6695, vol. 9, No. 12.
Gelfand, M.V. et al., "Neuropilin-1 Functions as VEGFR2 Co-Receptor to Guide Developmental Angiogenesis Independent of Ligand Binding," eLife, 2014, pp. 1-18, vol. 3.
Giger, R.J. et al., "Neuropilin-2 Is a Receptor for Semaphorin IV: Insight Into the Structural Basis of Receptor Function and Specificity," Neuron, Nov. 1998, pp. 1079-1092, vol. 21.
Glinka, Y. et al., "Neuropilin-1 is a Receptor for Transforming Growth Factor β-1, Activates Its Latent Form, and Promotes Regulatory T Cell Activity," Journal of Leukocyte Biology, Jul. 2008, pp. 302-310, vol. 84.
Glinka, Y. et al., "Neuroplin-1 Exerts Co-Receptor Function for TGF-Beta-1 on the Membrane of Cancer Cells and Enhances Responses to Both Latent and Active TGF-Beta," Carcinogenesis, 2011, pp. 613-621, vol. 32, No. 4.
Grage-Griebenow, E. et al., "Anti-BDCA-4 (neuropilin-1) Antibody Can Suppress Virus-Induced IFN-Alpha Production of Plasmacytoid Dendritic Cells," Immunology and Cell Biology, 2007, pp. 393-390, vol. 85.
Graziani, G. et al., "Neuropilin-1 as Therapeutic Target for Malignant Melanoma," Frontiers in Oncology, Jun. 2015, pp. 1-9, vol. 5, Article 125.
Gu, C. et al., "Characterization of Neuropilin-1 Structural Features That Confer Binding to Semaphorin 3A and Vascular Endothelial Growth Factor 165," The Journal of Biological Chemistry, May 17, 2002, pp. 18069-18076, vol. 277, No. 20.
Hansen, W. et al., "Neuropilin 1 Deficiency on CD4+Foxp3+ Regulatory T Cell Impairs Mouse Melanoma Growth," The Journal of Experimental Medicine, Oct. 85, 2012, pp. 2001-2016, vol. 209, No. 11.
He, Z. et al., "Neuropilin Is a Receptor for the Axonal Chemorepellant Semaphorin III," Cell, Aug. 22, 1997, pp. 739-751, vol. 90.
Jackson, S.R. et al., "Neuropilin-1 Expression is Induced on Tolerant Self-Reactive CD8+ T Cells But Is Dispensable for the Tolerant Phenotype," PLoS One, Oct. 2014, pp. 1-12, vol. 9, Issue 10, e110707.
Janssen, B.J.C. et al., "Neuropilins Lock Secreted Semaphorins Onto Plexins in a Ternary Signaling Complex," Nat. Strut. Mol. Biol., Dec. 2012, pp. 1293-1299, vol. 19, No. 12.
Jin, Q. et al., "Alternate Receptor Usage of Neuropilin-1 and Glucose Transporter Protein 1 by the Human T Cell Leukemia Virus Type 1," Virology, Jan. 20, 2010, pp. 203-212, vol. 396, No. 2.
Kalekar, L.A. et al., "CD4+ T Cell Anergy Prevents Autoimmunity and Generates Regulatory T Cell Precursors," Nature Immunology, Feb. 1, 2016, pp. 1-12.
Kim, J. et al., "Cutting Edge: Depletion of Foxp3+ Cells Leads to Induction of Autoimmunity by Specific Ablation of Regulatory T

(56) References Cited

OTHER PUBLICATIONS

Cells in Genetically Targeted Mice," The Journal of Immunology, Nov. 18, 2009, pp. 7631-7634, vol. 183.
Knickelbein, J.E. et al., "Cutting Edge: Inhibition of T Cell Activation by TIM-2," The Journal of Immunology, 2006, pp. 4966-4970, vol. 177.
Kofler, N. et al., "The Expanding Role of Neuropilin: Regulation of Vascular TGFβ and PDGF Signaling," Curr. Opin. Hematol., May 2016, pp. 260-267, vol. 23, No. 3.
Kolodkin, A.L. et al., "Neuropilin Is a Semaphorin III Receptor," Cell, Aug. 22, 1997, pp. 753-762, vol. 90.
Kong, J-S. et al., "Anti-Neuropilin-1 Peptide Inhibition of Synoviocyte Survival, Angiogenesis, and Experimental Arthritis," Arthritis & Rheumatism, Jan. 2010, pp. 179-190, vol. 62, No. 1.
Kumanagoh, A. et al., "Immune Semaphorins: A New Area of Semaphorin Research," Journal of Cell Science, 2003, pp. 3463-3470, vol. 116.
Kumanagoh, A. et al., "Nonredundant Roles of Sema4A in the Immune System: Defective T Cell Priming and Th1/Th2 Regulation in Sema4a-Deficient Mice," Immunity, Mar. 2005, pp. 305-316, vol. 22.
Kurtagic, E. et al., "Neutrophil Elastase-Generated Fragment of Vascular Endothelial Growth Factor-A Stimulates Macrophage and Endothelial Progenitor Cell Migration," PLoS One, Dec. 16, 2015, pp. 1-17.
Kwiatkowski, S.C. et al., "Neuropilin-1 Modulates TGFβ Signaling to Drive Glioblastoma Growth and Recurrence After Anti-Angiogenic Therapy," PLoS One, Sep. 22, 2017, pp. 1-19.
Lepelletier, Y. et al., "Immunosuppressive Role of Semaphorin-3A on T Cell Proliferation is Mediated by Inhibition of Actin Cytoskeleton Reorganization," European Journal of Immunology, 2006, pp. 1782-1793, vol. 36.
Li, L. et al., "Neuropilin-1 is Associated with Clinicopathology of Gastric Cancer and Contributes to Cell Proliferation and Migration as Multifunctional Co-Receptors," Journal of Experimental & Clinical Cancer Research, 2016, pp. 1-12, vol. 35, No. 16.
Lowe, P.J. et al., "On Setting the First Dose in Man: Quantitating Biotherapeutic Drug-Target Binding Through Pharmacokinetic and Pharmacodynamic Models," Basic & Clinical Pharmacology & Toxicology, 2009, pp. 195-209, vol. 106.
Lu, Y. et al., "Identification of Circulating Neuropilin-1 and Dose-Dependent Elevation Following Anti-Neuropiling-1 Antibody Administration," mAbs, Jul./Aug. 2009, pp. 364-369, vol. 1, No. 4.
Lynch, J.P. et al., "Plasmacytoid Dendritic Cells Protect from Viral Bronchiolitis and Asthma Through Semaphorin 4a-Mediated T reg Expansion," The Journal of Experimental Medicine, 2018, pp. 1-26.
Mamluk, R. et al., "Molecular Basis of Cell and Developmental Biology: Neuropilin-1 Binds Vascular Endothelial Growth Factor 165, Placenta Growth Factor-2, and Heparin Via Its b1b2 Domain," The Journal of Biological Chemistry, 2002, pp. 24818-24825, vol. 277.
Mendes-Da-Cruz, D.A. et al., "Semaphorins and Neuropilins: New Players in the Neuroendocrine Control of the Intrathymic T-Cell Migration in Humans," Exp. Physiol., 2012, pp. 1146-1150, vol. 97, No. 11.
Miyauchi, J.T. et al., Ablation of Neuropilin 1 From Glioma-Associated Microglia and Macrophages Slows Tumor Progression, Oncotarget, Advance Publications 2016, Jan. 10, 2016, pp. 1-14.
Miyauchi, J.T. et al., "Deletion of Neuropilin 1 from Microglia or Bone Marrow-Derived Macrophages Slows Glioma Progression," American Association for Cancer Research, 2017, pp. 1-28.
Mo, Z. et al., "New Peptide MY1340 Revert the Inhibition Effect of VEGF on Dendritic Cells Differentiation and Maturation Via Blocking VEGF-NRP-1 Axis and Inhibit Tumor Growth in Vivo," International Immunopharmacology, 2018, pp. 132-140, vol. 60.
Morita, S. et al., "A Simulation Study of Methods for Selecting Subgroup-Specific Doses in Phase 1 Trials," Pharm. Stat., Mar. 2017, pp. 143-156, vol. 16, No. 2.
Muhl, L. et al., "Neuropilin 1 Binds PDGH-D and is a Co-Receptor in PDGF-D-PDGFRβ Signaling," Journal of Cell Science, 2017, pp. 1365-1378, vol. 130.
Nakamura, F. et al., "Structural and Functional Relation of Neuropilins," Madame Curie Bioscience Database—NCBI Bookshelf, Nov. 12, 2014, pp. 1-11.
Nakatsuji, Y. et al., "Elevation of Sema4A Implicates Th Cell Skewing and the Efficacy of IFN-β Therapy in Multiple Sclerosis," The Journal of Immunology, Apr. 9, 2012, pp. 1-16.
Narazaki, M. et al., "Ligand-Induced Internalization Selects User of Common Receptor Neuropilin-1 by $VEGF_{165}$ and Semaphorin3A," Blood, May 15, 2006, pp. 3892-3901, vol. 107, No. 10.
Nasarre, P. et al., "The Emerging Role of Class-3 Semaphorins and Their Neuropilin Receptors in Oncology," OncoTargets and Therapy, 2014, pp. 1663-1687, vol. 7.
Nkyimbeng-Takwi, E. et al., "Biology and Function of Neuroimmune Semaphorins 4A and 4D," Immunol. Res., May 2011, pp. 10-21, vol. 50, No. 1.
Ochiumi, T. et al., "Neuropilin-1 is Involved in Regulation of Apoptosis and Migration of Human Colon Cancer," International Journal of Oncology, 2006, pp. 105-116, vol. 29.
O'Quigley, J. et al., "Continual Reassessment Method: A Practical Design for Phase 1 Clinical Trials in Cancer," Biometrics, Mar. 1990, pp. 33-48, vol. 46, No. 1.
Ott, P.A. et al., "Inhibition of Immune Checkpoints and Vascular Endothelial Growth Factor as Combination Therapy for Metastatic Melanoma: An Overview of Rationale, Preclinical Evidence, and Initial Clinical Data," Frontiers in Oncology, Sep. 2015, pp. 1-7, vol. 5, Article 202.
Palodetto, B. et al., "SEMA3A Partially Reverses VEGF Effects Through Binding to Neuropilin-1," Stem Cell Research, 2017, pp. 70-78, vol. 22.
Pan, Q. et al., "Blocking Neuropilin-1 Function Has an Additive Effect with Anti-VEGF to Inhibit Tumor Growth," Cancer Cell, Jan. 2007, pp. 53-67, vol. 11.
Parker, M.W. et al., "Protein Structure and Folding: Structural Basis for Selective Vascular Endothelial Growth Factor-A (VEGF-A) Binding to Neuropilin-1," The Journal of Biological Chemistry, 2012, 11082-11089, vol. 287.
Patnaik, A. et al., "A Phase lb Study Evaluating MNRP1685A, A Fully Human Anti-NRP1 Monoclonal Antibody, in Combination with Bevacizumab and Paclitaxel in Patients with Advanced Solid Tumors," Cancer Chemother. Pharmacol., 2014, pp. 951-960, vol. 73.
Pellet-Many, C. et al., "Neuropilins: Structure, Function and Role in Disease," Biochem. J., 2008, pp. 211-226, vol. 411.
Pellet-Many, C. et al., "Neuropilin-1 Mediates PDGF Stimulation of Vascular Smooth Muscle Cell Migration and Signalling Via $p130^{Cas}$," Biochemical Journal, 2011, pp. 609-618, vol. 435.
Pezoldt, J. et al., "Tissue-Specific Induction of CCR6 and Nrp1 During Early CD4+ T Cell Differentiation," European Journal of Microbiology and Immunology, 2016, pp. 219-226, vol. 6, No. 3.
Pinskey, J.M. et al., "Neuropilin-1 Promotes Hedgehog Signaling Through a Novel Cytoplasmic Motif," JBC Papers in Press, Jun. 30, 2017, pp. 1-26.
Powell, J. et al., "Small Molecule Neuropilin-1 Antagonists Combine Anti-Angiogenic and Anti-Tumour Activity with Immune Modulation Through Reduction of Transforming Growth Factor Beta (TGF#) Production in Regulatory T-Cells," Journal of Medicinal Chemistry, Apr. 12, 2018, pp. 1-96.
Prud'Homme, G.J. et al., "Neuropilins are Multifunctional Coreceptors Involved in Tumor Initiation, Growth, and Metastasis and Immunity," Oncotarget, Sep. 3, 2012, pp. 921-939, vol. 3, No. 9.
Renand, A. et al., "Neuropilin-1 Expression Characterizes T Follicular Helper (Tfh) Cells Activated During B Cell Differentiation in Human Secondary Lymphoid Organs," PLoS One, Dec. 2013, pp. 1-12, vol. 8, Issue 12, e85589.
Rizzolio, S. et al., "Neuropilin-1-Dependent Regulation of EGF-Receptor Signaling," Cancer Research, Sep. 17, 2012, pp. 5801-5811.
Roth, L. et al., "Transmembrane Domain Interactions Control Biological Functions of Neuropilin-1," Molecular Biology of the Cell, Feb. 2008, pp. 646-654, vol. 19.

(56) References Cited

OTHER PUBLICATIONS

Roy, S. et al., "Multifaceted Role of Neuropilins in the Immune System: Potential Targets for Immunotherapy," Frontiers in Immunology, Oct. 10, 2017, pp. 1-27, vol. 8, Article 1228.
Sarris, M. et al., "Neuropilin-1 Expression on Regulatory T Cells Enhances Their Interactions with Dendritic Cells During Antigen Recognition," Immunity, Mar. 2008, pp. 402-413, vol. 28.
Schwamborn, J.C. et al., "Semaphorin 3A Stimulates Neurite Extension and Regulates Gene Expression in PC12 Cells," The Journal of Biological Chemistry, Jul. 23, 2004, pp. 30923-30926, vol. 279, No. 30.
Seerapu, H. et al., "The Cytoplasmic Domain of Neuropilin-1 Regulates Focal Adhesion Turnover," FEBS Letters, Nov. 1, 2013, pp. 1-17, vol. 587, No. 21.
Sharma, A. et al., "Receptor Complexes for Each of the Class 3 Semaphorins," Frontiers in Cellular Neuroscience, Jul. 5, 2012, pp. 1-13, vol. 6, Article 28.
Shimizu, A. et al., "Vascular Endothelial Growth Factor-A Exerts Diverse Cellular Effects Via Small G Proteins, Rho and Rap," International Journal of Molecular Sciences, 2018, pp. 1-15, vol. 19: 1203.
Silva, J-P. et al., "The S228P Mutation Prevents in Vito and in Vitro IgG4 Fab-arm Exchange as Demonstrated Using a Combination of Novel Quantitative Immunoassays and Physiological Matrix Preparation," The Journal of Biological Chemistry, Feb. 27, 2015, pp. 5462-5469, vol. 290, No. 9.
Singh, K. et al., "Concomitant Analysis of Helios and Neuropilin-1 as a Marker to Detect Thymic Derived Regulatory T Cells in Naïve Mice," Scientific Reports, Jan. 14, 2015, pp. 1-10, vol. 5:7767.
Smith, E.P. et al., "Expression of Neuroimmune Semaphorins 4A and 4D and Their Receptors in the Lung is Enhanced by Allergen and Vascular Endothelial Growth Factor," BMC Immunology, 2011, pp. 1-14, vol. 12:30.
Soker, S. et al., "Neuropilin-1 Is Expressed by Endothelial and Tumor Cells as an Isoform-Specific Receptor for Vascular Endothelial Growth Factor," Cell, Mar. 20, 1998, pp. 735-745, vol. 92.
Solomon, B.D. et al., "Neuropilin-1 Attenuates Autoreactivity in Experimental Autoimmune Encephalomyelitis," PNAS, Feb. 1, 2011, pp. 2040-2045, vol. 108, No. 5.
Takamatsu, H. et al., "Regulation of Immune Cell Responses by Semaphorins and Their Receptors," Cellular & Molecular Immunology, 2010, pp. 83-88, vol. 7.
Teng, Y. et al., "Adenovirus-Mediated Delivery of Sema3A Alleviates Rheumatoid Arthritis in a Serum-Transfer Induced Mouse Model," Oncotarget, 2017, pp. 66270-66280, vol. 8, No. 39.
Teng, M.W.L. et al., "Conditional Regulatory T-Cell Depletion Releases Adaptive Immunity Preventing Carcinogenesis and Suppressing Established Tumor Growth," Cancer Research, Oct. 5, 2010, pp. 7800-7809, vol. 70.
Teran, M. et al., "Synergistic Binding of Vascular Endothelial Growth Factor-A and Its Receptors to Heparin Selectively Modulates Complex Affinity," JBC Papers in Press, May 15, 2015, pp. 1-29.
Tordjman, R. et al., "A Neuronal Receptor, Neuropilin-1, Is Essential for the Initiation of the Primary Immune Response," Nature Immunology, May 2002, pp. 477-482, vol. 3, No. 5.
Tse, B.W.C. et al., "Neuropilin-1 is Upregulated in the Adaptive Response of Prostate Tumors to Androgen-Targeted Therapies and is Prognostic of Metastatic Progression and Patient Mortality," Oncogene, 2017, pp. 1-11.
Valdasz, Z. et al., "The Involvement of Immune Semaphorins in the Pathogenesis of Inflammatory Bowel Diseases (IBDs)," PLoS One, May 15, 2015, pp. 1-12.
Vander Kooi, C.W. et al., "Structural Basis for Ligand and Heparin Binding to Neuropilin B Domains," PNAS, Apr. 10, 2007, pp. 6152-6157, vol. 104, No. 15.

Van Der Zwaag, B. et al., "Plexin-D1, A Novel Plexin Family Member, Is Expressed in Vascular Endothelium and the Central Nervous System During Mouse Embryogenesis," Developmental Dynamics, 2002, pp. 336-343, vol. 225.
Vincent, P. et al., "A Role for the Neuronal Protein Collapsin Response Mediator Protein 2 in T Lymphocyte Polarization and Migration," The Journal of Immunology, 2005, pp. 7650-7660, vol. 175.
Vivekanandhan, S. et al., "Genetic Status of KRAS Modulates the Role of Neuropilin-1 in Tumorigenesis," Scientific Reports, 2017, pp. 1-11, vol. 7:12877.
Voron, T. et al., "VEGF-A Modulates Expression of Inhibitory Checkpoints on CD8+ T Cells in Tumors," J. Exp. Med., 2015, pp. 139-148, vol. 212. No. 2.
Wang, S. et al., "Interleukin-10 Deficiency Impairs Regulatory T Cell-Derived Neuropilin-1 Functions and Promotes Th1 and Th17 Immunity," Scientific Reports, 2016, pp. 1-16, vol. 6: 24249.
Weiss, J.M. et al., "Neuropilin 1 is Expressed on Thymus-Derived Natural Regulatory T Cells, but not Mucosa-Generated Induced Foxp3+ T Reg Cells," J. Exp. Med., Sep. 10, 2012, pp. 1723-1742, vol. 209, No. 10.
Williams, J.B. et al., "The EGR2 Targets LAG-3 and 4-1BB Describe and Regulate Dysfunctional Antigen-Specific CD8+ T Cells in the Tumor Microenvironment," J. Exp. Med., 2017, pp. 381-400, vol. 214, No. 2.
Wnuk, M. et al., "Neuropilin 1 Regulates Glomerular Function and Basement Membrane Composition Through Pericytes in the Mouse Kidney," Kidney International, 2016, pp. 1-12.
Xin, Y. et al., "Pharmacokinetic and Pharmacodynamic Analysis of Circulating Biomarkers of Anti-NRP1, a Novel Antiangiogenesis Agent, in Two Phase I Trials in Patients with Advanced Solid Tumors," Clinical Cancer Research, Nov. 1, 2012, pp. 6040-6048, vol. 18, No. 21.
Yadav, M. et al., Neuropilin-1 Distinguishes Natural and Inducible Regulatory T Cells Among Regulatory T Cell Subsets in Vivo, Sep. 10, 2012, pp. 1713-1722, vol. 209, No. 10.
Yamamoto, M. et al., "Plexin-A4 Negatively Regulates T Lymphocyte Responses," International Immunology, 2008, pp. 413-420, vol. 20, No. 3.
Yang, S. et al., "Circulating Soluble Neuropilin-1 in Patients with Early Cervical Cancer and Cervical Intraepithelial Neoplasia Can Be Used as a Valuable Diagnostic Biomarker," Hindawi Publishing Corporation, Disease Markers, 2015, vol. 2015, Article ID 506428.
Yu, D.C.W. et al., "Butyrate Suppresses Expression of Neuropilin 1 in Colorectal Cell Lines Through Inhibition of Sp1 Transactivation," Molecular Cancer, pp. 1-13, vol. 9:276.
Yuan, Q. et al., "CD4+CD25-Nrp1+ T Cells Synergize with Rapamycin to Prevent Murine Cardiac Allorejection in Immunocompetent Recipients," PLoS One, Apr. 2013, pp. 1-8, vol. 8, Issue 4, e61151.
Yukawa, K. et al., Sema4A Induces Cell Morphological Changes Through B-Type Plexin-Mediated Signaling, International Journal of Molecular Medicine, 2010, pp. 225-230, vol. 25.
Zhang, L. et al., "Combination of NRP1-Mediated iRGD with 5-Fluorouracil Suppresses Proliferation, Migration and Invasion of Gastric Cancer Cells," Biomedicine & Pharmacotherapy, 2017, pp. 1136-1143, vol. 93.
Zhou, R. et al., "A Novel Association of Neuropilin-1 and MUC1 in Pancreatic Ductal Adenocarcinoma: Role in Induction of VEGF Signaling and Angiogenesis," Oncogene, Oct. 27, 2016, pp. 5608-5618, vol. 35, No. 43.
Ziogas, A.C. et al., "VEGF Directly Suppresses Activation of T Cells from Ovarian Cancer Patients and Healthy Individuals Via VEGF Receptor Type 2," International Journal of Cancer, 2012, pp. 857-864, vol. 130.

* cited by examiner

US 10,227,413 B2

ANTI-NEUROPILIN ANTIGEN-BINDING PROTEINS AND METHODS OF USE THEREOF

SEQUENCE LISTING

The instant application contains a Sequence Listing which has been submitted electronically in ASCII format and is hereby incorporated by reference in its entirety. Said ASCII copy, created on Jan. 11, 2018, is named 39503US_CRF_sequencelisting.txt and is 192,455 bytes in size.

FIELD

Provided herein are antigen-binding proteins (ABPs) with binding specificity for NRP-1 and compositions comprising such ABPs, including pharmaceutical compositions, diagnostic compositions, and kits. Also provided are methods of making NRP-1 ABPs, and methods of using NRP-1 ABPs, for example, for therapeutic purposes, diagnostic purposes, and research purposes.

BACKGROUND

Multiple studies have demonstrated that tumors are able to establish an immunosuppressive microenvironment to escape immune surveillance and promote tumor development. Regulatory T cells (Tregs) are an important component of the immunosuppressive milieu in the tumor environment and work by dampening T cell immunity to tumor associated antigens. Tregs are therefore a major obstacle in mounting an effective anti-tumor immune response. Depletion of Tregs in murine models of cancer inhibits tumor growth; however, the accompanying autoimmune and inflammatory disorders associated with a complete depletion of Tregs may limit the clinical utility of this approach. Strategies which specifically target Tregs, in the inflammatory tumor microenvironment, may be a viable alternative. Recent studies in several laboratories have identified Neuropilin 1 (NRP-1) as a candidate target for modulating Treg activity in tumors without impacting Tregs in the periphery (see, e.g., Chaudhary and Elkord, Vaccines (2016) September; 4(3): 28; Bos et al., *J Exp Med* (2013) 210 (11):2435-66; Teng et al., *Cancer Res.* (2010) 70 (20):7800-.

NRP-1 is a multifunctional 130-kDa transmembrane protein with a large extracellular domain containing two N-terminal CUB domains (a1 and a2), two coagulation factor V/VIII homology domains (b1 and b2) and a single MAM domain (c). The cytoplasmic tail is short and does not display any catalytic activity on its own. NRP-1 is a receptor with multiple known ligands and co-receptors, including semaphorins, VEGF, P1GF and plexins, among others (Appleton et al., *Embo J.* (2007) November 28; 26(23): 4902-4912).

NRP-1 is expressed on human and murine Tregs, and this expression identifies a highly-suppressive Treg subset. Within the tumor microenvironment, NRP-1 expression is required for Treg stability and function but does not impact Tregs outside the inflammatory environment of tumors. Recent studies have identified the immune cell-expressed ligand semaphorin 4A (Sema4a) as an additional ligand for NRP-1, and demonstrated that the sema4a/NRP-1 interaction is an important mediator of Treg stability in vitro and in inflammatory sites in vivo. These data suggest that NRP-1 is required for Treg lineage stability and function (see, e.g., Delgoffe et al., Nature (2013) September 12; 501(7466): 252-6.).

Several lines of evidence support the utility of targeting the interaction of NRP-1 and its associated proteins, in particular targeting the NRP-1/Sema axis, on Tregs as a strategy for modulating the immunosuppressive microenvironment found in tumors. For instance, mice with Treg targeted NRP-1 knock-out exhibit reduced tumor growth in several murine tumor models, without any other autoimmune phenotypes. Additionally, antagonists to NRP-1 or Sema reverse Treg suppressive activity and demonstrate anti-tumor efficacy again in the absence of autoimmune adverse events. Furthermore, the NRP-1-VEGFA axis has been proposed as an important pathway regulating the chemotaxis of Tregs into the tumor micro-environment, and an antagonistic Ab that blocks this interaction on Tregs could inhibit the influx of these suppressive cells into the tumor.

There is emerging evidence suggesting the NRP-1 is expressed on the surface of immune cells in human tumors. NRP-1+Tregs are found in the draining lymph nodes (DLN) from cervical cancer patents, and there was a significant drop in the percentage of Tregs in DLN in patients with a pathological response to preoperative chemoradiation. In addition, NRP-1+Tregs have been observed in tumor infiltrating lymphocytes (TILs) in patients with melanoma and head and neck squamous cell carcinoma.

Thus, there is a need for therapeutics that can antagonize NRP-1 without inducing autoimmune disease. Provided herein are ABPs that fulfill this need.

SUMMARY

Provided herein are ABPs that specifically bind NRP-1 and methods of using such ABPs.

In one aspect, provided herein are is an isolated multivalent antigen binding protein (ABP) that specifically binds human NRP-1 (hNRP-1; SEQ ID NO:130), wherein the ABP comprises the following six CDR sequences:

(a) a CDR-H3 having the sequence set forth in SEQ ID NO:47;
(b) a CDR-H2 having the sequence $X_1$ISGSGGX$_2$TYYADSVX$_3$G, wherein $X_1$ is I or A, $X_2$ is S or A, and $X_3$ is K or E, as set forth in SEQ ID NO:136;
(c) a CDR-H1 having the sequence FTFX$_1$SX$_2$AMV, wherein $X_1$ is A, K, or S and $X_2$ is Y or V, as set forth in SEQ ID NO:137;
(d) a CDR-L3 having the sequence set forth in SEQ ID NO:81;
(e) a CDR-L2 having the sequence set forth in SEQ ID NO:71; and
(f) a CDR-L1 having the sequence set forth in SEQ ID NO:63.

In one embodiment, the ABP comprises a CDR-H3 of SEQ ID NO:47, a CDR-H2 of SEQ ID NO:27, a CDR-H1 of SEQ ID NO:12, a CDR-L3 of SEQ ID NO:81, a CDR-L2 of SEQ ID NO:71, and a CDR-L1 of SEQ ID NO:63; or a CDR-H3 of SEQ ID NO:47, a CDR-H2 of SEQ ID NO:28, a CDR-H1 of SEQ ID NO:13, a CDR-L3 of SEQ ID NO:81, a CDR-L2 of SEQ ID NO:71, and a CDR-L1 of SEQ ID NO:63; or a CDR-H3 of SEQ ID NO:47, a CDR-H2 of SEQ ID NO:29, a CDR-H1 of SEQ ID NO:14, a CDR-L3 of SEQ ID NO:81, a CDR-L2 of SEQ ID NO:71, and a CDR-L1 of SEQ ID NO:63; or a CDR-H3 of SEQ ID NO:47, a CDR-H2 of SEQ ID NO:30, a CDR-H1 of SEQ ID NO:14, a CDR-L3 of SEQ ID NO:81, a CDR-L2 of SEQ ID NO:71, and a CDR-L1 of SEQ ID NO:63.

In another embodiment, the ABP comprises a $V_H$ sequence of SEQ ID NO:92 and a $V_L$ sequence of SEQ ID NO:104; a $V_H$ sequence of SEQ ID NO:93 and a $V_L$ sequence of SEQ ID NO:104; a $V_H$ sequence of SEQ ID NO:94 and a $V_L$ sequence of SEQ ID NO:104; a $V_H$ sequence of SEQ ID NO:95 and a $V_L$ sequence of SEQ ID NO:104; or a $V_H$ sequence of SEQ ID NO:96 and a $V_L$ sequence of SEQ ID NO:104.

In another embodiment, the ABP comprises a heavy chain of SEQ ID NO:114 and a light chain of SEQ ID NO:126; a heavy chain of SEQ ID NO:115 and a light chain of SEQ ID NO:126; a heavy chain of SEQ ID NO:116 and a light chain of SEQ ID NO:126; a heavy chain of SEQ ID NO:117 and a light chain of SEQ ID NO:126; or a heavy chain of SEQ ID NO:118 and a light chain of SEQ ID NO:126.

In another aspect is provided an isolated multivalent antigen binding protein (ABP) that specifically binds human NRP-1 (hNRP-1; SEQ ID NO:130), wherein the ABP comprises the following six CDR sequences:
(a) a CDR-H3 having the sequence set forth in SEQ ID NO:41;
(b) a CDR-H2 having the sequence set forth in SEQ ID NO:23;
(c) a CDR-H1 having the sequence set forth in SEQ ID NO:8;
(d) a CDR-L3 having the sequence set forth in SEQ ID NO:77;
(e) a CDR-L2 having the sequence set forth in SEQ ID NO:67, and
(f) a CDR-L1 having the sequence set forth in SEQ ID NO:59.

In one embodiment, the ABP comprises a $V_H$ sequence of SEQ ID NO:85 and a $V_L$ sequence of SEQ ID NO:100; or a $V_H$ sequence of SEQ ID NO:86 and a $V_L$ sequence of SEQ ID NO:100. In another embodiment, the ABP comprises a heavy chain of SEQ ID NO:107 and a kappa light chain of SEQ ID NO:122; and a heavy chain of SEQ ID NO:108 and a kappa light chain of SEQ ID NO:122.

In another aspect is provided an isolated multivalent antigen binding protein (ABP) that specifically binds human NRP-1 (hNRP-1; SEQ ID NO:130), wherein the ABP comprises the following six CDR sequences:
(a) a CDR-H3 having the sequence ARDLGYYGS-GMHX, wherein X is A or V, as set forth in SEQ ID NO:138;
(a) a CDR-H2 having the sequence set forth in SEQ ID NO:24;
(b) a CDR-H1 having the sequence set forth in SEQ ID NO:9;
(c) a CDR-L3 having the sequence set forth in SEQ ID NO:78;
(d) a CDR-L2 having the sequence set forth in SEQ ID NO:68; and
(e) a CDR-L1 having the sequence set forth in SEQ ID NO:60.

In one embodiment, the ABP comprises: a CDR-H3 of SEQ ID NO:42, a CDR-H2 of SEQ ID NO:24, a CDR-H1 of SEQ ID NO:9, a CDR-L3 of SEQ ID NO:78, a CDR-L2 of SEQ ID NO:68, and a CDR-L1 of SEQ ID NO:60; or a CDR-H3 of SEQ ID NO:43, a CDR-H2 of SEQ ID NO:24, a CDR-H1 of SEQ ID NO:9, a CDR-L3 of SEQ ID NO:78, a CDR-L2 of SEQ ID NO:68, and a CDR-L1 of SEQ ID NO:60. In another embodiment, the ABP comprises a $V_H$ sequence of SEQ ID NO:87 and a $V_L$ sequence of SEQ ID NO:101; or the ABP comprises a $V_H$ sequence of SEQ ID NO:88 and a $V_L$ sequence of SEQ ID NO:101. In another embodiment, the ABP comprises a heavy chain of SEQ ID NO:109 and a kappa light chain of SEQ ID NO:123; or the ABP comprises a heavy chain of SEQ ID NO:110 and a kappa light chain of SEQ ID NO:123.

In another aspect is provided an isolated multivalent antigen binding protein (ABP) that specifically binds human NRP-1 (hNRP-1; SEQ ID NO:130), wherein the ABP comprises the following six CDR sequences:
(a) a CDR-H3 having the sequence, ARDRGMYYAS-GFXP, wherein X is G or N, as set forth in (SEQ ID NO:139);
(b) a CDR-H2 having the sequence set forth in SEQ ID NO:25;
(c) a CDR-H1 having the sequence set forth in SEQ ID NO:10;
(d) a CDR-L3 having the sequence set forth in SEQ ID NO:79;
(e) a CDR-L2 having the sequence set forth in SEQ ID NO:69; and
(f) a CDR-L1 having the sequence set forth in SEQ ID NO:61.

In one embodiment the ABP comprises a CDR-H3 of SEQ ID NO:44, a CDR-H2 of SEQ ID NO:25, a CDR-H1 of SEQ ID NO:10, a CDR-L3 of SEQ ID NO:79, a CDR-L2 of SEQ ID NO:69, and a CDR-L1 of SEQ ID NO:61; or a CDR-H3 of SEQ ID NO:45, a CDR-H2 of SEQ ID NO:25, a CDR-H1 of SEQ ID NO:10, a CDR-L3 of SEQ ID NO:79, a CDR-L2 of SEQ ID NO:69, and a CDR-L1 of SEQ ID NO:61. In another embodiment, the ABP comprises a $V_H$ sequence of SEQ ID NO:89 and a $V_L$ sequence of SEQ ID NO:102; or a $V_H$ sequence of SEQ ID NO:90 and a $V_L$ sequence of SEQ ID NO:102. In another embodiment, the ABP comprises a heavy chain of SEQ ID NO:111 and a kappa light chain of SEQ ID NO:124; or the ABP comprises a heavy chain of SEQ ID NO:112 and a kappa light chain of SEQ ID NO:124.

In another aspect is provided an isolated multivalent antigen binding protein (ABP) that specifically binds human NRP-1 (hNRP-1; SEQ ID NO:130), comprising the following six CDR sequences:
(a) a CDR-H3 having the sequence set forth in SEQ ID NO:46;
(b) a CDR-H2 having the sequence set forth in SEQ ID NO:26;
(c) a CDR-H1 having the sequence set forth in SEQ ID NO:11;
(d) a CDR-L3 having the sequence set forth in SEQ ID NO:80;
(e) a CDR-L2 having the sequence set forth in SEQ ID NO:70; and
(f) a CDR-L1 having the sequence set forth in SEQ ID NO:62.

In one embodiment, the ABP comprises a $V_H$ sequence of SEQ ID NO:91 and a $V_L$ sequence of SEQ ID NO:103. In another embodiment, the ABP comprises a heavy chain of SEQ ID NO:113 and a kappa light chain of SEQ ID NO:125.

In another aspect is provided an isolated multivalent antigen binding protein (ABP) that specifically binds human NRP-1 (hNRP-1; SEQ ID NO:130), comprising the following six CDR sequences:
(a) a CDR-H3 having the sequence set forth in SEQ ID NO:48;
(b) a CDR-H2 having the sequence set forth in SEQ ID NO:31;
(c) a CDR-H1 having the sequence set forth in SEQ ID NO:15;
(d) a CDR-L3 having the sequence set forth in SEQ ID NO:82;

(e) a CDR-L2 having the sequence set forth in SEQ ID NO:68; and (f) a CDR-L1 having the sequence set forth in SEQ ID NO:64.

In one embodiment, the ABP comprises a $V_H$ sequence of SEQ ID NO:97 and a $V_L$ sequence of SEQ ID NO:105, or a $V_H$ sequence of SEQ ID NO:98 and a $V_L$ sequence of SEQ ID NO:105. In another embodiment, the ABP comprises: a heavy chain of SEQ ID NO:119 and a kappa light chain of SEQ ID NO:127; or a heavy chain of SEQ ID NO:120 and a kappa light chain of SEQ ID NO:127.

In another aspect is provided an isolated multivalent antigen binding protein (ABP) that specifically binds human NRP-1 (hNRP-1; SEQ ID NO:130), comprising the following six CDR sequences:

(a) a CDR-H3 having the sequence set forth in SEQ ID NO:49;

(b) a CDR-H2 having the sequence set forth in SEQ ID NO:32;

(c) a CDR-H1 having the sequence set forth in SEQ ID NO:16;

(d) a CDR-L3 having the sequence set forth in SEQ ID NO:83;

(e) a CDR-L2 having the sequence set forth in SEQ ID NO:72; and (f) a CDR-L1 having the sequence set forth in SEQ ID NO:65.

In one embodiment, the ABP comprises a $V_H$ sequence of SEQ ID NO:99 and a $V_L$ sequence of SEQ ID NO:106. In another embodiment, the ABP comprises a heavy chain of SEQ ID NO:121 and a kappa light chain of SEQ ID NO:128.

In another aspect is provided an isolated antigen binding protein (ABP) that specifically binds human NRP-1 (hNRP-1; SEQ ID NO:130), comprising a CDR-H3 having at least about 80% identity to a CDR-H3 of a $V_H$ region selected from SEQ ID NOs:41-49; a CDR-H2 having at least about 80% identity to a CDR-H2 of a $V_H$ region selected from SEQ ID NOs:23-32; a CDR-H1 having at least about 80% identity to a CDR-H1 of a $V_H$ region selected from SEQ ID NOs:8-16; a CDR-L3 having at least about 80% identity to a CDR-L3 of a $V_L$ region selected from SEQ ID NOs:77-83; a CDR-L2 having at least about 80% identity to a CDR-L2 of a $V_L$ region selected from SEQ ID NOs:67-72; and a CDR-L1 having at least about 80% identity to a CDR-L1 of a $V_L$ region selected from SEQ ID NOs:59-65. In one embodiment, the CDR-H3, CDR-H2, CDR-H1, CDR-L3, CDR-L2, and CDR-L1 are each identified according to a numbering scheme selected from the Kabat numbering scheme, the Chothia numbering scheme, or the IMGT numbering scheme. In another embodiment, the CDR-H1 is identified as defined by both the Chothia and Kabat numbering schemes, inclusive of the boundaries of both numbering schemes. In one embodiment, the CDR-H3 comprises a CDR-H3 selected from SEQ ID NOs:41-49, or a variant thereof having 1, 2, or 3 amino acid substitutions; the CDR-H2 comprises a CDR-H3 selected from SEQ ID NOs:23-32, or a variant thereof having 1, 2, or 3 amino acid substitutions; the CDR-H1 comprises a CDR-H1 selected from SEQ ID NOs:8-16, or a variant thereof having 1 or 2 amino acid substitutions; the CDR-L3 comprises a CDR-L3 selected from SEQ ID NOs:77-83, or a variant thereof having 1 or 2 amino acid substitutions; the CDR-L2 comprises a CDR-L2 selected from SEQ ID NOs:67-72, or a variant thereof having 1 amino acid substitution; and the CDR-L1 comprises a CDR-L1 selected from SEQ ID NOs: 59-65, or a variant thereof having 1 or 2 amino acid substitutions. In one embodiment, the amino acid substitutions are conservative amino acid substitutions.

In another aspect is provided an ABP that specifically binds human NRP-1, wherein the ABP:

(a) competes or cross-competes for binding to NRP-1 with an antibody selected from MAB1, MAB2, MAB3, MAB4, MAB5, MAB6, MAB7, MAB8, MAB9, MAB10, MAB11, MAB12, MAB13, MAB14, or MAB15, each as provided in Appendix A of this disclosure;

(b) is specific for cell surface NRP-1;

(c) specifically blocks NRP-1 binding to a transmembrane semaphorin polypeptide;

(d) blocks the interaction between a NRP-1 polypeptide and a vascular endothelial cell growth factor (VEGF) polypeptide;

(e) is capable of inhibiting Treg suppression in a human subject;

(f) co-stimulates an effector T cell in combination with antigen presentation from an antigen-presenting cell;

(g) inhibits the suppression of an effector T cell by a regulatory T cell;

(h) reduces the number of effector T cells in a tissue or in systemic circulation;

(i) does not substantially bind platelets;

(j) does not substantially cause thrombocytopenia when administered to a patient;

(k) blocks SEMA3 binding to NRP-1;

(l) does not bind to NRP-1-negative cells; or (m) is capable of any combination of (a)-(l).

In one embodiment, the ABP antibody does not compete or cross-compete for binding with an antibody selected from MAB1, MAB2, MAB3, MAB4, MAB5, MAB6, MAB7, MAB8, MAB9, MAB10, MAB11, MAB12, MAB13, MAB14, or MAB15, each as provided in Appendix A of this disclosure. In one embodiment, the ABP is an ABP selected from MAB1, MAB2, MAB3, MAB4, MAB5, MAB6, MAB7, MAB8, MAB9, MAB10, MAB11, MAB12, MAB13, MAB14, or MAB15, each as provided in Appendix A of this disclosure. In one embodiment, the NRP-1 is selected from hNRP-1 (SEQ ID NO:130), cNRP-1 (SEQ ID NO:132), mNRP-1 (SEQ ID NO:134), rNRP-1 (SEQ ID NO:135), and combinations thereof.

In one embodiment, the ABP comprises an antibody. In one embodiment, the antibody is a monoclonal antibody. In another embodiment, the antibody is selected from a human antibody, a humanized antibody or a chimeric antibody. In one embodiment, the ABP is multivalent. In another embodiment, the ABP comprises an antibody fragment. In another embodiment, the ABP comprises an alternative scaffold. In another embodiment, the ABP comprises an immunoglobulin constant region. In another embodiment, the ABP comprises heavy chain constant region of a class selected from IgA, IgD, IgE, IgG, or IgM. In another embodiment, ABP comprises a heavy chain constant region of the class IgG and a subclass selected from IgG4, IgG1, IgG2, or IgG3. In another embodiment, the IgG is an IgG4. In another embodiment, the IgG is an IgG1.

In one embodiment, the ABP comprises a common light chain antibody, an antibody with a knobs-into-holes modification, an scFv attached to an IgG, a Fab attached to an IgG, a diabodyi, a tetravalent bispecific antibody, a DVD-IgMAB, a DARTT M, a DuoBody®, a CovX-Body, an Fcab antibody, a TandAb®, a tandem Fab, a Zybody$^{MAB}$, or combinations thereof.

In one embodiment, the ABP blocks binding of semaphorin 3A (SEMA3A) to NRP-1 by at least about 10%, at least about 20%, at least about 30%, at least about 40%, at least about 50%, at least about 60%, at least about 70%, at least about 80%, or at least about 90%. In one embodiment, the ABP reduces binding of semaphorin 3A to NRP-1 by at least about 50%. In one embodiment, the tissue is a tumor. In another embodiment, the NRP-1 is expressed on the surface of a target cell.

In one embodiment, the ABP comprises a polypeptide sequence having a pyroglutamate (pE) residue at its N-terminus. In another embodiment, the ABP comprises a $V_H$ sequence in which an N-terminal Q is substituted with pE. In another embodiment, the ABP comprises a $V_H$ sequence in which an N-terminal E is substituted with pE. In another embodiment, the ABP comprises a $V_L$ sequence in which an N-terminal E is substituted with pE. In another embodiment, the ABP comprises a heavy chain sequence in which an N-terminal Q is substituted with pE. In another embodiment, the ABP comprises a heavy chain sequence in which an N-terminal E is substituted with pE. In another embodiment, the ABP comprises a light chain sequence in which an N-terminal E is substituted with pE.

In one embodiment, the ABP specifically binds to human NRP-1 with a kD of less than 20 nM, less than 10 nM, less than 5 nM, less than 2 nM, less than 1 nM, less than 0.5 nM, or less than 0.2 nM. In another embodiment, the ABP specifically binds to NRP-1 from humans, mice, and cynomolgus monkeys. In one embodiment, the ABP binds to a different epitope on NRP-1 than the epitope on NRP-1 to which SEC10 binds. In one embodiment, the ABP binds to the a1, a2, b1, or b2 domain of NRP-1. In another embodiment, the ABP binds to more than one domain of NRP-1. In another embodiment, the ABP binds to the b2 domain of NRP-1. In another embodiment, the ABP binds to the b1 domain of NRP-1.

In another aspect is provided any of the ABPs disclosed herein for use as a medicament. In another embodiment, the ABP is provided for use in the treatment of a cancer or viral infection. In one embodiment, the cancer is selected from a solid tumor and a hematological tumor.

In another aspect is provided a kit comprising any of the ABPs disclosed herein, and instructions for use of the ABP. In one embodiment, the kit comprises a lyophilized ABP. In another embodiment, the kit comprises a fluid for reconstitution of the lyophilized ABP.

In another aspect is provided an isolated polynucleotide encoding an ABP disclosed herein, a $V_H$ thereof, a $V_L$ thereof, a light chain thereof, a heavy chain thereof or an antigen-binding portion thereof.

In another aspect is provided a vector comprising the isolated polynucleotide encoding an ABP disclosed herein, a $V_H$ thereof, a $V_L$ thereof, a light chain thereof, a heavy chain thereof or an antigen-binding portion thereof.

In another aspect is provided a host cell comprising any of the vectors or polynucleotides disclosed herein. In one embodiment, the host cell is selected from a bacterial cell, a fungal cell, and a mammalian cell. In another embodiment, the host cell is selected from an *E. coli* cell, a *Saccharomyces cerevisiae* cell, and a CHO cell.

In another aspect is provided a cell-free expression reaction comprising any of the vectors or polynucleotides disclosed herein.

In another aspect is provided a method of producing an ABP as disclosed herein, comprising expressing the ABP in the host cell disclosed herein and isolating the expressed ABP.

In another aspect is provided a pharmaceutical composition comprising any of the ABPs disclosed herein and a pharmaceutically acceptable excipient. In one embodiment, the ABP is present in the composition in an amount effective to locally inhibit the NRP-1:semaphorin-4 interaction in a tumor. In one embodiment, the anti-NRP-1 antibody is present in the composition in an amount effective to inhibit an interaction between NRP-1 and a transmembrane semaphorin polypeptide when administered to a human subject. In another embodiment, the anti-NRP-1 antibody specifically blocks NRP-1 binding to a transmembrane semaphorin polypeptide. In another embodiment, the anti-NRP-1 antibody blocks the interaction between a NRP-1 polypeptide and a vascular endothelial cell growth factor (VEGF) polypeptide. In another embodiment, the anti-NRP-1 antibody blocks binding of a semaphorin polypeptide. In one embodiment, the anti-NRP1 antibody blocks SEMA3 binding. In another embodiment, the anti-NRP-1 antibody blocks SEMA4 binding. In another embodiment, the antibody blocks interaction between a NRP-1 polypeptide and SEMA3. In another embodiment, the antibody blocks interaction between a NRP-1 polypeptide and VEGF. In one embodiment, the antibody blocks a semaphorin polypeptide binding but does not block VEGF binding. In another embodiment, the anti-NRP-1 antibody is capable of inhibiting Treg suppression in the human subject. In another embodiment, the anti-NRP-1 antibody is capable of decreasing Treg survival and/or stability in the human subject. In one embodiment, the anti-NRP-1 antibody is present in the composition in an amount effective to locally inhibit the NRP-1:semaphorin-4 interaction in a tumor. In another embodiment, the anti-NRP-1 antibody is present in the composition in an amount effective to prevent development of an undesired autoimmune and/or inflammatory manifestation. In one embodiment, human subject is suffering from a cancer. In one embodiment, the amount of the ABP in the pharmaceutical composition is sufficient to (a) reduce the suppression of effector T cells by regulatory T cells; (b) activate effector T cells; (c) reduce the number of regulatory T cells in a tissue or systemically; (d) induce or enhance proliferation of effector T cells; (e) inhibit the rate of tumor growth; (f) induce tumor regression; or (g) combinations thereof, in a subject.

In one embodiment, the pharmaceutical composition is for use as a medicament. In one embodiment, the pharmaceutical composition is for use in the treatment of a cancer or a viral infection. In one embodiment, the pharmaceutical composition is for use in the treatment of a cancer, wherein the cancer is selected from brain, prostate, breast, colon, skin, and lung cancer. In one embodiment, the pharmaceutical composition comprises a pharmaceutically acceptable excipient. In one embodiment, the ABP in the pharmaceutical composition is sufficient to (a) reduce the suppression of effector T cells by regulatory T cells; (b) activate effector T cells; (c) reduce the number of regulatory T cells in a tissue or systemically; (d) induce or enhance proliferation of effector T cells; (e) inhibit the rate of tumor growth; (f) induce tumor regression; or (g) combinations thereof, in a subject.

In another aspect is provided a method of inhibiting a function or decreasing stability of a regulatory T cell (Treg) in a subject, comprising exposing the Treg in vivo to an inhibitor of neuropilin-1 (NRP-1):semaphorin-4A axis in the Treg, wherein an effective amount of an ABP provided herein or a pharmaceutical composition provided herein is administered to the subject. In one embodiment, the method comprises increasing T effector cell ($T_{eff}$) function or exposing the $T_{eff}$ in vivo to an ABP provided herein, comprising administering to a subject an effective amount of a pharmaceutical composition provided herein. In one embodiment, the subject has a cancer. In one embodiment, the method induces or enhances an immune response to a cancer-associated antigen. In one embodiment, the ABP is capable of (a) decreasing Treg survival and/or stability in the human subject; (b) binding to an extracellular domain of the NRP-1 polypeptide; or (c) a combination thereof.

In one embodiment, the method further comprises administering one or more additional therapeutic agents. In one embodiment, the additional therapeutic agent is selected from radiation, a cytotoxic agent, a chemotherapeutic agent, a cytostatic agent, an anti-hormonal agent, a VEGF inhibitor, an immunostimulatory agent, an anti-angiogenic agent, and combinations thereof. In one embodiment, the additional therapeutic agent is an immunostimulatory agent. In one embodiment, the immunostimulatory agent comprises an agent that blocks signaling of an inhibitory receptor expressed by an immune cell or a ligand thereof. In one embodiment, the inhibitory receptor expressed by an immune cell or ligand thereof is selected from PVRIG, VISTA, CCR4, CD27, CTLA-4, PD-1, PD-L1, LAG-3, Tim3, TIGIT, neuritin, BTLA, KIR, and combinations thereof. In one embodiment, the immunostimulatory agent comprises an agonist to a stimulatory receptor expressed by an immune cell. In one embodiment, the stimulatory receptor expressed by an immune cell is selected from OX40, GITR, ICOS, CD28, CD37, CD40, 4-1 BB, and combinations thereof. In one embodiment, the immunostimulatory agent comprises a cytokine. In another embodiment, the immunostimulatory agent comprises a vaccine to a cancer-associated antigen.

In another aspect is provided a method of modulating an immune response in a subject in need thereof, comprising administering to the subject an effective amount of an ABP provided herein. In one embodiment, the method further comprises administering one or more additional therapeutic agents to the subject. In one embodiment, the additional therapeutic agent is (i) an agonist to a stimulatory receptor of an immune cell or (ii) an antagonist of an inhibitory receptor of an immune cell, wherein the receptor of an immune cell is selected from OX40, CD2, CD27, CDS, ICAM-1, LFA-1 (CD11a/CD18), ICOS (CD278), 4-1BB (CD137), CD28, CD30, CD40, BAFFR, HVEM, CD7, LIGHT, NKG2C, GITR, SLAMF7, NKp80, CD160, B7-H3, CD83 ligand, and combinations thereof. In another embodiment, the additional therapeutic agent is an oncolytic virus selected from herpes simplex virus, vesicular stomatitis virus, adenovirus, Newcastle disease virus, vaccinia virus, a maraba virus, and combinations thereof. In one embodiment, the additional therapeutic agent is formulated in the same pharmaceutical composition as the ABP. In another embodiment, the additional therapeutic agent is formulated in a different pharmaceutical composition from the ABP.

In one embodiment, the additional therapeutic agent is administered prior to administering the ABP. In another embodiment, the additional therapeutic agent is administered after administering the ABP. In another embodiment, the additional therapeutic agent is administered contemporaneously with the ABP. In one embodiment, the method does not substantially cause thrombocytopenia in the subject.

In another aspect is provided an anti-human NRP-1 antibody or an antigen-binding fragment thereof, comprising a heavy chain variable region comprising a CDR-H3 consisting of SEQ ID NO:47, a CDR-H2 consisting of SEQ ID NO:30, and a CDR-H1 consisting of SEQ ID NO:14; and a light chain variable region comprising a CDR-L3 consisting of SEQ ID NO:81, a CDR-L2 consisting of SEQ ID NO:71, and a CDR-L1 consisting of SEQ ID NO:63. In one embodiment, the antibody or antigen-binding fragment is selected from any one of the following (1) and (2):
(1) an anti-human NRP-1 antibody or an antigen-binding fragment thereof, comprising a heavy chain variable region consisting of SEQ ID NO:96, and a light chain variable region consisting of SEQ ID NO:104; and
(2) an anti-human NRP-1 antibody or the antigen-binding fragment thereof, comprising a heavy chain variable region consisting of SEQ ID NO:96 in which E of the amino acid number 1 is modified to pyroglutamate, and a light chain variable region consisting of SEQ ID NO:104.

In one embodiment is a method for producing an anti-human NRP-1 antibody or an antigen-binding fragment thereof, comprising culturing host cell(s) selected from the group consisting of (a) to (c) below to express a tetravalent anti-human NRP-1 antibody or an antigen-binding fragment thereof:
(a) a host cell transformed with an expression vector comprising a polynucleotide comprising a base sequence encoding the heavy chain variable region of the anti-human NRP-1 antibody or the antigen-binding fragment thereof of the above embodiment (1) and a polynucleotide comprising a base sequence encoding the light chain variable region of the antibody or the antigen-binding fragment thereof;
(b) a host cell transformed with an expression vector comprising a polynucleotide comprising a base sequence encoding the heavy chain variable region of the anti-human NRP-1 antibody or the antigen-binding fragment thereof of the above embodiment (1) and an expression vector comprising a polynucleotide comprising a base sequence encoding the light chain variable region of the antibody or the antigen-binding fragment thereof; and
(c) a host cell transformed with an expression vector comprising a polynucleotide comprising a base sequence encoding the heavy chain variable region of the anti-human NRP-1 antibody or the antigen-binding fragment thereof of claim the above embodiment (1) and a host cell transformed with an expression vector comprising a polynucleotide comprising a base sequence encoding the light chain variable region of the antibody or the antigen-binding fragment thereof.

In another embodiment is provided (1) a polynucleotide comprising a base sequence encoding the heavy chain variable region of the anti-human NRP-1 antibody or the antigen-binding fragment thereof of the above aspect, and (2) a polynucleotide comprising a base sequence encoding the light chain variable region of the anti-human NRP-1 antibody or the antigen-binding fragment thereof of the above aspect.

In another embodiment is provided an expression vector comprising: (a) a polynucleotide comprising a base sequence encoding the heavy chain variable region of the anti-human NRP-1 antibody or the antigen-binding fragment thereof of the above aspect, and/or (b) a polynucleotide comprising a base sequence encoding the light chain variable region of the anti-human NRP-1 antibody or the antigen-binding fragment thereof of the above aspect.

In another embodiment is provided a host cell transformed with an expression vector selected from the group consisting of (a) to (d):
(a) a host cell transformed with an expression vector comprising a polynucleotide comprising a base sequence encoding the heavy chain variable region of the anti-human NRP-1 antibody or the antigen-binding fragment thereof of the above aspect, and a polynucleotide comprising a base sequence encoding the light chain variable region of the antibody or the antigen-binding fragment thereof;

(b) a host cell transformed with an expression vector comprising a polynucleotide comprising a base sequence encoding the heavy chain variable region of the anti-human NRP-1 antibody or the antigen-binding fragment thereof of the above aspect and an expression vector comprising a polynucleotide comprising a base sequence encoding the light chain variable region of the antibody or the antigen-binding fragment thereof of the above aspect; (c) a host cell transformed with an expression vector comprising a polynucleotide comprising a base sequence encoding the heavy chain variable region of the anti-human NRP-1 antibody or the antigen-binding fragment thereof of the above aspect; and (d) a host cell transformed with an expression vector comprising a polynucleotide comprising a base sequence encoding the light chain variable region of the anti-human NRP-1 antibody or the antigen-binding fragment thereof of the above aspect.

In another embodiment is provided an anti-human NRP-1 antibody or an antigen-binding fragment thereof according to the above aspect, which is selected from the group consisting of (1) to (4):

(1) an anti-human NRP-1 antibody comprising a heavy chain consisting of SEQ ID NO:118, and a light chain consisting of SEQ ID NO:126;

(2) an anti-human NRP-1 antibody comprising a heavy chain consisting of SEQ ID NO:118 in which E of the amino acid number 1 is modified to pyroglutamate, and a light chain consisting of SEQ ID NO:126;

(3) an anti-human NRP-1 antibody comprising a heavy chain consisting of the amino acid sequence of amino acid numbers 1 to 453 of SEQ ID NO:118, and a light chain consisting of SEQ ID NO:126; and (4) an anti-human NRP-1 antibody comprising a heavy chain consisting of the amino acid sequence of amino acid numbers 1 to 453 of SEQ ID NO:118 in which E of the amino acid number 1 is modified to pyroglutamate, and a light chain consisting of SEQ ID NO:126.

In one embodiment, the anti-human NRP-1 antibody is for use in preventing or treating cancer. In another embodiment, the anti-human NRP-1 antibody is for manufacture of a pharmaceutical composition for preventing or treating cancer.

A polynucleotide, which is selected from the group consisting of (1) and (2):

(1) a polynucleotide comprising a base sequence encoding the heavy chain of the anti-human NRP-1 antibody according to the above embodiment (1), and (2) a polynucleotide comprising a base sequence encoding the light chain of the anti-human NRP-1 antibody according to the above embodiment (1).

An expression vector comprising:

(a) a polynucleotide comprising a base sequence encoding the heavy chain of the anti-human NRP-1 antibody of the above embodiment (1), and/or (b) a polynucleotide comprising a base sequence encoding the light chain of the anti-human NRP-1 antibody of the above embodiment (1).

A host cell transformed with an expression vector selected from the group consisting of (a) to (d):

(a) a host cell transformed with an expression vector comprising a polynucleotide comprising a base sequence encoding the heavy chain of the anti-human NRP-1 antibody of the above embodiment (1) and a polynucleotide comprising a base sequence encoding the light chain of the antibody;

(b) a host cell transformed with an expression vector comprising a polynucleotide comprising a base sequence encoding the heavy chain of the anti-human NRP-1 antibody of the above embodiment (1) and an expression vector comprising a polynucleotide comprising a base sequence encoding the light chain of the antibody;

(c) a host cell transformed with an expression vector comprising a polynucleotide comprising a base sequence encoding the heavy chain of the anti-human NRP-1 antibody of the above embodiment (1); and (d) a host cell transformed with an expression vector comprising a polynucleotide comprising a base sequence encoding the light chain of the anti-human NRP-1 antibody of the above embodiment (1).

A method for producing an anti-human NRP-1 antibody, comprising culturing host cell(s) selected from the group consisting of (a) to (c) below to express an anti-human NRP-1 antibody:

(a) a host cell transformed with an expression vector comprising a polynucleotide comprising a base sequence encoding the heavy chain of the anti-human NRP-1 antibody of the above embodiment (1) and a polynucleotide comprising a base sequence encoding the light chain of the antibody;

(b) a host cell transformed with an expression vector comprising a polynucleotide comprising a base sequence encoding the heavy chain of the anti-human NRP-1 antibody of the above embodiment (1) and an expression vector comprising a polynucleotide comprising a base sequence encoding the light chain of the antibody; and (c) a host cell transformed with an expression vector comprising a polynucleotide comprising a base sequence encoding the heavy chain of the anti-human NRP-1 antibody of the above embodiment (1) and a host cell transformed with an expression vector comprising a polynucleotide comprising a base sequence encoding the light chain of the antibody.

In one embodiment is provided a pharmaceutical composition comprising the anti-human NRP-1 antibody of the above embodiment and a pharmaceutically acceptable excipient. In another embodiment is provided a pharmaceutical composition comprising the anti-human NRP-1 antibody of the above embodiment (1), the anti-human NRP-1 antibody of the above embodiment (2), the anti-human NRP-1 antibody of the above embodiment (3), and/or the anti-human NRP-1 antibody of the above embodiment (4), and a pharmaceutically acceptable excipient. In one embodiment the pharmaceutical composition is a pharmaceutical composition for treating cancer. In another embodiment, the composition is administered in combination with radiation, a cytotoxic agent, a chemotherapeutic agent, a cytostatic agent, an anti-hormonal agent, a VEGF inhibitor, an immunostimulatory agent, an anti-angiogenic agent, or combinations thereof.

In another embodiment is provided a method for preventing or treating cancer, comprising administering a therapeutically effective amount of the anti-human NRP-1 antibody of the above aspect. In one embodiment, the method further comprises administering one or more additional therapeutic agents. In one embodiment, the additional therapeutic agent is selected from the group consisting of radiation, a cytotoxic agent, a chemotherapeutic agent, a cytostatic agent, an anti-hormonal agent, a VEGF inhibitor, an immunostimulatory agent, an anti-angiogenic agent, and combinations thereof.

DETAILED DESCRIPTION

1. Definitions

Figure 1A:
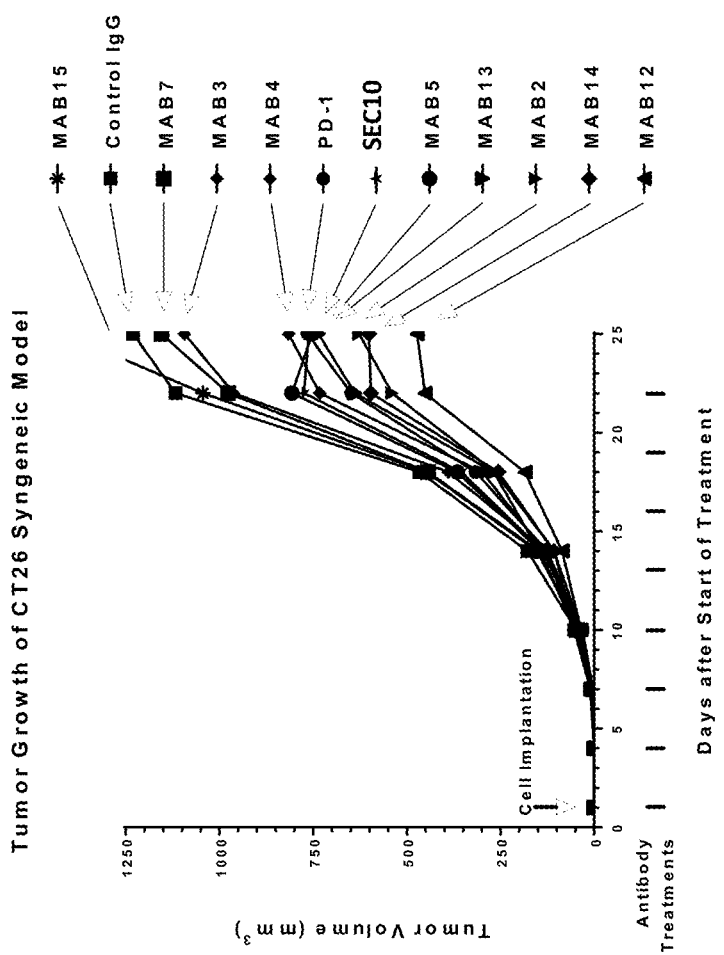
FIG. 1A is graphs showing tumor growth inhibition in CT26 tumor-bearing mice treated with a murine version of MABs 2, 3, 4, 5, 7, 12, 13, 14, and 15, as well as an IgG control and the anti-NRP-1 antibody SEC10 as a comparator. Mice were treated with MAB monotherapy (FIG. 1A). Antibody treatment times (days) are shown by arrows.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, N.Y. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise The term "about" indicates and encompasses an indicated value and a range above and below that value. In certain embodiments, the term "about" indicates the designated value±10%, ±5%, or ±1%. In certain embodiments, where applicable, the term "about" indicates the designated value(s)±one standard deviation of that value(s).

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antigen-binding protein" (ABP) refers to a protein comprising one or more antigen-binding domains that specifically bind to an antigen or epitope. In some embodiments, the antigen-binding domain binds the antigen or epitope with specificity and affinity similar to that of naturally occurring antibodies. In some embodiments, the ABP comprises an antibody. In some embodiments, the ABP consists of an antibody. In some embodiments, the ABP consists essentially of an antibody. In some embodiments, the ABP comprises an alternative scaffold. In some embodiments, the ABP consists of an alternative scaffold. In some embodiments, the ABP consists essentially of an alternative scaffold. In some embodiments, the ABP comprises an antibody fragment. In some embodiments, the ABP consists of an antibody fragment. In some embodiments, the ABP consists essentially of an antibody fragment. A "NRP-1 ABP," "anti-NRP-1 ABP," or "NRP-1-specific ABP" is an ABP, as provided herein, which specifically binds to the antigen NRP-1. In some embodiments, the ABP binds the extracellular domain of NRP-1. In certain embodiments, a NRP-1 ABP provided herein binds to an epitope of NRP-1 that is conserved between or among NRP-1 proteins from different species.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies. An antibody is one type of ABP.

The term "antigen-binding domain" means the portion of an ABP that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an adnectin.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains. An "anti-human NRP-1 antibody" is the intact antibody, as provided herein, which specifically binds to the human NRP-1.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, *J. Allergy Clin. Immunol.*, 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); Al-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Plückthun, *J. Mol. Biol.*, 2001, 309:657-70 ("AHo" numbering scheme); each of which is incorporated by reference in its entirety.

Table 1 provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

TABLE 1

Residues in CDRs according to Kabat and Chothia numbering schemes.

| CDR | Kabat | Chothia |
| --- | --- | --- |
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" or an "antigen-binding fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with 1-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a (GGGGS)$_n$ (SEQ ID NO:140). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used. In some cases, the Fc domain comprises an IgG4 Fc domain.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.*, 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

By "SEC10" is meant an anti-NRP-1 antibody previously in clinical trials for treatment of solid tumors, with and without bevacizumab. See, e.g., "A Study of MNRP1685A in Patients with Locally Advanced or Metastatic Solid Tumors," clinicaltrials.gov Identifier NCT00747734.

By "SEC3" is meant the pan-anti-NRP-1 antibody set forth in SEQ ID NO:144, also described, e.g., in Appleton, et. al., *The EMBO Journal* (2007) 26, 4902-4912.

By "MAB59941" is meant an anti-mouse Neuropilin-1 antibody available from R&D Systems, Clone #761704.

An "isolated ABP" or "isolated nucleic acid" is an ABP or nucleic acid that has been separated and/or recovered from a component of its natural environment. Components of the natural environment may include enzymes, hormones, and other proteinaceous or nonproteinaceous materials. In some embodiments, an isolated ABP is purified to a degree sufficient to obtain at least 15 residues of N-terminal or internal amino acid sequence, for example by use of a spinning cup sequenator. In some embodiments, an isolated ABP is purified to homogeneity by gel electrophoresis (e.g., SDS-PAGE) under reducing or nonreducing conditions, with detection by Coomassie blue or silver stain. In some embodiments, an isolated ABP may include an ABP in situ within recombinant cells, since at least one component of the ABP's natural environment is not present. In some aspects, an isolated ABP or isolated nucleic acid is prepared by at least one purification step. In some embodiments, an isolated ABP or isolated nucleic acid is purified to at least 80%, 85%, 90%, 95%, or 99% by weight. In some embodiments, an isolated ABP or isolated nucleic acid is purified to at least 80%, 85%, 90%, 95%, or 99% by volume. In some embodiments, an isolated ABP or isolated nucleic acid is provided as a solution comprising at least 85%, 90%, 95%, 98%, 99% to 100% ABP or nucleic acid by weight. In some embodiments, an isolated ABP or isolated nucleic acid is provided as a solution comprising at least 85%, 90%, 95%, 98%, 99% to 100% ABP or nucleic acid by volume.

"Affinity" refers to the strength of the sum total of non-covalent interactions between a single binding site of a molecule (e.g., an ABP) and its binding partner (e.g., an antigen or epitope). Unless indicated otherwise, as used herein, "affinity" refers to intrinsic binding affinity, which reflects a 1:1 interaction between members of a binding pair (e.g., ABP and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an ABP to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the ABP to the target molecule is competitively inhibited by the control molecule. In some aspects, the affinity of a NRP-1 ABP for a non-target molecule is less than about 50% of the affinity for NRP-1. In some aspects, the affinity of a NRP-1 ABP for a non-target molecule is less than about 40% of the affinity for NRP-1. In some aspects, the affinity of a NRP-1 ABP for a non-target molecule is less than about 30% of the affinity for NRP-1. In some aspects, the affinity of a NRP-1 ABP for a non-target molecule is less than about 20% of the affinity for NRP-1. In some aspects, the affinity of a NRP-1 ABP for a non-target molecule is less than about 10% of the affinity for NRP-1. In some aspects, the affinity of a NRP-1 ABP for a non-target molecule is less than about 1% of the affinity for NRP-1. In some aspects, the affinity of a NRP-1 ABP for a non-target molecule is less than about 0.1% of the affinity for NRP-1.

The term "$k_d$" ($sec^{-1}$), as used herein, refers to the dissociation rate constant of a particular ABP-antigen interaction. This value is also referred to as the $k_{off}$ value.

The term "$k_a$" ($M^{-1} \times sec^{-1}$), as used herein, refers to the association rate constant of a particular ABP-antigen interaction. This value is also referred to as the $k_{on}$ value.

The term "$K_D$" (M), as used herein, refers to the dissociation equilibrium constant of a particular ABP-antigen interaction. $K_D=k_d/k_a$. In some embodiments, the affinity of an ABP is described in terms of the $K_D$ for an interaction between such ABP and its antigen. For clarity, as known in the art, a smaller $K_D$ value indicates a higher affinity interaction, while a larger $K_D$ value indicates a lower affinity interaction.

The term "$K_A$" ($M^{-1}$), as used herein, refers to the association equilibrium constant of a particular ABP-antigen interaction. $K_A=k_a/k_d$.

An "affinity matured" ABP is an ABP with one or more alterations (e.g., in one or more CDRs or FRs) relative to a parent ABP (i.e., an ABP from which the altered ABP is derived or designed) that result in an improvement in the affinity of the ABP for its antigen, compared to the parent ABP which does not possess the alteration(s). In some embodiments, an affinity matured ABP has nanomolar or picomolar affinity for the target antigen. Affinity matured ABPs may be produced using a variety of methods known in the art. For example, Marks et al. (*Bio/Technology*, 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.*, 1994, 91:3809-3813); Schier et al., *Gene*, 1995, 169:147-155; Yelton et al., *J. Immunol.*, 1995, 155:1994-2004; Jackson et al., *J. Immunol.*, 1995, 154:3310-33199; and Hawkins et al, *J. Mol. Biol.*, 1992, 226:889-896; each of which is incorporated by reference in its entirety.

An "immunoconjugate" is an ABP conjugated to one or more heterologous molecule(s), such as a therapeutic or diagnostic agent.

"Effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more ABPs, the term "competes with" or "cross-competes with" indicates that the two or more ABPs compete for binding to an antigen (e.g., NRP-1). In one exemplary assay, NRP-1 is coated on a surface and contacted with a first NRP-1 ABP, after which a second NRP-1 ABP is added. In another exemplary assay, a first NRP-1 ABP is coated on a surface and contacted with NRP-1, and then a second NRP-1 ABP is added. If the presence of the first NRP-1 ABP reduces binding of the second NRP-1 ABP, in either assay, then the ABPs compete with each other. The term "competes with" also includes combinations of ABPs where one ABP reduces binding of another ABP, but where no competition is observed when the ABPs are added in the reverse order. However, in some embodiments, the first and second ABPs inhibit binding of each other, regardless of the order in which they are added. In some embodiments, one ABP reduces binding of another ABP to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the ABPs for NRP-1 and the valency of the ABPs. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J. Pharm. Biomed. Anal.*, 2011, 54:351-358; each of which is incorporated by reference in its entirety.

The term "epitope" means a portion of an antigen that specifically binds to an ABP. Epitopes frequently consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an ABP binds can be determined using known techniques for epitope determination such as, for example, testing for ABP binding to NRP-1 variants with different point-mutations, or to chimeric NRP-1 variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |

TABLE 2-continued

Selected groups of amino acids that are considered conservative substitutions for one another, in certain embodiments.

| | |
|---|---|
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F, Y, and W |
| Group G | S and T |
| Group H | C and M |

Additional conservative substitutions may be found, for example, in Creighton, *Proteins: Structures and Molecular Properties* 2nd ed. (1993) W.H. Freeman & Co., New York, N.Y. An ABP generated by making one or more conservative substitutions of amino acid residues in a parent ABP is referred to as a "conservatively modified variant."

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an ABP or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, and sheep. In certain embodiments, the subject is a human. In some embodiments, the subject has a disease or condition that can be treated with an ABP provided herein. In some aspects, the disease or condition is a cancer. In some aspects, the disease or condition is a viral infection.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

The term "cytotoxic agent," as used herein, refers to a substance that inhibits or prevents a cellular function and/or causes cell death or destruction.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein. The terms "cell proliferative disorder" and "proliferative disorder" refer to disorders that are associated with some degree of abnormal cell proliferation. In some embodiments, the cell proliferative disorder is a cancer. In some aspects, the tumor is a solid tumor. In some aspects, the tumor is a hematologic malignancy.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor. An antagonist in one embodiment blocks 100% of binding of a ligand to its receptor; in other embodiments, an antagonist may reduce binding by 1, 2, 3, 4, 5, 6, 7, 8, 9, 10, 20, 30, 40, 50, 60, 70, 80, 90, 91, 92, 93, 94, 95, 96, 97, 98, 99, or 100% of binding of a ligand to its receptor.

The term "a semaphorin molecule" as used herein in connection with agonists of the NRP-1:semaphorin axis of Tregs encompasses transmembrane semaphorin molecules involved in interaction with NRP-1 on Tregs (e.g., Sema3a, Sema4a), various surface- and bead-immobilized versions of such molecules, as well as multimers, derivatives, mutants, analogs, and fragments of such molecules which can be used to enhance a function or increase stability of Tregs. Non-limiting examples of such agonist semaphorin molecules include, for example, IgM-derived semaphorin fusion proteins that assemble multimeric complexes incapable of fixing complement, that crosslink NRP-1.

The term "neuropilin-1 (NRP-1):semaphorin axis of a regulatory T cell (Treg)" as used herein refers to the signaling pathway initiated by semaphorin (e.g., a semaphorin expressed by a cell such as, e.g., a conventional T cell, or a recombinant semaphorin), ligation of NRP-1, and the subsequent downstream signaling.

The term "effector T cell" includes T helper (i.e., CD4+) cells and cytotoxic (i.e., CD8+) T cells. CD4+ effector T cells contribute to the development of several immunologic processes, including maturation of B cells into plasma cells and memory B cells, and activation of cytotoxic T cells and macrophages. CD8+ effector T cells destroy virus-infected cells and tumor cells. See Seder and Ahmed, *Nature Immunol.*, 2003, 4:835-842, incorporated by reference in its entirety, for additional information on effector T cells.

The term "regulatory T cell" includes cells that regulate immunological tolerance, for example, by suppressing effector T cells. In some aspects, the regulatory T cell has a CD4+CD25+ Foxp3+ phenotype. In some aspects, the regulatory T cell has a CD8+CD25+ phenotype. See Nocentini et al., *Br. J. Pharmacol.*, 2012, 165:2089-2099, incorporated by reference in its entirety, for additional information on regulatory T cells expressing NRP-1.

The term "dendritic cell" refers to a professional antigen-presenting cell capable of activating a naïve T cell and stimulating growth and differentiation of a B cell.

2. NRP-1 Antigen-Binding Proteins 2.1 NRP-1 Binding and Target Cells

Provided herein are ABPs that specifically bind to NRP-1. In some aspects, the NRP-1 is hNRP-1 (SEQ ID NO:130). In some aspects, the NRP-1 is cNRP-1 (SEQ ID NO:132). In some aspects, the NRP-1 is mNRP-1 with the sequence provided in SEQ ID NO:134. In some aspects, the NRP-1 is rNRP-1 with the sequence provided in SEQ ID NO:135.

In some embodiments, the ABPs provided herein specifically bind to the extracellular domain of NRP-1.

In some embodiments, the ABPs provided herein specifically bind to the extracellular domain of NRP-1 and the extracellular domain of PD-1, PD-L1, or PD-L2, i.e., are bispecific antibodies.

In some embodiments, an ABP provided herein is an antibody. In some embodiments, an ABP provided herein is an antibody fragment. In some embodiments, an ABP provided herein is an alternative scaffold.

The NRP-1 may be expressed on the surface of any suitable target cell. In some embodiments, the target cell is a T cell. In some embodiments, the target cell is an effector T cell. In some embodiments, the target cell is a regulatory T cell. In some embodiments, the target cell is a natural killer (NK) cell. In some embodiments, the target cell is a natural killer T (NKT) cell. In some embodiments, the target cell is a macrophage. In other embodiments, the target cell is a dendritic cell. In one embodiment, the dendritic cell is a plasmacytoid dendritic cell.

In some embodiments, the NRP-1 is associated with another receptor on the surface of the cell. In some embodiments, the NRP-1 is part of a co-receptor complex. In one embodiment, the NRP-1 is associated with a plexin. In some embodiments, the NRP-1 is associated with a VEGF receptor.

In some embodiments, the ABPs provided herein comprise an immunoglobulin molecule. In some embodiments, the ABPs provided herein consist of an immunoglobulin molecule. In some embodiments, the ABPs provided herein consist essentially of an immunoglobulin molecule. In some aspects, the immunoglobulin molecule comprises an antibody. In some aspects, the immunoglobulin molecule consists of an antibody. In some aspects, the immunoglobulin molecule consists essentially of an antibody.

In some embodiments, the ABPs provided herein comprise a light chain. In some aspects, the light chain is a kappa light chain. In some aspects, the light chain is a lambda light chain.

In some embodiments, the ABPs provided herein comprise a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the ABPs provided herein comprise an antibody fragment. In some embodiments, the ABPs provided herein consist of an antibody fragment. In some embodiments, the ABPs provided herein consist essentially of an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment. In some aspects, the antibody fragment is a fragment of a single domain antibody.

In some embodiments, an antibody fragment provided herein is derived from an illustrative antibody provided herein. In some embodiments, an antibody fragments provided herein is not derived from an illustrative antibody provided herein and may, for example, be isolated de novo according to the methods provided herein for obtaining antibody fragments.

In some embodiments, an antibody fragment provided specifically binds hNRP-1. In some embodiments, an antibody fragment provided herein specifically binds cNRP-1. In some embodiments, an antibody fragment provided herein specifically binds mNRP-1. In some embodiments, an antibody fragment provided herein specifically binds hNRP-1 and cNRP-1. In some embodiments, an antibody fragment provided herein specifically binds hNRP-1 and mNRP-1. In some embodiments, an antibody fragment provided herein specifically binds cNRP-1 and mNRP-1. In some embodiments, an antibody fragment provided herein specifically binds hNRP-1, cNRP-1 and mNRP-1.

In some embodiments, an antibody fragment provided herein retains the ability to antagonize NRP-1, as measured by one or more assays or biological effects described herein. In some embodiments, an antibody fragment provided herein retains the ability to prevent NRP-1 from interacting with one or more of its ligands, as described herein.

In some embodiments, an antibody fragment provided herein competes for binding to NRP-1 with an antibody selected from MAB1, MAB2, MAB3, MAB4, MAB5, MAB6, MAB7, MAB8, MAB9, MAB10, MAB11, MAB12, MAB13, MAB14, or MAB15, each as provided in Appendix A of this disclosure.

In some embodiments, the ABPs provided herein are specific for cell surface NRP-1.

In some embodiments, the ABPs provided herein are specifically block NRP-1 binding to a transmembrane semaphorin polypeptide.

In some embodiments, the ABPs provided herein block the interaction between a NRP-1 polypeptide and a vascular endothelial cell growth factor (VEGF) polypeptide. In one embodiment, the VEGF polypeptide is VEGFA.

In some embodiments, the anti-NRP-1 antibody blocks SEMA3 binding.

In some embodiments, the anti-NRP-1 antibody blocks SEMA4 binding.

In some embodiments, the antibody blocks interaction between a NRP-1 polypeptide and SEMA3.

In some embodiments, the antibody blocks interaction between a NRP-1 polypeptide and VEGF.

In some embodiments, the ABPs provided herein are capable of inhibiting Treg suppression in a human subject.

In some embodiments, the ABPs provided herein co-stimulate an effector T cell in combination with antigen presentation from an antigen-presenting cell.

In some embodiments, the ABPs provided herein inhibit the suppression of an effector T cell by a regulatory T cell.

In some embodiments, the ABPs provided herein reduce the number of effector T cells in a tissue or in systemic circulation.

In some embodiments, a fragment of an antibody provided herein binds the same epitope of NRP-1 as such antibody.

In some embodiments, the ABPs provided herein are monoclonal antibodies. In some embodiments, the ABPs provided herein are polyclonal antibodies.

In some embodiments, the ABPs provided herein comprise a chimeric antibody. In some embodiments, the ABPs provided herein consist of a chimeric antibody. In some embodiments, the ABPs provided herein consist essentially of a chimeric antibody. In some embodiments, the ABPs provided herein comprise a humanized antibody. In some embodiments, the ABPs provided herein consist of a humanized antibody. In some embodiments, the ABPs provided herein consist essentially of a humanized antibody. In some embodiments, the ABPs provided herein comprise a human antibody. In some embodiments, the ABPs provided herein consist of a human antibody. In some embodiments, the ABPs provided herein consist essentially of a human antibody.

In some embodiments, the ABPs provided herein are affinity matured. In some aspects, the affinity matured ABPs are affinity matured ABPs derived from an illustrative ABP provided herein.

In some embodiments, the ABPs provided herein comprise an alternative scaffold. In some embodiments, the ABPs provided herein consist of an alternative scaffold. In some embodiments, the ABPs provided herein consist essentially of an alternative scaffold. Any suitable alternative scaffold may be used. In some aspects, the alternative scaffold is selected from an Adnectin™, an iMab, an Anticalin®, an EETI-II/AGRP, a Kunitz domain, a thioredoxin peptide aptamer, an Affibody®, a DARPin, an Affilin, a Tetranectin, a Fynomer, and an Avimer.

In some embodiments, an ABP provided herein specifically blocks binding of NRP-1 to a transmembrane semaphorin polypeptide. In some aspects, the ABP inhibits binding of NRP-1 to a transmembrane semaphorin polypeptide by at least about 50%. In some aspects, the ABP inhibits binding of NRP-1 to a transmembrane semaphorin polypeptide by at least about 75%. In some aspects, the ABP inhibits binding of NRP-1 to a transmembrane semaphorin polypeptide by at least about 90%. In some aspects, the ABP inhibits binding of NRP-1 to a transmembrane semaphorin polypeptide by at least about 95%. In some embodiments, the semaphorin polypeptide is a SEMA3 polypeptide. In other embodiments, the semaphorin polypeptide is a SEMA4 polypeptide.

In some embodiments, an ABP of the invention is an ABP that competes with an illustrative ABP provided herein. In some aspects, the ABP that competes with the illustrative ABP provided herein binds the same epitope as an illustrative ABP provided herein.

It is known that when an antibody is expressed in cells, the antibody is modified after translation. Examples of the posttranslational modification include cleavage of lysine at the C terminal of the heavy chain by a carboxypeptidase; modification of glutamine or glutamic acid at the N terminal of the heavy chain and the light chain to pyroglutamic acid by pyroglutamylation; glycosylation; oxidation; deamidation; and glycation, and it is known that such posttranslational modifications occur in various antibodies (See Journal of Pharmaceutical Sciences, 2008, Vol. 97, p. 2426-2447, incorporated by reference in its entirety). In some embodiments, an ABP of the invention is an antibody or antigen-binding fragment thereof which has undergone posttranslational modification. Examples of an antibody or antigen-binding fragment thereof which have undergone posttranslational modification include an antibody or antigen-binding fragments thereof which have undergone pyroglutamylation at the N terminal of the heavy chain variable region, pyroglutamylation at the N terminal of the light chain variable region, and/or deletion of lysine at the C terminal of the heavy chain. It is known in the art that such posttranslational modification due to pyroglutamylation at the N terminal and deletion of lysine at the C terminal does not have any influence on the activity of the antibody or fragment thereof (Analytical Biochemistry, 2006, Vol. 348, p. 24-39, incorporated by reference in its entirety).

In some embodiments, an ABP of the invention is an anti-human NRP-1 antibody or an antigen-binding fragment thereof, comprising a heavy chain variable region comprising a CDR-H3 consisting of SEQ ID NO:47, a CDR-H2 consisting of SEQ ID NO:30, and a CDR-H1 consisting of SEQ ID NO:14; and a light chain variable region comprising a CDR-L3 consisting of SEQ ID NO:81, a CDR-L2 consisting of SEQ ID NO:71, and a CDR-L1 consisting of SEQ ID NO:63

In one embodiment, the anti-human NRP-1 antibody or an antigen-binding fragment thereof, comprising a heavy chain variable region consisting of SEQ ID NO:96, and a light chain variable region consisting of SEQ ID NO:104.

In one embodiment, the anti-human NRP-1 antibody or the antigen-binding fragment thereof, comprising a heavy chain variable region consisting of SEQ ID NO:96 in which E of the amino acid number 1 is modified to pyroglutamate, and a light chain variable region consisting of SEQ ID NO:104.

In one embodiment, the anti-human NRP-1 antibody comprising a heavy chain consisting of SEQ ID NO:118, and a light chain consisting of SEQ ID NO:126.

In one embodiment, the anti-human NRP-1 antibody comprising a heavy chain consisting of SEQ ID NO:118 in which E of the amino acid number 1 is modified to pyroglutamate, and a light chain consisting of SEQ ID NO:126.

In one embodiment, the anti-human NRP-1 antibody comprising a heavy chain consisting of the amino acid sequence of amino acid numbers 1 to 453 of SEQ ID NO:118, and a light chain consisting of SEQ ID NO:126.

In one embodiment, the anti-human NRP-1 antibody comprising a heavy chain consisting of the amino acid sequence of amino acid numbers 1 to 453 of SEQ ID NO:118 in which E of the amino acid number 1 is modified to pyroglutamate, and a light chain consisting of SEQ ID NO:126.

2.2 NRP-1 Antagonism

In some embodiments, the ABPs provided herein antagonize NRP-1 upon binding.

In some embodiments, antagonism of NRP-1 by an ABP provided herein results in activation of an effector T cell. In some aspects, the effector T cell is a CD8+ T cell. In some aspects, the effector T cell is a CD4+ T cell.

In some embodiments, antagonism of NRP-1 by an ABP provided herein results in activation of an NK cell. In some embodiments, antagonism of NRP-1 by an ABP provided herein results in activation of an NKT cell. In some embodiments, the NKT cell is an IL-17-secreting cell.

In some embodiments, antagonism of NRP-1 by an ABP provided herein results in a reduction of the inhibitory activity of a regulatory T cell toward an effector T cell.

In some embodiments, antagonism of NRP-1 by an ABP provided herein results in increased secretion of IL-2, IL-6, GM-CSF, TNF, LT-α, and/or IFN-γ by a target cell.

In some embodiments, antagonism of NRP-1 by an ABP provided herein increases the proliferation, survival, and/or function of an effector T cell. In some aspects, the effector T cell is a CD4+ effector T cell. In some aspects, the effector T cell is a CD8+ effector T cell.

In some embodiments, antagonism of NRP-1 by an ABP provided herein abrogates suppression of an effector T cell by a regulatory T cell. In some aspects, the regulatory T cell is a CD4+CD25+ Foxp3+ regulatory T cell. In some aspects, the regulatory T cell is a CD8+CD25+ regulatory T cell.

In some embodiments, antagonism of NRP-1 by an ABP provided herein results in an enhancement of an immune response.

In some embodiments, antagonism of NRP-1 by an ABP provided herein results in the prevention of a tumor. In some embodiments, antagonism of NRP-1 by an ABP provided herein results in the delay of onset of a tumor. In some embodiments, antagonism of NRP-1 by an ABP provided herein results in a reduction of the size of a tumor. In some embodiments, antagonism of NRP-1 by an ABP provided herein results in elimination of a tumor. In some embodiments, antagonism of NRP-1 by an ABP provided herein results in a reduction in the number of metastases.

In some embodiments, antagonism of NRP-1 by an ABP provided herein results in the prevention of a viral disease. In some embodiments, antagonism of NRP-1 by an ABP provided herein results in the delay of onset of a viral disease. In some embodiments, antagonism of NRP-1 by an ABP provided herein results in a reduction of the viral load in a subject. In some embodiments, antagonism of NRP-1 by an ABP provided herein results in the elimination of a viral infection.

2.3 Affinity and Kinetics of Antigen-Binding Proteins for NRP-1; Potency

In some embodiments, the affinity of an ABP provided herein for NRP-1 as indicated by $K_D$, is less than about $10^{-5}$ M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the ABP is between about $10^{-7}$ M and $10^{-12}$ M. In some embodiments, the affinity of the ABP is between about $10^{-7}$ M and $10^{-11}$ M. In some embodiments, the affinity of the ABP is between about $10^{-7}$ M and $10^{-9}$ M. In some embodiments, the affinity of the ABP is between about $10^{-7}$ M and $10^{-9}$ M. In some embodiments, the affinity of the ABP is between about $10^{-7}$ M and $10^{-8}$ M. In some embodiments, the affinity of the ABP is between about $10^{-8}$ M and $10^{-12}$ M. In some embodiments, the affinity of the ABP is between about $10^{-8}$ M and $10^{-11}$ M. In some embodiments, the affinity of the ABP is between about $10^{-9}$ M and $10^{-11}$ M. In some embodiments, the affinity of the ABP is between about $10^{-10}$ M and $10^{-11}$ M.

2.3.1 Glycosylation Variants

In certain embodiments, an ABP provided herein may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an ABP provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an ABP.

In some embodiments, an ABP provided herein comprises a glycosylation motif that is different from a naturally occurring ABP. Any suitable naturally occurring glycosylation motif can be modified in the ABPs provided herein. The structural and glycosylation properties of immunoglobulins, for example, are known in the art and summarized, for example, in Schroeder and Cavacini, *J. Allergy Clin. Immunol.*, 2010, 125:S41-52, incorporated by reference in its entirety.

In some embodiments, an ABP provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH*, 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create ABPs having altered ADCC. In some embodiments, the oligosaccharide is altered to improve ADCC. In some embodiments, the oligosaccharide is altered to reduce ADCC.

In some aspects, an ABP provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such ABPs do not comprise any fucose at position Asn 297. The amount of fucose may be determined using any suitable method, for example as described in WO 2008/077546, incorporated by reference in its entirety.

In some embodiments, an ABP provided herein comprises a bisected oligosaccharide, such as a biantennary oligosaccharide attached to the Fc region of the ABP that is bisected by GlcNAc. Such ABP variants may have reduced fucosylation and/or improved ADCC function. Examples of such ABP variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the ABPs provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87: 614-622; each of which is incorporated by reference in its entirety.

In some embodiments, an ABP provided herein comprises an Fc region with at least one galactose residue in the oligosaccharide attached to the Fc region. Such ABP variants may have improved CDC function. Examples of such ABP variants are described, for example, in WO 1997/30087; WO 1998/58964; and WO 1999/22764; each of which his incorporated by reference in its entirety.

Examples of cell lines capable of producing defucosylated ABPs include Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety).

In some embodiments, an ABP provided herein is an aglycosylated ABP. An aglycosylated ABP can be produced using any method known in the art or described herein. In some aspects, an aglycosylated ABP is produced by modifying the ABP to remove all glycosylation sites. In some aspects, the glycosylation sites are removed only from the Fc region of the ABP. In some aspects, an aglycosylated ABP is produced by expressing the ABP in an organism that is not capable of glycosylation, such as *E. coli*, or by expressing the ABP in a cell-free reaction mixture.

In some embodiments, an ABP provided herein has a constant region with reduced effector function compared to a native IgG1 antibody. In some embodiments, the affinity of a constant region of an Fc region of an ABP provided herein for Fc receptor is less than the affinity of a native IgG1 constant region for such Fc receptor.

2.4 NRP-1 Domains

NRP-1 has both a transmembrane and a truncated form. The transmembrane form is as follows. Following a short stretch of secretion signal, NRP-1 consists of four different domains: two repeats of CUB domain (a1/a2), two repeats of FV/VIII domain (b1/b2), a MAM (c) domain, and a fourth domain (d) that contains transmembrane and relatively short 40 to 43 amino acid cytoplasmic region. The first CUB domains have significant homology with complement factor C1s/C1r, Bone Morphogenetic Protein 1(BMP1), and Tolloid proteins. The second FV/VIII domain shares the homology with coagulation factor FV/VIII, one of the receptor type tyrosine kinase DDR, and discoidin-1. The third domain MAM is the abbreviation of meprin, A5 (former name of NRP), and receptor protein-tyrosine phosphatase mu and kappa. In one embodiment, an ABP provided herein binds to the a1 domain. In another embodiment, an ABP provided herein binds to the a2 domain. In another embodiment, an ABP provided herein binds to the b1 domain. In another embodiment, an ABP provided herein binds to the b2 domain. In one embodiment, an ABP provided herein binds to more than one domain.

1.1. Fc Region Amino Acid Sequence Variants

In certain embodiments, an ABP provided herein comprises an Fc region with one or more amino acid substitutions, insertions, or deletions in comparison to a naturally occurring Fc region. In some aspects, such substitutions, insertions, or deletions yield ABPs with altered stability, glycosylation, or other characteristics. In some aspects, such substitutions, insertions, or deletions yield aglycosylated ABPs.

In some aspects, the Fc region of an ABP provided herein is modified to yield an ABP with altered affinity for an Fc receptor, or an ABP that is more immunologically inert. In some embodiments, the ABP variants provided herein possess some, but not all, effector functions. Such ABPs may be useful, for example, when the half-life of the ABP is important in vivo, but when certain effector functions (e.g., complement activation and ADCC) are unnecessary or deleterious.

In some embodiments, the Fc region of an ABP provided herein is a human IgG4 Fc region comprising one or more of the hinge stabilizing mutations S228P and L235E. See Aalberse et al., *Immunology,* 2002, 105:9-19, incorporated by reference in its entirety. In some embodiments, the Fc region of an ABP provided herein is a human IgG4 Fc region comprising the hinge stabilizing mutations S228P. In some embodiments, the IgG4 Fc region comprises one or more of the following mutations: E233P, F234V, and L235A. See Armour et al., *Mol. Immunol.,* 2003, 40:585-593, incorporated by reference in its entirety. In some embodiments, the IgG4 Fc region comprises a deletion at position G236.

In some embodiments, the Fc region of an ABP provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A). In some aspects, the ABP comprises a PVA236 mutation. PVA236 means that the amino acid sequence ELLG (SEQ ID NO: 147), from amino acid position 233 to 236 of IgG1 or EFLG (SEQ ID NO: 148) of IgG4, is replaced by PVA. See U.S. Pat. No. 9,150,641, incorporated by reference in its entirety.

In some embodiments, the Fc region of an ABP provided herein is modified as described in Armour et al., *Eur. J. Immunol.,* 1999, 29:2613-2624; WO 1999/058572; and/or U.K. Pat. App. No. 98099518; each of which is incorporated by reference in its entirety.

In some embodiments, the Fc region of an ABP provided herein is a human IgG2 Fc region comprising one or more of mutations A330S and P331S.

In some embodiments, the Fc region of an ABP provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more of amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the ABP comprises an alanine at amino acid position 265. In some embodiments, the ABP comprises an alanine at amino acid position 297.

In certain embodiments, an ABP provided herein comprises an Fc region with one or more amino acid substitutions which improve ADCC, such as a substitution at one or more of positions 298, 333, and 334 of the Fc region. In some embodiments, an ABP provided herein comprises an Fc region with one or more amino acid substitutions at positions 239, 332, and 330, as described in Lazar et al., *Proc. Natl. Acad. Sci. USA,* 2006, 103:4005-4010, incorporated by reference in its entirety.

In some embodiments, an ABP provided herein comprises one or more alterations that improves or diminishes C1q binding and/or CDC. See U.S. Pat. No. 6,194,551; WO 99/51642; and Idusogie et al., *J. Immunol.,* 2000, 164:4178-4184; each of which is incorporated by reference in its entirety.

In some embodiments, an ABP provided herein comprises one or more alterations to increase half-life. ABPs with increased half-lives and improved binding to the neonatal Fc receptor (FcRn) are described, for example, in Hinton et al., *J. Immunol.,* 2006, 176:346-356; and U.S. Pat. No. 7,361,740; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an ABP provided herein comprises one or more Fc region variants as described in U.S. Pat. Nos. 7,371,826, 5,648,260, and 5,624,821; Duncan and Winter, *Nature,* 1988, 322:738-740; and WO 94/29351; each of which is incorporated by reference in its entirety.

1.2. Pyroglutamate

As is known in the art, both glutamate (E) and glutamine (Q) at the N-termini of recombinant proteins can cyclize spontaneously to form pyroglutamate (pE) in vitro and in vivo. See Liu et al., *J. Biol. Chem.,* 2011, 286:11211-11217, incorporated by reference in its entirety.

In some embodiments, provided herein are ABPs comprising a polypeptide sequence having a pE residue at the N-terminal position. In some embodiments, provided herein are ABPs comprising a polypeptide sequence in which the N-terminal residue has been converted from Q to pE. In some embodiments, provided herein are ABPs comprising a polypeptide sequence in which the N-terminal residue has been converted from E to pE.

In some embodiments, provided herein are ABPs comprising $V_H$ sequences having a pE residue at the N-terminal position. In some embodiments, provided herein are ABPs comprising a $V_H$ sequence in which the N-terminal residue has been converted from Q to pE. In some embodiments, provided herein is an ABP comprising a $V_H$ sequence selected from SEQ ID Nos:85-90, 97-99, wherein the N-terminal Q residue has been converted to pE. In some embodiments, provided herein is a composition comprising an ABP, wherein the ABP comprises a $V_H$ selected from SEQ ID NOs:85-90, 97-99, in which at least about 20%, at least about 40%, at least about 60%, at least about 80%, at least about 90%, at least about 95%, or at least about 99% of the N-terminal residues of such $V_H$ in such composition have been converted from Q to pE.

In some embodiments, provided herein are ABPs comprising $V_H$ sequences having a pE residue at the N-terminal position. In some embodiments, provided herein are ABPs comprising a $V_H$ sequence in which the N-terminal residue has been converted from E to pE. In some embodiments, provided herein is an ABP comprising a $V_H$ sequence selected from SEQ ID Nos:91-96, wherein the N-terminal E residue has been converted to pE. In some embodiments, provided herein is a composition comprising an ABP, wherein the ABP comprises a $V_H$ selected from SEQ ID NOs:91-96, in which at least about 20%, at least about 40%, at least about 60%, at least about 80%, at least about 90%, at least about 95%, or at least about 99% of the N-terminal residues of such $V_H$ in such composition have been converted from E to pE.

In some embodiments, provided herein are ABPs comprising $V_L$ sequences having a pE residue at the N-terminal position. In some embodiments, provided herein are ABPs comprising a $V_L$ sequence in which the N-terminal residue has been converted from E to pE. In some embodiments, provided herein is an ABP comprising a $V_L$ sequence set forth in SEQ ID No:120, wherein the N-terminal E residue has been converted to pE. In some embodiments, provided herein is a composition comprising an ABP, wherein the ABP comprises a $V_L$ set forth in SEQ ID NO:120, in which at least about 20%, at least about 40%, at least about 60%, at least about 80%, at least about 90%, at least about 95%, or at least about 99% of the N-terminal residues of such $V_L$ in such composition have been converted from E to pE.

In some embodiments, provided herein are ABPs comprising heavy chain sequences having a pE residue at the N-terminal position. In some embodiments, provided herein are ABPs comprising a heavy chain sequence in which the N-terminal residue has been converted from Q to pE. In some embodiments, provided herein is an ABP comprising a heavy chain sequence selected from SEQ ID Nos:107-112, 119-121, wherein the N-terminal Q residue has been converted to pE. In some embodiments, provided herein is a composition comprising an ABP, wherein the ABP comprises a heavy chain selected from SEQ ID NOs:107-112, 119-121, in which at least about 20%, at least about 40%, at least about 60%, at least about 80%, at least about 90%, at least about 95%, or at least about 99% of the N-terminal residues of such heavy chain in such composition have been converted from Q to pE.

In some embodiments, provided herein are ABPs comprising heavy chain sequences having a pE residue at the N-terminal position. In some embodiments, provided herein are ABPs comprising a heavy chain sequence in which the N-terminal residue has been converted from E to pE. In some embodiments, provided herein is an ABP comprising a heavy chain sequence selected from SEQ ID Nos:113-118, wherein the N-terminal E residue has been converted to pE. In some embodiments, provided herein is a composition comprising an ABP, wherein the ABP comprises a heavy chain selected from SEQ ID NOs:113-118, in which at least about 20%, at least about 40%, at least about 60%, at least about 80%, at least about 90%, at least about 95%, or at least about 99% of the N-terminal residues of such heavy chain in such composition have been converted from E to pE.

In some embodiments, provided herein are ABPs comprising light chain sequences having a pE residue at the N-terminal position. In some embodiments, provided herein are ABPs comprising a light chain sequence in which the N-terminal residue has been converted from E to pE. In some embodiments, provided herein is an ABP comprising a kappa light chain sequence selected from SEQ ID NOs: 124-125, wherein the N-terminal E residue has been converted to pE. In some embodiments, provided herein is a composition comprising an ABP, wherein the ABP comprises a kappa light chain selected from SEQ ID NOs:124-125, in which at least about 20%, at least about 40%, at least about 60%, at least about 80%, at least about 90%, at least about 95%, or at least about 99% of the N-terminal residues of such light chain in such composition have been converted from E to pE.

1.3. Cysteine Engineered Antigen-Binding Protein Variants

In certain embodiments, provided herein are cysteine engineered ABPs, also known as "thioMAbs," in which one or more residues of the ABP are substituted with cysteine residues. In particular embodiments, the substituted residues occur at solvent accessible sites of the ABP. By substituting such residues with cysteine, reactive thiol groups are introduced at solvent accessible sites of the ABP and may be used to conjugate the ABP to other moieties, such as drug moieties or linker-drug moieties, for example, to create an immunoconjugate.

In certain embodiments, any one or more of the following residues may be substituted with cysteine: V205 of the light chain; A118 of the heavy chain Fc region; and S400 of the heavy chain Fc region. Cysteine engineered ABPs may be generated as described, for example, in U.S. Pat. No. 7,521,541, which is incorporated by reference in its entirety.

2. Methods of Making NRP-1 Antigen-Binding Proteins 2.1. NRP-1 Antigen Preparation The NRP-1 antigen used for isolation of the ABPs provided herein may be intact NRP-1 or a fragment of NRP-1. The NRP-1 antigen may be, for example, in the form of an isolated protein or a protein expressed on the surface of a cell.

In some embodiments, the NRP-1 antigen is a non-naturally occurring variant of NRP-1, such as a NRP-1 protein having an amino acid sequence or post-translational modification that does not occur in nature.

In some embodiments, the NRP-1 antigen is truncated by removal of, for example, intracellular or membrane-spanning sequences, or signal sequences. In some embodiments, the NRP-1 antigen is fused at its C-terminus to a human IgG1 Fc domain or a polyhistidine tag.

2.2. Methods of Making Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* $3^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

In another aspect is provided a method for producing an anti-human NRP-1 antibody or an antigen-binding fragment thereof, comprising culturing host cell(s) selected from the group consisting of (a) to (c) below to express an anti-human NRP-1 antibody or an antigen-binding fragment thereof: (a) a host cell transformed with an expression vector comprising a polynucleotide comprising a base sequence encoding the heavy chain variable region of the anti-human NRP-1 antibody or the antigen-binding fragment thereof provided herein and a polynucleotide comprising a base sequence encoding the light chain variable region of the antibody or the antigen-binding fragment thereof; (b) a host cell transformed with an expression vector comprising a polynucleotide comprising a base sequence encoding the heavy chain variable region of the anti-human NRP-1 antibody or the antigen-binding fragment thereof provided herein and an expression vector comprising a polynucleotide comprising a base sequence encoding the light chain variable region of the antibody or the antigen-binding fragment thereof; and (c) a host cell transformed with an expression vector comprising a polynucleotide comprising a base sequence encoding the heavy chain variable region of the anti-human NRP-1 antibody or the antigen-binding fragment thereof provided herein and a host cell transformed with an expression vector comprising a polynucleotide comprising a base sequence encoding the light chain variable region of the antibody or the antigen-binding fragment thereof.

In another aspect is provided a method for producing an anti-human NRP-1 antibody, comprising culturing host cell (s) selected from the group consisting of (a) to (c) below to express an anti-human NRP-1 antibody: (a) a host cell transformed with an expression vector comprising a polynucleotide comprising a base sequence encoding the heavy chain of the anti-human NRP-1 antibody provided herein and a polynucleotide comprising a base sequence encoding the light chain of the antibody; (b) a host cell transformed with an expression vector comprising a polynucleotide comprising a base sequence encoding the heavy chain of the anti-human NRP-1 antibody provided herein and an expression vector comprising a polynucleotide comprising a base sequence encoding the light chain of the antibody; and (c) a host cell transformed with an expression vector comprising a polynucleotide comprising a base sequence encoding the heavy chain of the anti-human NRP-1 antibody provided herein and a host cell transformed with an expression vector comprising a polynucleotide comprising a base sequence encoding the light chain of the antibody.

2.3. Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

2.4. Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

2.5. Methods of Making Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573, 905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

2.6. Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., *Nat. Med.*, 2003, 9:129-134, incorporated by reference in its entirety. Methods of making scFv antibodies are described, for example, in Plückthun, in *The Pharmacology of Monoclonal Antibodies*, vol. 113, Rosenburg and Moore eds., Springer-Verlag, N.Y., pp. 269-315 (1994); WO 93/16185; and U.S. Pat. Nos. 5,571,894 and 5,587,458; each of which is incorporated by reference in its entirety.

2.7. Methods of Making Alternative Scaffolds

The alternative scaffolds provided herein may be made by any suitable method, including the illustrative methods described herein or those known in the art. For example, methods of preparing Adnectins™ are described in Emanuel et al., *mAbs*, 2011, 3:38-48, incorporated by reference in its entirety. Methods of preparing iMabs are described in U.S. Pat. Pub. No. 2003/0215914, incorporated by reference in its entirety. Methods of preparing Anticalins® are described in Vogt and Skerra, *Chem. Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, *Curr. Opinion in Biotech.*, 2004, 15:364-373, incorporated by reference in its entirety. Methods of preparing DARPins are provided in Zahnd et al., *J. Mol. Biol.*, 2007, 369:1015-1028, incorporated by reference in its entirety. Methods of preparing Affilins are provided in Ebersbach et al., *J. Mol. Biol.*, 2007, 372:172-185, incorporated by reference in its entirety. Methods of preparing Tetranectins are provided in Graversen et al., *J. Biol. Chem.*, 2000, 275:37390-37396, incorporated by reference in its entirety. Methods of preparing Avimers are provided in Silverman et al., *Nature* Biotech., 2005, 23:1556-1561, incorporated by reference in its entirety. Methods of preparing Fynomers are provided in Silacci et al., *J. Biol. Chem.*, 2014, 289:14392-14398, incorporated by reference in its entirety.

Further information on alternative scaffolds is provided in Binz et al., *Nat. Biotechnol.*, 2005 23:1257-1268; and Skerra, *Current Opin. in Biotech.*, 2007 18:295-304, each of which is incorporated by reference in its entirety.

2.8. Methods of Making Variants

In some embodiments, an ABP provided herein is an affinity matured variant of a parent ABP, which may be generated, for example, using phage display-based affinity maturation techniques. Briefly, one or more CDR residues may be mutated and the variant ABPs, or portions thereof, displayed on phage and screened for affinity. Such alterations may be made in CDR "hotspots," or residues encoded by codons that undergo mutation at high frequency during the somatic maturation process (see Chowdhury, *Methods Mol. Biol.*, 2008, 207:179-196, incorporated by reference in its entirety), and/or residues that contact the antigen.

Any suitable method can be used to introduce variability into a polynucleotide sequence(s) encoding an ABP, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify ABP variants with improved affinity. Affinity maturation by constructing and reselecting from secondary libraries has been described, for example, in Hoogenboom et al., *Methods in Molecular Biology*, 2001, 178:1-37, incorporated by reference in its entirety.

2.9. Vectors, Host Cells, and Recombinant Methods

Also provided are isolated nucleic acids encoding NRP-1 ABPs, vectors comprising the nucleic acids, and host cells comprising the vectors and nucleic acids, as well as recombinant techniques for the production of the ABPs.

In another aspect is provided a polynucleotide comprising a base sequence encoding the heavy chain variable region of the anti-human NRP-1 antibody or the antigen-binding fragment thereof provided herein. In another aspect is provided a polynucleotide comprising a base sequence encoding the light chain variable region of the anti-human NRP-1 antibody or the antigen-binding fragment thereof provided herein.

In another aspect is provided a polynucleotide comprising a base sequence encoding the heavy chain of the anti-human NRP-1 antibody provided herein. In another aspect is provided a polynucleotide comprising a base sequence encoding the light chain of the anti-human NRP-1 antibody provided herein.

For recombinant production of an ABP, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference herein in its entirety.

In another aspect is provided an expression vector comprising (a) a polynucleotide comprising a base sequence encoding the heavy chain variable region of the anti-human NRP-1 antibody or the antigen-binding fragment thereof provided herein and/or (b) a polynucleotide comprising a base sequence encoding the light chain variable region of the anti-human NRP-1 antibody or the antigen-binding fragment thereof.

In another aspect is provided an expression vector comprising (a) a polynucleotide comprising a base sequence encoding the heavy chain of the anti-human NRP-1 antibody provided herein and/or (b) a polynucleotide comprising a base sequence encoding the light chain of the anti-human NRP-1 antibody.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the ABPs provided herein.

In another aspect is provided a host cell transformed with an expression vector selected from the group consisting of (a) to (d): (a) a host cell transformed with an expression vector comprising a polynucleotide comprising a base sequence encoding the heavy chain variable region of the anti-human NRP-1 antibody or the antigen-binding fragment thereof provided herein, and a polynucleotide comprising a base sequence encoding the light chain variable region of the antibody or the antigen-binding fragment thereof; (b) a host cell transformed with an expression vector comprising a polynucleotide comprising a base sequence encoding the heavy chain variable region of the anti-human NRP-1 antibody or the antigen-biding fragment thereof provided herein and an expression vector comprising a polynucleotide comprising a base sequence encoding the light chain variable region of the antibody or the antigen-binding fragment thereof; (c) a host cell transformed with an expression vector comprising a polynucleotide comprising a base sequence encoding the heavy chain variable region of the anti-human NRP-1 antibody or the antigen-binding fragment thereof provided herein; and (d) a host cell transformed with an expression vector comprising a polynucleotide comprising a base sequence encoding the light chain variable region of the anti-human NRP-1 antibody or the antigen-binding fragment thereof provided herein.

In another aspect is provided host cell transformed with an expression vector selected from the group consisting of (a) to (d): (a) a host cell transformed with an expression vector comprising a polynucleotide comprising a base sequence encoding the heavy chain of the anti-human NRP-1 antibody provided herein and a polynucleotide comprising a base sequence encoding the light chain of the antibody; (b) a host cell transformed with an expression vector comprising a polynucleotide comprising a base sequence encoding the heavy chain of the anti-human NRP-1 antibody provided herein and an expression vector comprising a polynucleotide comprising a base sequence encoding the light chain of the antibody; (c) a host cell transformed with an expression vector comprising a polynucleotide comprising a base sequence encoding the heavy chain of the anti-human NRP-1 antibody provided herein; and (d) a host cell transformed with an expression vector comprising a polynucleotide comprising a base sequence encoding the light chain of the anti-human NRP-1 antibody provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for NRP-1 ABP-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltii, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

The host cells used to produce the NRP-1 ABPs disclosed herein may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.*, 1979, 58:44; Barnes et al., *Anal. Biochem.*, 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated herein by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the ABP can be produced intracellularly, in the periplasmic space, or directly secreted into the medium. If the ABP is produced intracellularly, as a first step, the particulate debris, either host cells or lysed fragments, is removed, for example, by centrifugation or ultrafiltration. For example, Carter et al. (*Bio/Technology*, 1992, 10:163-167, incorporated by reference in its entirety) describes a procedure for isolating ABPs which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the ABP is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the ABP may be useful, for example, where the ABP accumulates in a cell as an insoluble aggregate, or where yields from periplasmic expression are low.

Where the ABP is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The ABP composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the ABP. Protein A can be used to purify ABPs that comprise human γ1, γ2, or γ4 heavy chains (Lindmark et al., *J. Immunol. Meth.*, 1983, 62:1-13, incorporated by reference in its entirety). Protein G is useful for all mouse isotypes and for human γ3 (Guss et al., *EMBO J.*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the ABP comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the ABP of interest and contaminants may be subjected to low pH hydrophobic interaction chromatography using an elution buffer at a pH between about 2.5 to about 4.5, generally performed at low salt concentrations (e.g., from about 0 to about 0.25 M salt).

3. Assays

A variety of assays known in the art may be used to identify and characterize the NRP-1 ABPs provided herein.

3.1. Binding, Competition, and Epitope Mapping Assays

Specific antigen-binding activity of the ABPs provided herein may be evaluated by any suitable method, including using SPR, BLI, RIA, KinExA, flow cytometry, and MSD-SET. Additionally, antigen-binding activity may be evaluated by ELISA assays and western blot assays.

Assays for measuring competition between two ABPs, or an ABP and another molecule (e.g., one or more ligands of NRP-1) are described elsewhere in this disclosure and, for example, in Harlow and Lane, *Antibodies: A Laboratory Manual* ch.14, 1988, Cold Spring Harbor Laboratory, Cold Spring Harbor, N.Y., incorporated by reference in its entirety.

Assays for mapping the epitopes to which the ABPs provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

3.2. NRP-1 Antagonism Assays

In some embodiments, the ABPs provided herein are screened to identify or characterize ABPs with antagonistic activity against NRP-1. Any suitable assay may be used to identify or characterize such ABPs. In some aspects, the assay measures the amount of a cytokine secreted by an effector T cell after contacting the effector T cell with an ABP provided herein. In some aspects, the cytokine is selected from IL-2, IL-6, LT-α, TNF, GM-CSF, IFNγ, and combinations thereof. In some aspects, the cytokine is selected from sCD40L, VEGF, TGF-α, RANTES, PDGF-AB/BB, PDGF-AA, MIP-1β, MIP-1α, MDC (CCL22), MCP-3, MCP-1, IP-10, IL-17A, IL-2Rα, IL-15, IL-13, IL-12 (p70), IL-12 (p40), IL-10, IL-9, IL-8, IL-7, IL-5, IL-4, IL-3, IL-2, IL-2Rα, IL-1RA, IL-1β, IL-1α, IFNγ, IFNα2, GRO, GM-CSF, G-CSF, fractalkine, Flt-3 ligand, FGF-2, eotaxin, EGF, and combinations thereof.

In some embodiments, the effector cells are co-stimulated with an agonist of CD3, to promote the secretion of cytokines by the effector cell. In some aspects, the CD3 agonist is provided at a submaximal level.

In some aspects, such assays may measure the proliferation of an effector T cell after contacting the effector T cell with an ABP provided herein. In some aspects, proliferation of the effector T cell is measured by dilution of a dye (e.g., carboxyfluorescein diacetate succinimidyl ester; CFSE), by tritiated thymidine uptake, by luminescent cell viability assays, or by other assays known in the art.

In some aspects, such assays may measure the differentiation, cytokine production, viability (e.g., survival), proliferation, or suppressive activity of a regulatory T cell after contacting the regulatory T cell with an ABP provided herein.

In some aspects, such assays may measure the cytotoxic activity of an NK cell after contacting the NK cell with an ABP provided herein. In some aspects, the cytotoxic activity of the NK cell is measured using a cytotoxicity assay that quantifies NK-mediated killing of target cells (e.g., a K562 cell line). See Jang et al., *Ann. Clin. Lab. Sci.*, 2012, 42:42-49, incorporated by reference in its entirety.

In some aspects, such assays may measure the amount of granzyme B. In some aspects, such assays may measure the amount of perforin.

3.3. Assays for Effector Functions

Effector function following treatment with the ABPs provided herein may be evaluated using a variety of in vitro and in vivo assays known in the art, including those described in Ravetch and Kinet, *Annu. Rev. Immunol.*, 1991, 9:457-492; U.S. Pat. Nos. 5,500,362, 5,821,337; Hellstrom et al., *Proc. Nat'l Acad. Sci. USA,* 1986, 83:7059-7063; Hellstrom et al., *Proc. Nat'l Acad. Sci. USA,* 1985, 82:1499-1502; Bruggemann et al., *J. Exp. Med.,* 1987, 166:1351-1361; Clynes et al., *Proc. Nat'l Acad. Sci. USA,* 1998, 95:652-656; WO 2006/029879; WO 2005/100402; Gazzano-Santoro et al., *J. Immunol. Methods,* 1996, 202:163-171; Cragg et al., *Blood,* 2003, 101:1045-1052; Cragg et al. *Blood,* 2004, 103:2738-2743; and Petkova et al., *Int'l. Immunol.,* 2006, 18:1759-1769; each of which is incorporated by reference in its entirety.

4. Pharmaceutical Compositions

The ABPs provided herein can be formulated in any appropriate pharmaceutical composition and administered by any suitable route of administration. Suitable routes of administration include, but are not limited to, the intraarterial, intradermal, intramuscular, intraperitoneal, intravenous, nasal, parenteral, pulmonary, and subcutaneous routes.

In another aspect is provided a pharmaceutical composition comprising an anti-human NRP-1 antibody or an antigen-binding fragment thereof provided herein and pharmaceutically acceptable excipients.

In another aspect is provided a pharmaceutical composition comprising plural kinds of anti-human NRP-1 antibodies or antigen-binding fragments thereof provided herein. For example, the pharmaceutical composition comprises an antibody or an antigen-binding fragment thereof, which does not undergo posttranslational modification and an antibody or an antigen-binding fragment thereof derived from posttranslational modification of the antibody or the antigen-binding fragment thereof.

In one embodiment, the pharmaceutical composition comprises at least two kinds of anti-human NRP-1 antibodies selected from (1) to (4): (1) an anti-human NRP-1 antibody comprising a heavy chain consisting of SEQ ID NO:118, and a light chain consisting of SEQ ID NO:126, (2) an anti-human NRP-1 antibody comprising a heavy chain consisting of SEQ ID NO: 118 in which E of the amino acid number 1 is modified to pyroglutamate, and a light chain consisting of SEQ ID NO:126, (3) an anti-human NRP-1 antibody comprising a heavy chain consisting of the amino acid sequence of amino acid numbers 1 to 453 of SEQ ID NO:118, and a light chain consisting of SEQ ID NO:126; and (4) an anti-human NRP-1 antibody comprising a heavy chain consisting of the amino acid sequence of amino acid numbers 1 to 453 of SEQ ID NO:118 in which E of the amino acid number 1 is modified to pyroglutamate, and a light chain consisting of SEQ ID NO:126.

In one embodiment, the pharmaceutical composition comprises an anti-human NRP-1 antibody comprising a heavy chain consisting of SEQ ID NO:118, and a light chain consisting of SEQ ID NO:126, an anti-human NRP-1 antibody comprising a heavy chain consisting of the amino acid sequence of amino acid numbers 1 to 453 of SEQ ID NO:118, and a light chain consisting of SEQ ID NO:126, and a pharmaceutically acceptable excipient.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a cosolvent. Illustrative examples of cosolvents include ethanol, poly(ethylene) glycol, butylene glycol, dimethylacetamide, glycerin, propylene glycol, and combinations thereof.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, monosodium glutamate, and combinations thereof.

In some embodiments, the pharmaceutical composition comprises a carrier or filler. Illustrative examples of carriers or fillers include lactose, maltodextrin, mannitol, sorbitol, chitosan, stearic acid, xanthan gum, guar gum, and combinations thereof.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, vitamin E polyethylene(glycol) succinate, and combinations thereof.

In some embodiments, the pharmaceutical composition comprises an anti-caking agent. Illustrative examples of anti-caking agents include calcium phosphate (tribasic), hydroxymethyl cellulose, hydroxypropyl cellulose, magnesium oxide, and combinations thereof.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, sugars, and combinations thereof. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an ABP, since water can facilitate the degradation of some ABPs.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

4.1. Parenteral Dosage Forms

In certain embodiments, the ABPs provided herein are formulated as parenteral dosage forms. Parenteral dosage forms can be administered to subjects by various routes including, but not limited to, subcutaneous, intravenous (including infusions and bolus injections), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the ABPs disclosed herein can also be incorporated into the parenteral dosage forms.

In some embodiments, the parenteral dosage form is lyophilized. Exemplary lyophilized formulations are described, for example, in U.S. Pat. Nos. 6,267,958 and 6,171,586; and WO 2006/044908; each of which is incorporated by reference in its entirety.

5. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic ABPs.

The amount of the ABP or composition which will be effective in the prevention or treatment of a disorder or one or more symptoms thereof will vary with the nature and severity of the disease or condition, and the route by which the ABP is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the ABP per kilogram of subject or sample weight (e.g., about 10 micrograms per kilogram to about 50 milligrams per kilogram, about 100 micrograms per kilogram to about 25 milligrams per kilogram, or about 100 micrograms per kilogram to about 10 milligrams per kilogram). In certain embodiment, the dosage of the ABP provided herein, based on weight of the ABP, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, 15 mg/kg, 20 mg/kg, 25 mg/kg, 30 mg/kg, 40 mg/kg, or more of a subject's body weight. It may be necessary to use dosages of the ABP outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the ABPs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an ABP or composition provided herein followed by one or more maintenance doses.

In certain embodiments, a dose of an ABP or composition provided herein can be administered to achieve a steady-state concentration of the ABP in blood or serum of the subject. The steady-state concentration can be determined by measurement according to techniques available to those of skill or can be based on the physical characteristics of the subject such as height, weight and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same composition may be repeated and the composition may be given once weekly, once every two weeks, once every three weeks, or once every four weeks. In certain embodiments, the first dose administered to the patient may be a "loading dose." A loading dose may be a higher dose than subsequent doses.

As discussed in more detail elsewhere in this disclosure, an ABP provided herein may optionally be administered with one or more additional agents useful to prevent or treat a disease or disorder. The effective amount of such additional agents may depend on the amount of ABP present in the formulation, the type of disorder or treatment, and the other factors known in the art or described herein.

6. Therapeutic Applications

For therapeutic applications, the ABPs of the invention are administered to a mammal, generally a human, in a pharmaceutically acceptable dosage form such as those known in the art and those discussed above. For example, the ABPs of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The ABPs also are suitably administered by peritumoral, intralesional, or perilesional routes, to exert local as well as systemic therapeutic effects. The intraperitoneal route may be particularly useful, for example, in the treatment of ovarian tumors.

The ABPs provided herein may be useful for the treatment of any disease or condition involving NRP-1. In some embodiments, the disease or condition is a disease or condition that can benefit from treatment with an anti-NRP-1 ABP. In some embodiments, the disease or condition is a tumor. In some embodiments, the disease or condition is a cell proliferative disorder. In some embodiments, the disease or condition is a cancer.

In some embodiments, the ABPs provided herein are provided for use as a medicament. In some embodiments, the ABPs provided herein are provided for use in the manufacture or preparation of a medicament. In some embodiments, the medicament is for the treatment of a disease or condition that can benefit from an anti-NRP-1 ABP. In some embodiments, the disease or condition is a tumor. In some embodiments, the disease or condition is a cell proliferative disorder. In some embodiments, the disease or condition is a cancer. In some embodiments, the disease or condition is a viral infection.

In some embodiments, provided herein is a method of treating a disease or condition in a subject in need thereof by administering an effective amount of an ABP provided herein to the subject. In some aspects, the disease or condition is a cancer. In some aspects, the disease or condition is a viral infection.

Any suitable cancer may be treated with the ABPs provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, provided herein is a method of antagonizing NRP-1 in a target cell of a subject in need thereof by administering an effective amount of an ABP provided herein to the subject. In some aspects, antagonism of NRP-1 by an ABP provided herein results in increased secretion of IL-2, LT-α, IL-6, TNF, GM-CSF, IFNγ or combinations thereof by a target cell.

In some embodiments, provided herein is a method of increasing the proliferation, survival, and/or function of an effector T cell in a subject in need thereof by administering an effective amount of an ABP provided herein to the subject. In some aspects, the effector T cell is a CD4+ effector T cell. In some aspects, the effector T cell is a CD8+ effector T cell.

In some embodiments, provided herein is a method of abrogating suppression of an effector T cell by a regulatory T cell in a subject in need thereof by administering an effective amount of an ABP provided herein to the subject. In some aspects, the regulatory T cell is a CD4+CD25+ Foxp3+ regulator T cell. In some aspects, the regulatory T cell is a CD8+CD25+ regulatory T cell.

In some embodiments, provided herein is a method of increasing the activity of a natural killer (NK) cell, a natural killer T (NKT) cell, a macrophage, or a dendritic cell (e.g., a plasmacytoid dendritic cell) in a subject in need thereof by administering an effective amount of an ABP provided herein to the subject.

In some embodiments, provided herein is a method of treating a subject having a cancer without concomitant platelet reduction. In some aspects, the method does not result in a substantive amount of thrombocytopenia in the subject.

In some embodiments, provided herein is a method of enhancing an immune response in a subject in need thereof by administering an effective amount of an ABP provided herein to the subject.

In some embodiments, provided herein is a method delaying the onset of a tumor in a subject in need thereof by administering an effective amount of an ABP provided herein to the subject.

In some embodiments, provided herein is a method preventing the onset of a tumor in a subject in need thereof by administering an effective amount of an ABP provided herein to the subject.

In some embodiments, provided herein is a method of delaying the onset of a cancer in a subject in need thereof by administering an effective amount of an ABP provided herein to the subject.

In some embodiments, provided herein is a method of preventing the onset of a cancer in a subject in need thereof by administering an effective amount of an ABP provided herein to the subject.

In some embodiments, provided herein is a method of reducing the size of a tumor in a subject in need thereof by administering an effective amount of an ABP provided herein to the subject.

In some embodiments, provided herein is a method of reducing the number of metastases in a subject in need thereof by administering an effective amount of an ABP provided herein to the subject.

In some embodiments, provided herein is a method of reducing viral titer a subject in need thereof by administering an effective amount of an ABP provided herein to the subject.

In some embodiments, provided herein is a method for extending the period of overall survival, median survival time, or progression-free survival in a subject in need thereof by administering an effective amount of an ABP provided herein to the subject.

In some embodiments, provided herein is a method for treating a subject who has become resistant to a standard of care therapeutic by administering an effective amount of an ABP provided herein to the subject. In some embodiments, the standard-of-care therapeutic to which the subject has become resistant is a PD-1 inhibitor. In other embodiments, the standard-of-care therapeutic to which the subject has become resistant is a PD-L1 inhibitor. In other embodiments, the standard-of-care therapeutic to which the subject has become resistant is a CTLA-4 inhibitor.

7. Combination Therapies

In some embodiments, an ABP provided herein is administered with at least one additional therapeutic agent. Any suitable additional therapeutic agent may be administered with an ABP provided herein. In some aspects, the additional therapeutic agent is selected from radiation, a cytotoxic agent, a chemotherapeutic agent, a cytostatic agent, an anti-hormonal agent, an EGFR inhibitor, an immunostimulatory agent, an anti-angiogenic agent, and combinations thereof.

In some embodiments, the additional therapeutic agent comprises an immunostimulatory agent.

In some embodiments, the immunostimulatory agent is an agent that blocks signaling of an inhibitory receptor of an immune cell, or a ligand thereof. In some aspects, the inhibitory receptor or ligand is selected from PVRIG, VISTA, CCR4, CD27, CTLA-4, PD-1, PD-L1, LAG-3, Tim3, TIGIT, neuritin, BTLA, KIR, and combinations thereof. In some aspects, the agent is selected from an anti-PD-1 antibody (e.g., pembrolizumab or nivolumab), and anti-PD-L1 antibody (e.g., atezolizumab), an anti-CTLA-4 antibody (e.g., ipilimumab), and combinations thereof. In some aspects, the agent is pembrolizumab. In some aspects, the agent is nivolumab. In some aspects, the agent is atezolizumab.

In some embodiments, the additional therapeutic agent is an agent that inhibits the interaction between PD-1 and PD-L1. In some aspects, the additional therapeutic agent that inhibits the interaction between PD-1 and PD-L1 is selected from an antibody, a peptidomimetic and a small molecule. In some aspects, the additional therapeutic agent that inhibits the interaction between PD-1 and PD-L1 is selected from pembrolizumab, nivolumab, atezolizumab, avelumab, durvalumab, BMS-936559, sulfamonomethoxine 1, and sulfamethizole 2. In some embodiments, the additional therapeutic agent that inhibits the interaction between PD-1 and PD-L1 is any therapeutic known in the art to have such activity, for example as described in Weinmann et al., *Chem Med Chem*, 2016, 14:1576 (DOI: 10.1002/cmdc.201500566), incorporated by reference in its entirety.

In some embodiments, the agent that inhibits the interaction between PD-1 and PD-L1 is formulated in the same pharmaceutical composition an ABP provided herein. In some embodiments, the agent that inhibits the interaction between PD-1 and PD-L1 is formulated in a different pharmaceutical composition from an ABP provided herein. In some embodiments, the agent that inhibits the interaction between PD-1 and PD-L1 is administered prior to administration of an ABP provided herein. In some embodiments, the agent that inhibits the interaction between PD-1 and PD-L1 is administered after administration of an ABP provided herein. In some embodiments, the agent that inhibits the interaction between PD-1 and PD-L1 is administered contemporaneously with an ABP provided herein, but the agent and ABP are administered in separate pharmaceutical compositions.

In some embodiments, the immunostimulatory agent is an agent that, when administered alone and at its recommended dosage, results in a certain amount of thrombocytopenia in the subject. In some aspects, such an agent may be administered in combination with an ABP provided herein at a reduced dosage. Such combination therapy may be safely administered without resulting in substantive platelet deterioration or thrombocytopenia.

In some embodiments, the immunostimulatory agent is an agonist of a co-stimulatory receptor of an immune cell. In some aspects, the co-stimulatory receptor is selected from OX40, ICOS, CD28, CD37, GITR, CD40, and 4-1BB, and combinations thereof. In some embodiments, the agonist is an antibody.

In some embodiments, the immunostimulatory agent is a cytokine. In some aspects, the cytokine is selected from IL-2, IL-5, IL-7, IL-12, IL-15, IL-21, and combinations thereof.

In some embodiments, the immunostimulatory agent is an oncolytic virus. In some aspects, the oncolytic virus is selected from a herpes simplex virus, a vesicular stomatitis virus, an adenovirus, a Newcastle disease virus, a vaccinia virus, and a maraba virus.

In some embodiments, the immunostimulatory agent is a T cell with a chimeric antigen receptor (CAR-T cell). In some embodiments, the immunostimulatory agent is a bi- or multi-specific T cell-directed antibody. In some embodiments, the immunostimulatory agent is an anti-TGF-β antibody. In some embodiments, the immunostimulatory agent is a TGF-β trap.

In some embodiments, the additional therapeutic agent is a vaccine to a tumor antigen. Any suitable antigen may be targeted by the vaccine, provided that it is present in a tumor treated by the methods provided herein. In some aspects, the tumor antigen is a tumor antigen that is overexpressed in comparison its expression levels in normal tissue. In some aspects, the tumor antigen is selected from cancer testis antigen, differentiation antigen, NY-ESO-1, MAGE-A1, MART, and combinations thereof.

Further examples of additional therapeutic agents include a taxane (e.g., paclitaxel or docetaxel); a platinum agent (e.g., carboplatin, oxaliplatin, and/or cisplatin); a topoisomerase inhibitor (e.g., irinotecan, topotecan, etoposide, and/or mitoxantrone); folinic acid (e.g., leucovorin); or a nucleoside metabolic inhibitor (e.g., fluorouracil, capecitabine, and/or gemcitabine). In some embodiments, the additional therapeutic agent is folinic acid, 5-fluorouracil, and/or oxaliplatin. In some embodiments, the additional therapeutic agent is 5-fluorouracil and irinotecan. In some embodiments, the additional therapeutic agent is a taxane and a platinum agent. In some embodiments, the additional therapeutic agent is paclitaxel and carboplatin. In some embodiments, the additional therapeutic agent is pemetrexate. In some embodiments, the additional therapeutic agent is a targeted therapeutic such as an EGFR, RAF or MEK-targeted agent.

The additional therapeutic agent may be administered by any suitable means. In some embodiments, an ABP provided herein and the additional therapeutic agent are included in the same pharmaceutical composition. In some embodiments, an ABP provided herein and the additional therapeutic agent are included in different pharmaceutical compositions.

In embodiments where an ABP provided herein and the additional therapeutic agent are included in different pharmaceutical compositions, administration of the ABP can occur prior to, simultaneously, and/or following, administration of the additional therapeutic agent. In some aspects, administration of an ABP provided herein and the additional therapeutic agent occur within about one month of each other. In some aspects, administration of an ABP provided herein and the additional therapeutic agent occur within about one week of each other. In some aspects, administration of an ABP provided herein and the additional therapeutic agent occur within about one day of each other. In some aspects, administration of an ABP provided herein and the additional therapeutic agent occur within about twelve hours of each other. In some aspects, administration of an ABP provided herein and the additional therapeutic agent occur within about one hour of each other.

8. Kits

Also provided are kits comprising the ABPs provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an ABP provided herein. The label or package insert indicates that the composition is used for treating the selected condition.

In some embodiments, the kit comprises (a) a first container with a first composition contained therein, wherein the first composition comprises an ABP provided herein; and (b) a second container with a second composition contained therein, wherein the second composition comprises a further therapeutic agent. The kit in this embodiment of the invention may further comprise a package insert indicating that the compositions can be used to treat a particular condition.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

EXAMPLES

The following are examples of methods and compositions of the invention. It is understood that various other embodiments may be practiced, given the general description provided herein.

Example 1

Antibody Selection

Materials and Methods

Antigens were biotinylated using the EZ-Link Sulfo-NHS-Biotinylation Kit from Pierce. Goat F(ab')$_2$ anti-human kappa-FITC (LC-FITC), ExtrAvidin-PE (EA-PE) and Streptavidin-AF633 (SA-633) were obtained from Southern Biotech, Sigma, and Molecular Probes, respectively. Streptavidin MicroBeads and MACS LC separation columns were purchased from Miltenyi Biotec. Goat anti-human IgG-PE (Human-PE) was obtained from Southern Biotech.

Naïve Discovery

Eight naïve human synthetic yeast libraries each of ~$10^9$ diversity were propagated as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013); WO2009036379; WO2010105256; and WO2012009568.) For the first two rounds of selection, a magnetic bead sorting technique utilizing the Miltenyi MACS system was performed, as previously described (see, e.g., Siegel et al, High efficiency recovery and epitope-specific sorting of an scFv yeast display library." *J Immunol Methods* 286(1-2), 141-153 (2004).) Briefly, yeast cells (~$10^{10}$ cells/library) were incubated with 5 ml of 100 nM biotinylated antigen for 30 min at 30° C. in wash buffer (phosphate-buffered saline (PBS)/0.1% bovine serum albumin (BSA)). After washing once with 40 ml ice-cold wash buffer, the cell pellet was resuspended in 20 mL wash buffer, and Streptavidin MicroBeads (500 µl) were added to the yeast and incubated for 15 min at 4° C. Next, the yeast were pelleted, resuspended in 20 mL wash buffer, and loaded onto a Miltenyi LS column. After the 20 mL were loaded, the column was washed 3 times with 3 ml wash buffer. The column was then removed from the magnetic field, and the yeast were eluted with 5 mL of growth media and then grown overnight. The following rounds of selection were performed using flow cytometry. Approximately 2×$10^7$ yeast were pelleted, washed three times with wash buffer, and incubated at 30° C. with either decreasing concentrations of biotinylated antigen (100 to 1 nM) under equilibrium conditions, 100 nM biotinylated antigens of different species in order to obtain species cross-reactivity, or with a polyspecificity depletion reagent (PSR) to remove non-specific antibodies from the selection. For the PSR depletion, the libraries were incubated with a 1:10 dilution of biotinylated PSR reagent as previously described (see, e.g., Y. Xu et al, Addressing polyspecificity of antibodies selected from an in vitro yeast presentation system: a FACS-based, high-throughput selection and analytical tool. *PEDS* 26.10, 663-70 (2013).) Yeast were then washed twice with wash buffer and stained with LC-FITC (diluted 1:100) and either SA-633 (diluted 1:500) or EAPE (diluted 1:50) secondary reagents for 15 min at 4° C. After washing twice with wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Antibody Optimization

Optimization of antibodies was performed via a light chain diversification protocol, and then by introducing diversities into the heavy chain and light chain variable regions as described below. A combination of some of these approaches was used for each antibody.

Light chain batch diversification protocol: Heavy chain plasmids from a naïve selection output were extracted from the yeast via smash and grab, propagated in and subsequently purified from *E. coli*, and transformed into a light chain library with a diversity of 5×$10^6$. Selections were performed with one round of MACS and four rounds of FACS employing the same conditions as the naïve discovery.

CDRH1 and CDRH2 selection: The CDRH3 of a single antibody was recombined into a premade library with CDRH1 and CDRH2 variants of a diversity of 1×$10^8$ and selections were performed with one round of MACS and four rounds of FACS as described in the naïve discovery. For each FACS round the libraries were looked at for PSR binding, species cross-reactivity, and affinity pressure, and sorting was performed in order to obtain a population with the desired characteristics.

$V_H$ Mutant selection: The heavy chain variable region ($V_H$) was mutagenized via error prone PCR. The library was then created by transforming this mutagenized $V_H$ and the heavy chain expression vector into yeast already containing the light chain plasmid of the parent. Selections were performed similar to previous cycles using FACS sorting for two rounds. For each FACS round the libraries were looked at for PSR binding, species cross-reactivity, and affinity pressure, and sorting was performed in order to obtain a population with the desired characteristics.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over KappaSelect® (GE Healthcare LifeSciences).

ForteBio $K_D$ Measurements

ForteBio affinity measurements were performed on an Octet RED384 generally as previously described (see, e.g., Estep et al, High throughput solution-based measurement of antibody-antigen affinity and epitope binning. *Mabs* 5(2), 270-278 (2013)). Briefly, ForteBio affinity measurements were performed by loading IgGs on-line onto AHQ sensors. Sensors were equilibrated off-line in assay buffer for 30 min and then monitored on-line for 60 seconds for baseline establishment. Sensors with loaded IgGs were exposed to 100 nM antigen for 3 minutes, and afterwards were transferred to assay buffer for 3 min for off-rate measurement. For monovalent affinity assessment Fabs were used instead of IgGs. For this assessment, the unbiotinylated Fc fusion antigen was loaded on-line onto the AHQ sensors. Sensors were equilibrated off-line in assay buffer for 30 min and then monitored on-line for 60 seconds for baseline establishment. Sensors with loaded antigen were exposed to 200 nM Fab for 3 minutes, and afterwards they were transferred to assay buffer for 3 min for off-rate measurement. All kinetics were analyzed using the 1:1 binding model.

ForteBio Epitope Binning/Ligand Blocking

Epitope binning/ligand blocking was performed using a standard sandwich format cross-blocking assay. Control anti-target IgG was loaded onto AHQ sensors and unoccupied Fc-binding sites on the sensor were blocked with an irrelevant human IgG1 antibody. The sensors were then exposed to 100 nM target antigen followed by a second anti-target antibody or ligand. Additional binding by the second antibody or ligand after antigen association indicates an unoccupied epitope (non-competitor), while no binding indicates epitope blocking (competitor or ligand blocking).

Size Exclusion Chromatography

A TSKgel® SuperSW mAb HTP column (22855) was used for fast SEC analysis of mammalian produced mAbs at 0.4 mL/min with a cycle time of 6 min/run. 200 mM Sodium Phosphate and 250 mM Sodium Chloride was used as the mobile phase.

Dynamic Scanning Fluorimetry

10 μL of 20× Sypro Orange is added to 20 μL of 0.2-1 mg/mL mAb or Fab solution. A RT-PCR instrument (BioRad CFX96 RT PCR) is used to ramp the sample plate temperature from 40 to 95 C at 0.5 C increment, with 2 min equilibrate at each temperature. The negative of first derivative for the raw data is used to extract Tm.

Example 2

Antibody Characterization

ForteBio $K_D$ Measurements: Quantitative binding of antibodies to recombinant monomeric human, mouse, or cynomolgus monkey NRP-1 was measured using biolayer interferometry (BLI) using FORTEBIO®. Affinity measurements of selected antibodies were performed generally as described in Estep et al., Mabs, 2013, 5:270-278, incorporated by reference in its entirety. FORTEBIO affinity measurements were performed by loading IgGs (human IgG1 N297A) on-line onto AHQ sensors. Sensors were equilibrated off-line in assay buffer for 30 min and then monitored on-line for 60 seconds for baseline establishment. Sensors with loaded IgGs were exposed to a single concentration of antigen (100 nM) for 3 minutes. Afterwards they were transferred to assay buffer for 3 minutes for off-rate measurement. Kinetics were analyzed using the 1:1 binding model. A summary of $K_D$ measurements for antibodies binding a single concentration of human, cynomolgus monkey, and mouse NRP-1 is shown in Table 5 below.

Additional $K_D$ measurements were performed with eight antibodies (human IgG4 S228P) using multi-concentration kinetics. The binding affinities for human NRP-1-His, cynomolgus monkey NRP-1-His, and mouse NRP-1-His were measured using an Octet QKe instrument (ForteBio). A strategy of capturing antibodies on sensors followed by association/dissociation of monomeric NRP-1 proteins was used to avoid avidity effects in the assay. The BLI analysis was performed at 30° C. using 1× kinetics buffer (ForteBio) as assay buffer. Anti-Human IgG Fc Capture (AHC) biosensors (ForteBio) were first presoaked in assay buffer for greater than 5 minutes. Test antibody (5 μg/mL) was captured on the sensor for 250 seconds. Sensors were then dipped in assay buffer for 60 seconds to establish a baseline before measuring binding to each NRP-1 protein. Sensors were then dipped into varying concentrations of human NRP-1-His (93.3 to 0.7 nM, 2-fold dilutions in assay buffer), cynomolgus monkey NRP-1-His (93.3 to 1.5 nM, 2-fold dilutions in assay buffer), or mouse NRP-1-His (93.3 to 1.5 nM, 2-fold dilutions in assay buffer) for 250 seconds to measure association. Dissociation of NRP-1 was then measured by dipping sensors into assay buffer for 600 seconds. Agitation at all steps was 1000 rpm. Kinetic parameters were generated with Octet Data Analysis Software Version 8.2.0.7 using reference subtraction (antibody "binding" to buffer), dissociation based inter-step correction, 1 to 1 binding model, and global fit (Rmax unlinked by sensor). $K_D$ values are shown in Table 6.

MSD-SET $K_D$ Measurements: Solution equilibrium affinity measurements of selected antibodies binding human NRP-1 were performed generally as previously described. See Estep et al., supra, incorporated by reference in its entirety. Briefly, solution equilibrium titrations (SET) were performed in PBS+0.1% IgG-Free BSA (PBSF) with antigen held constant at 10-100 pM and incubated with 3- to 5-fold serial dilutions of Fab or mAbs starting at 10 pM-10 nM. Antibodies (20 nM in PBS) were coated onto standard bind MSD-ECL plates overnight at 4° C. or at room temperature for 30 min. Plates were then blocked by BSA for 30 min with shaking at 700 rpm, followed by three washes with wash buffer (PBSF+0.05% Tween® 20). SET samples were applied and incubated on the plates for 150s with shaking at 700 rpm followed by one wash. Antigen captured on a plate was detected with 250 ng/mL sulfotag-labeled streptavidin in PBSF by incubation on the plate for 3 min. The plates were washed three times with wash buffer and then read on the MSD Sector Imager 2400 instrument using 1× Read Buffer T with surfactant. The percent free antigen was plotted as a function of titrated antibody in Prism and fit to a quadratic equation to extract the $K_D$. To improve throughput, liquid handling robots were used throughout MSD-SET experiments, including SET sample preparation.

TABLE 5

Antibody Binding Affinities - Single Concentration Kinetics

| MAB | ForteBio IgG $K_D$ Human NRP-1 His (M) Monovalent | ForteBio IgG $K_D$ Cyno NRP-1 His (M) Monovalent | ForteBio IgG $K_D$ Mouse NRP-1 His (M) Monovalent | MSD Fab $K_D$ Human NRP-1 His (M) Monovalent |
|---|---|---|---|---|
| 1 | 1.87E−09 | 2.16E−09 | 2.12E−09 | 3.20E−10 |
| 2 | 1.86E−09 | 2.43E−09 | 1.94E−09 | 2.30E−10 |
| 3 | 1.08E−09 | 1.19E−09 | 9.90E−10 | 6.00E−11 |
| 4 | 8.51E−10 | 9.25E−10 | 7.46E−10 | 4.60E−11 |
| 5 | 3.23E−09 | 4.09E−09 | 5.06E−09 | 2.80E−10 |
| 6 | 4.72E−09 | 5.54E−09 | 6.98E−09 | 4.50E−10 |
| 7 | 1.12E−08 | 1.09E−08 | 1.47E−08 | N.D. |
| 8 | 6.13E−10 | 6.42E−10 | 5.52E−10 | 9.60E−11 |
| 9 | 6.45E−10 | 6.43E−10 | 5.66E−10 | 1.90E−11 |
| 10 | 8.68E−10 | 8.66E−10 | 7.46E−10 | 6.40E−11 |
| 11 | 4.85E−10 | 4.80E−10 | 4.46E−10 | 2.10E−11 |
| 12 | 4.81E−10 | 4.69E−10 | 4.40E−10 | 2.60E−11 |
| 13 | 1.41E−09 | 1.58E−09 | 7.42E−09 | 5.40E−10 |
| 14 | 1.12E−09 | 1.10E−09 | 5.00E−09 | 2.80E−10 |
| 15 | 8.51E−10 | 9.20E−09 | 5.41E−08 | 1.80E−10 |

TABLE 6

Antibody Binding Affinities - Multiple Concentration Kinetics

| MAB | ForteBio IgG $K_D$ Human NRP-1 His (M) Monovalent | ForteBio IgG $K_D$ Cyno NRP-1 His (M) Monovalent | ForteBio IgG $K_D$ Mouse NRP-1 His (M) Monovalent |
|---|---|---|---|
| MAB2 I111T* IgG4 S228P | 2.8E−09 | 5.5E−09 | 4.6E−09 |
| MAB2 IgG4 S228P | 2.4E−09 | 4.5E−09 | 5.1E−09 |
| MAB3 IgG4 S228P | 3.7E−09 | 7.3E−09 | 4.4E−09 |
| MAB4 IgG4 S228P | 3.1E−09 | 4.5E−09 | 2.3E−09 |
| MAB5 IgG4 S228P | 8.4E−09 | 1.2E−08 | 6.6E−09 |
| MAB12 IgG4 S228P | 1.2E−10 | 1.9E−10 | 1.6E−10 |
| MAB13 IgG4 S228P | 9.6E−10 | 9.4E−10 | 3.7E−09 |
| MAB14 IgG4 S228P | 8.7E−10 | 7.4E−10 | 2.7E−09 |

Example 3

Figure 1B:
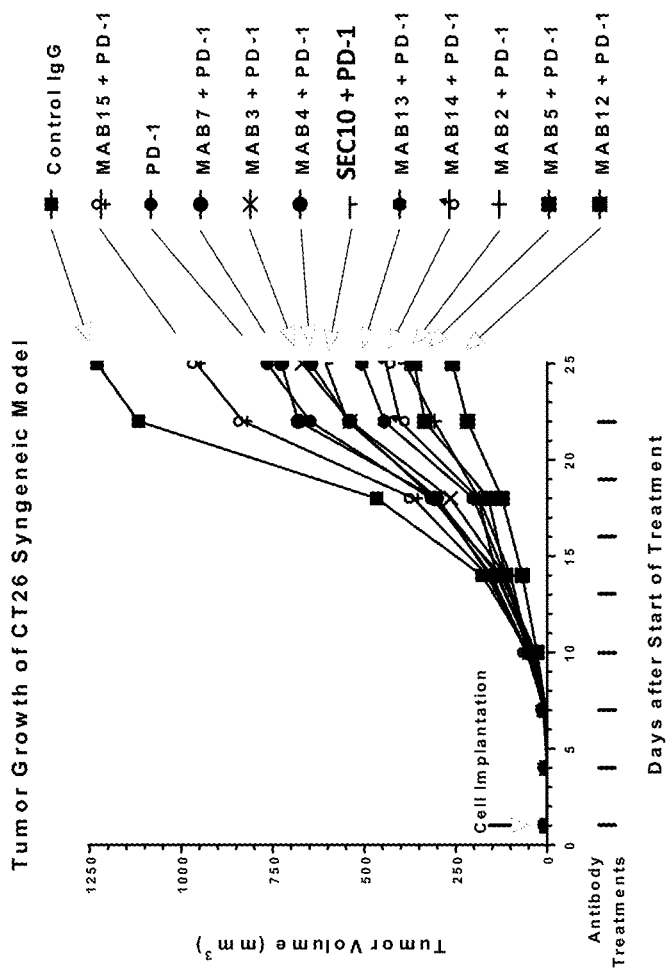
FIG. 1B is graphs showing tumor growth inhibition in CT26 tumor-bearing mice treated with a murine version of MABs 2, 3, 4, 5, 7, 12, 13, 14, and 15, as well as an IgG control and the anti-NRP-1 antibody SEC10 as a comparator. Mice were treated with MAB in combination with a PD-1 antibody (FIG. 1B). Antibody treatment times (days) are shown by arrows.

Anti-Tumor Efficacy of Nine Anti-NRP-1 MABs Alone and in Combination with a PD-1 or PD-L1 Antibody Nine optimized antibodies were evaluated for anti-tumor efficacy using immunocompetent mice. The assay was conducted with a panel of murine versions of MABs 2, 3, 4, 5, 7, 12, 13, 14, and 15, as well as an IgG control and SEC10 (SEQ ID NOS 141-142) as a comparator. The antibodies were tested as chimeric mouse IgG2a antibodies containing the N297A mutation which abolishes ADCC and CDC effector functions. Anti-tumor efficacy was measured using the mouse colon CT26 syngeneic tumor model grown in female BALB/c mice. $3 \times 10^5$ mouse CT26 cells were implanted subcutaneously on Day 1. The mice were randomized based on body weight and antibodies were administered intraperitoneally at the indicated dose on the same day as tumor cell implantation. The anti-NRP-1 antibodies were administered as a monotherapy at 500 μg/dose or in combination with an anti-PD-1 immune checkpoint inhibitor which was used at 200 μg/dose. FIG. 1A shows the monotherapy effect of antibodies in the CT26 model, and FIG. 1B shows the effect of combination of anti-NRP-1 antibodies with anti-PD-1. The black arrows along the horizontal axis indicate the treatment days of the antibodies. The average tumor volume from 10 mice per group is shown for each treatment group.

Figure 1C:
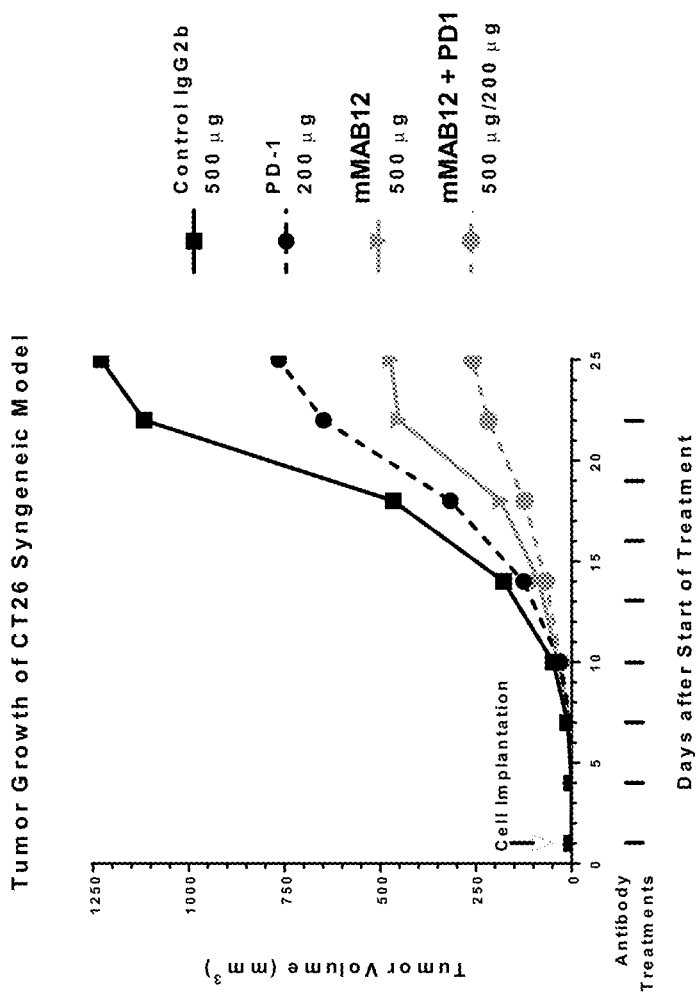
FIG. 1C is a graph showing tumor growth inhibition in CT26 tumor-bearing mice treated with monotherapy and combination therapy as described herein. Provided are: i) a murine version of MAB12, ii) a PD-1 inhibitor, and iii) a combination of mMAB12 and the PD-1 inhibitor. Antibody treatment times (days) are shown by arrows.

FIG. 1C shows a subset of data from FIGS. 1A and 1B comparing mMAB12 alone and in combination with an anti-PD-1 checkpoint antibody in the mouse colon CT26 syngeneic tumor model. mMAB12 at 500 μg/animal inhibited tumor growth by 61.6% TGI (tumor growth inhibition) compared to control antibody-treated mice. This effect was statistically significant by Student's t test ($p<0.05$). The anti-PD-1 checkpoint antibody administered at 200 μg/animal was less efficacious than mMAB12 (37.8% TGI, $p<0.05$). However, the combination of mMAB12 with the PD-1 antibody resulted in additive anti-tumor efficacy (79.0% TGI, $p<0.001$) compared to the monotherapy treatments. The effect of the combination was statistically significant when compared to PD-1 and mMAB12 ($p<0.05$ in both cases). There was no untoward toxicity exhibited by the treated mice which all gained weight over the course of the treatment, except for one non-treatment-related expired mouse in the mMAB12 group.

Figure 2A:
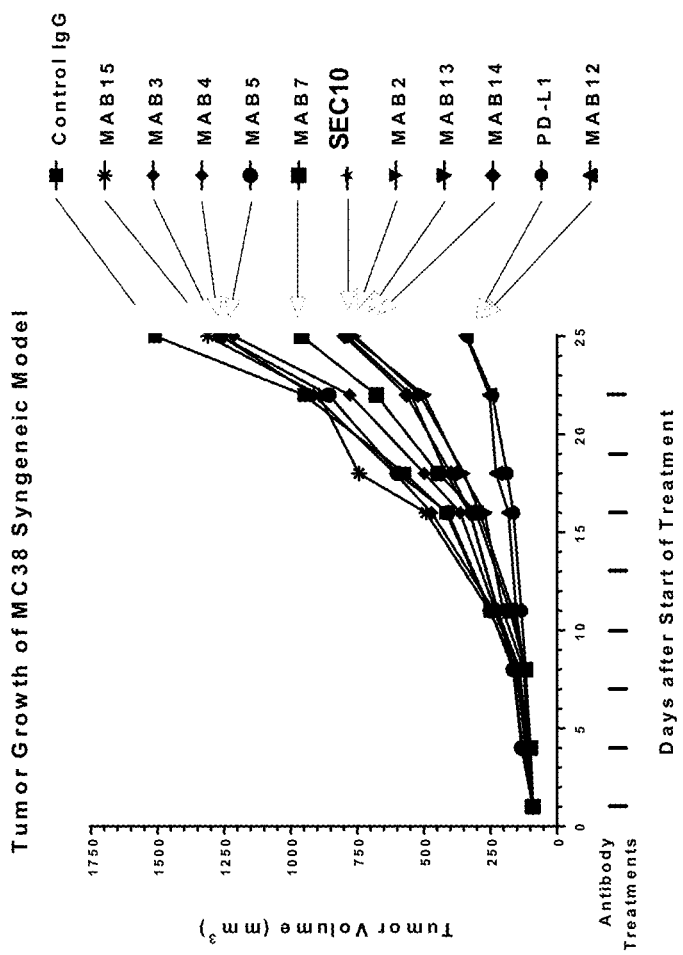
FIG. 2A is graphs showing tumor growth inhibition in MC38 tumor-bearing mice treated with a murine version of MABs 2, 3, 4, 5, 7, 12, 13, 14, and 15, as well as an IgG control and SEC10 as a comparator. Mice were treated with MAB monotherapy (FIG. 2A). Antibody treatment times (days) are shown by arrows.
Figure 2B:
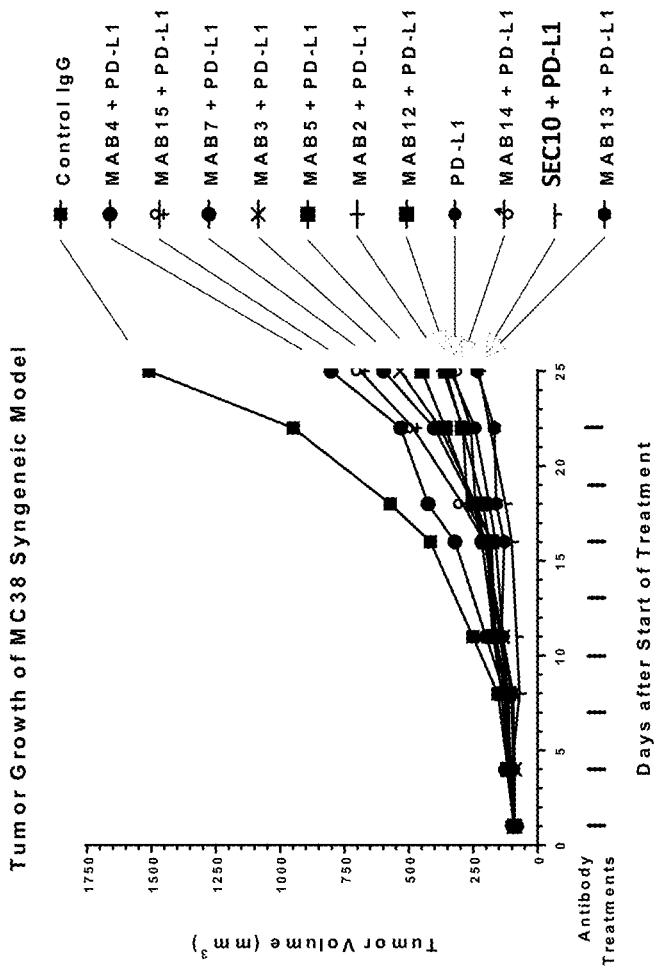
FIG. 2B is graphs showing tumor growth inhibition in MC38 tumor-bearing mice treated with a murine version of MABs 2, 3, 4, 5, 7, 12, 13, 14, and 15, as well as an IgG control and SEC10 as a comparator. Mice were treated with MAB in combination with a PD-L1 antibody (FIG. 2B). Antibody treatment times (days) are shown by arrows.

The same nine antibodies were evaluated in a second tumor model, the mouse colon MC38 syngeneic model. $5 \times 10^5$ mouse MC38 cells were implanted subcutaneously into female C57Bl/6 mice. The mice were randomized into treatment groups when the tumors reached an average tumor volume of 60 mm³ to 90 mm³ followed by initiation of treatment on Day 1. The anti-NRP-1 antibodies were administered as a monotherapy at 500 μg/dose or in combination with an anti-PD-L1 immune checkpoint inhibitor which was used at 250 μg/dose. The anti-PD-L1 antibody works in the same immune checkpoint pathway as the PD-1 antibody. FIG. 2A shows the monotherapy effect of antibodies in the MC38 model, and FIG. 2B shows the effect of combination of anti-NRP-1 antibodies with anti-PD-L1. The black arrows along the horizontal axis indicate the treatment days. The average tumor volume from 10 mice per group is shown for each treatment group.

Figure 2C:
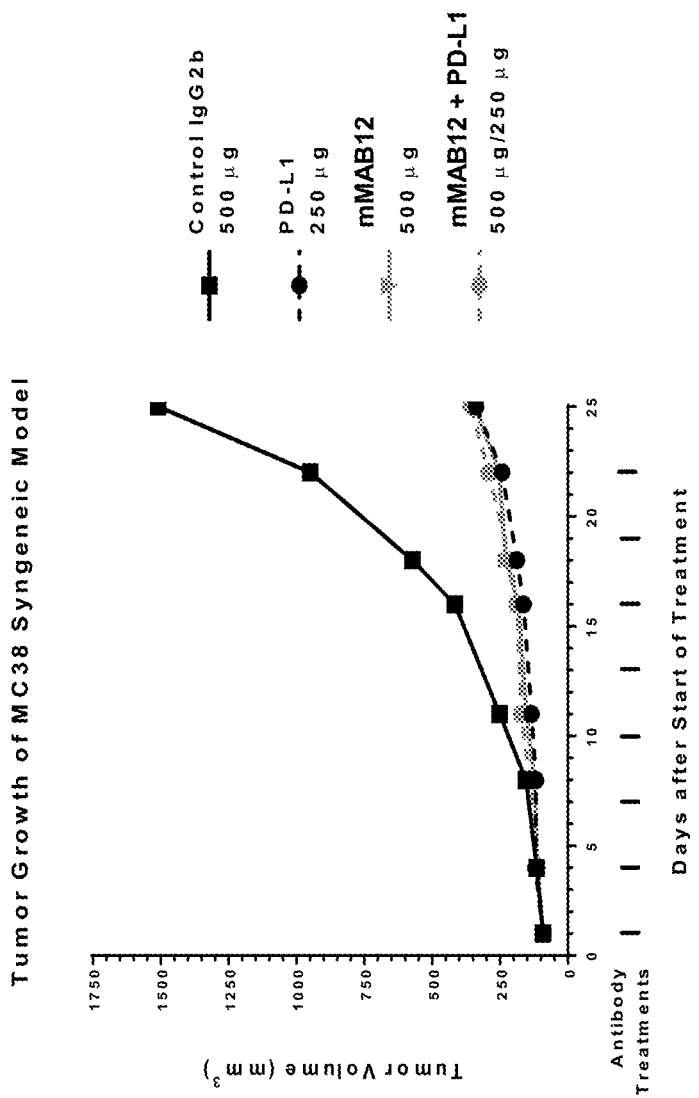
FIG. 2C is graphs showing tumor growth inhibition in MC38 tumor-bearing mice treated with a murine version of MABs 2, 3, 4, 5, 7, 12, 13, 14, and 15, as well as an IgG control and SEC10 as a comparator. Antibody treatment times (days) are shown by arrows. The anti-tumor efficacy of mMAB12 alone or in combination with PD-L1 antibody in the MC38 syngeneic colon mouse tumor model is shown in FIG. 2C.

The anti-tumor efficacy of mMAB12 in the MC38 syngeneic colon mouse tumor model is shown in FIG. 2C. The mMAB12 at 500 μg/animal inhibited tumor growth by 77.3% TGI ($p<0.05$) compared to control antibody-treated mice. The MC38 model is very sensitive to PD-1 antibody blockade. Therefore, an antibody against PD-L1 at 250 μg/animal which works in the same immune checkpoint pathway as the PD-1 antibody was used to demonstrate potential combination benefits. As expected, PD-L1 monotherapy blocked tumor growth at 77.5% TGI ($p<0.05$). However, the combination of mMAB12 with the PD-L1 antibody did not demonstrate additional anti-tumor benefits (76.2% TGI). As with the CT26 model there was no untoward toxicity exhibited by the treated mice which all gained weight over the course of the treatment. Four antibodies (MABs 2, 5, 12, and 13) were selected based on their efficacies in the CT26 and MC38 studies and retested in the MC38 model under the same conditions (alone and in combination with anti-PD-L1). The findings in the repeat MC38 study confirmed the above findings for efficacy and tolerability.

Example 4

Evaluation of Blockade of NRP-1 Ligands

Quantitative ligand blocking studies, measuring the ability of antibodies to block the binding of recombinant human SEMA3A and human VEGFA to recombinant human NRP-1, was measured by a blocking ELISA. To measure the ability of antibody to block the SEMA3A/NRP-1 interaction, the assay plate was coated with human SEMA3A at 2.5 μg/mL in PBS, overnight at 4° C. Biotinylated human NRP-1 (500 ng/mL in 1% BSA/PBS) was incubated with test antibody (30-0.002 g/mL, 4-fold dilution in 1% BSA/PBS) prior to addition to the assay plate, and then HRP conjugated streptavidin (1:200 in 1% BSA/PBS) was used for detection of NRP-1 bound to SEMA3A. Briefly, to measure the ability of antibody to block the VEGFA/NRP-1 interaction, the assay plate was coated with human NRP-1 at 2.5 μg/mL in PBS, overnight at 4° C. Test antibody (30-0.002 μg/mL, 4-fold dilution in 1% BSA/PBS) was incubated with VEGFA (125 ng/mL) prior to addition to the assay plate, biotinylated anti-VEGFA antibody (0.2 μg/mL in 1% BSA/PBS) was added, and then HRP conjugated streptavidin (1:200 in 1% BSA/PBS) was used for detection of VEGFA bound to NRP-1. The $IC_{50}$ values for 15 IgG1 format test antibodies blocking SEMA3A/VEGFA binding are shown in Table 7.

TABLE 7

$IC_{50}$ values for Blocking Assays with IgG1 Format Antibodies

| MAB | SEMA3A/NRP-1 Blocking $IC_{50}$ (nM) | VEGFA/NRP-1 Blocking $IC_{50}$ (nM) |
| --- | --- | --- |
| 1 | 2.9 | No Blocking |
| 2 | 3.1 | No Blocking |
| 3 | 0.6 | No Blocking |
| 4 | 3.9 | No Blocking |
| 5 | 5.9 | No Blocking |
| 6 | 1.8 | 7.4 |
| 7 | 1.7 | 6.9 |
| 8 | 2.0 | 7.3 |
| 9 | 1.8 | 6.5 |
| 10 | 1.5 | 6.7 |

TABLE 7-continued

IC$_{50}$ values for Blocking Assays with IgG1 Format Antibodies

| MAB | SEMA3A/NRP-1 Blocking IC$_{50}$ (nM) | VEGFA/NRP-1 Blocking IC$_{50}$ (nM) |
|---|---|---|
| 11 | 0.8 | 5.9 |
| 12 | 0.8 | 6.0 |
| 13 | 3.4 | No Blocking |
| 14 | 3.1 | No Blocking |
| 15 | No Blocking | No Blocking |

Eight MABs were converted to IgG4 S228P format and the assay was repeated. A summary of the averages is shown in Table 8.

TABLE 8

Averages for Blocking Assays with IgG4 Format Antibodies

| MAB | SEMA3A/NRP-1 Blocking IC50 (nM) | n | VEGFA/NRP-1 Blocking IC50 (nM) | n |
|---|---|---|---|---|
| MAB2 I111T* IgG4 S228P | 2.8 | 2 | No Blocking | 1 |
| MAB2 IgG4 S228P | 2.6 | 2 | No Blocking | 2 |
| MAB3 IgG4 S228P | 2.0 | 2 | No Blocking | 2 |
| MAB4 IgG4 S228P | 2.3 | 2 | No Blocking | 2 |
| MAB5 IgG4 S228P | 2.9 | 2 | No Blocking | 2 |
| MAB12 IgG4 S228P | 1.2 | 2 | 3.2 | 2 |
| MAB13 IgG4 S228P | 0.9 | 2 | 2.9 | 2 |
| MAB14 IgG4 S228P | 0.6 | 2 | 2.5 | 2 |

*humanizing site-directed mutation

Example 5

Epitope Binning of MAB12 vs SEC10

Epitope binning for MAB12 and SEC10 was measured using BioLayer Interferometry (BLI) using an Octet® QKe instrument (ForteBio®). MAB12 or SEC10 at 5 µg/mL was immobilized on anti-human Fc AHC sensors for 300 seconds. Sensors were then dipped in kinetics buffer for baseline determination. Next, sensors were dipped in human IgG at 200 µg/ml for 400 seconds to saturate all the IgG Fc binding sites on the sensors. After baseline determination, the sensors were exposed to 100 nM human NRP-1-HIS for 300 seconds to allow for antigen binding. Finally, sensors were transferred to wells containing 20 µg/mL of either MAB12 or SEC10 for 300 seconds to analyze antibody binding. If the test antibody showed clear binding in the last step, it was considered a non-competitor (different epitope bin), and if the test antibody did not show clear binding, it was considered a competitor (same epitope bin).

Figure 3:
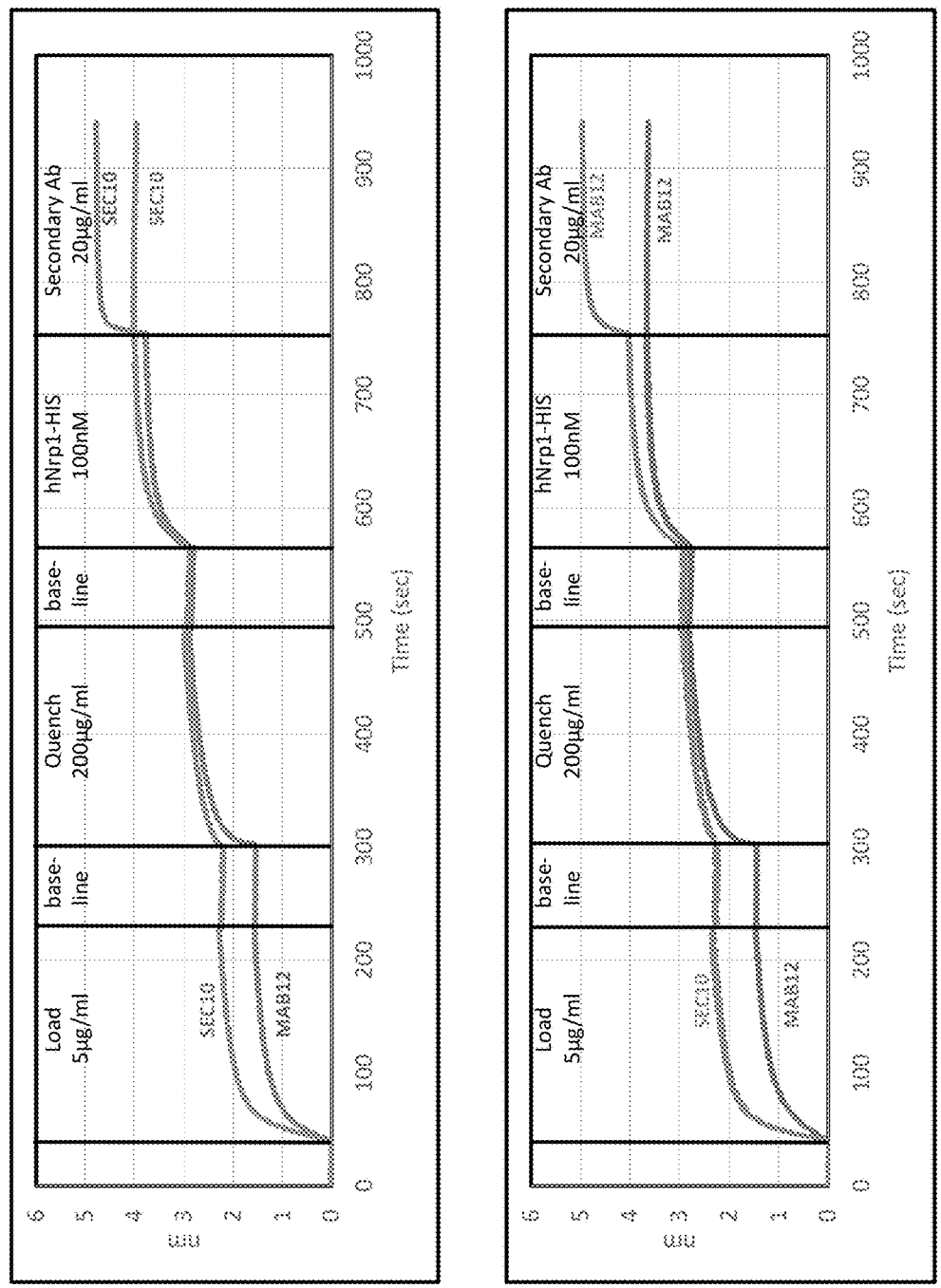
FIG. 3 is two graphs showing epitope binning data for the anti-NRP-1 antibodies MAB12 and SEC10. The top panel shows binning data for MAB12 and SEC10 with 5 µg/mL MAB12 immobilized on anti-human Fc AHC sensors. The bottom panel shows binning data for MAB12 and SEC10 with 5 µg/mL SEC10 immobilized on the sensors. NRP1 protein is bound to the immobilized antibody and binding of the second antibody is evaluated. The traces show that MAB12 and SEC10 are able to simultaneously bind NRP1.

Results are shown in FIG. 3. Capturing MAB12 and then binding NRP-1 does not prevent SEC10 from also binding NRP-1 (top panel). Similarly, capturing SEC10 and then binding NRP-1 does not prevent MAB12 from also binding NRP-1 (bottom panel). Self-binning (e.g., capture MAB12, bind NRP-1, test binding of MAB12) served as a positive control for binning. These data show that MAB12 and SEC10 can simultaneously bind NRP-1, and must therefore bind to different epitopes.

Example 6

Binding of Anti-NRP-1 Antibodies to NRP-1 Domains

In order to understand the approximate binding domain for antibodies binding to human NRP-1, the ability of antibodies to bind fragments of NRP-1 that contained different domains of NRP-1 extracellular region was measured by BLI using an Octet® QKe instrument (ForteBio®). Recombinant human NRP-1-Fc fusion proteins consisted of a1, a1a2, a1a2b1, a2b1b2, or a1a2b1b2 domains, and the differences in antibody binding to each protein led to determination of which primary domain the antibody binds. The BLI analysis was performed at 29° C. or 30° C. using 1× kinetics buffer (ForteBio) as the assay buffer. Briefly, antibodies (5 µg/mL) were captured onto anti-human IgG Fc (AHC) biosensors for 250 seconds. Then sensors were dipped into assay buffer (100 seconds) to achieve a baseline prior to measuring binding to each NRP-1 protein. A quenching step using human IgG Fc (150 nM, 250 nM or 500 nM, depending on the experiment) for 250 seconds was performed next. Sensors were then dipped into each NRP-1 protein at 500 nM for 300 seconds, followed by dissociation of each NRP-1 protein in assay buffer for 900 or 1000 seconds. Agitation was performed at 900 rpm or 1000 rpm for all steps, depending on the experiment.

Table 9 shows the results of the assays described above. The binding domain for each antibody is shown in the far-right column.

TABLE 9

NRP1 Domain Binding Specificity

| Antibody | a1 | a1a2 | a1a2b1 | a2b1b2 | a1a2b1b2 | Binding Domain |
|---|---|---|---|---|---|---|
| MAB1 | − | + | + | + | + | a2 |
| MAB2 | − | + | + | + | + | a2 |
| MAB3 | + | + | + | + | + | a1 |
| MAB4 | + | + | + | + | + | a1 |
| MAB5 | − | + | + | + | + | a2 |
| MAB6 | − | + | + | + | + | a2 |
| MAB7 | − | − | − | + | + | b2 |
| MAB8 | − | − | + | + | + | b1 |
| MAB9 | − | − | + | + | + | b1 |
| MAB10 | − | − | + | + | + | b1 |
| MAB11 | − | − | + | + | + | b1 |
| MAB12 | − | − | + | + | + | b1 |
| MAB13 | − | − | + | + | + | b1 |
| MAB14 | − | − | + | + | + | b1 |
| MAB15 | + | + | + | − | + | a1 |
| SEC10* | − | −/+ | + | + | + | b1 with weak a2 |
| SEC3** | + | + | + | − | + | a1 |
| MAB59941*** | − | − | − | + | + | b2 |

*SEQ ID Nos 141-142
**Described in Appleton, et. al., The EMBO Journal (2007) 26, 4902-4912.
***Described in Delgoffe GM, Woo S-R, Turnis ME, Gravano DM, Guy C, Overacre AE, et al. Stability and function of regulatory T cells is maintained by a neuropilin-1-semaphorin-4a axis. Nature 501(7466): 252-6. Available from R&D Systems.

Example 7

Mutational Analysis for Epitope Determination

To identify the epitope for MAB12 binding to the b1 domain of human NRP1, single point mutations were made within the human NRP1 b1 domain. Either alanine substitutions or NRP2 specific residues were used (MAB12 does not bind NRP2). Proteins were expressed in HEK293 cells, secreted as soluble protein, purified on Ni-NTA resin, and characterized by SDS-PAGE. Binding was assessed by Bio-Layer Interferometry (BLI) using the Octet platform. MAB12 was captured on anti-human Fc sensors, washed, and exposed to either monomeric wild type human NRP1 b1 domain or to monomeric mutant NRP1 b1. Residues considered part of the binding epitope demonstrated reduced binding (e.g., a $K_D$ more than 5-fold poorer than that of binding to wild type human NRP1 b1) or no binding. Single point mutants P317A, D320A, T349A, K352G, Y353A, Y354A, and T413A resulted in reduced binding, whereas K351N and E412H resulted in no binding.

Example 8

Structure Determination of MAB12 Complexed with NRP1

The binding epitope was also identified through crystallographic studies. MAB12 Fab was complexed with human NRP1 b1, purified by size exclusion chromatography and concentrated to 10 mg/ml. Crystals were grown out of 42% PEG200, HEPES pH 7. X-ray data was collected at Argonne National Laboratories (GM/CA CAT 23ID-D) and processed using CCP4 and Phenix. NRP1 b1 residues within a contact distance of 3.8 Å from the heavy and light chain were considered part of the binding epitope and include Y297, T316, D320, E348, T349, K350, K351, K352, Y353, Y354, E412, T413, G414 and I415.

Example 9

Analysis of Amino Acid Modifications of MAB12

Analysis of the amino acid modifications of purified MAB12 suggested that the deletion of lysine at the C terminal of the heavy chain occurred in most of the purified antibodies and that the pyroglutamylation of glutamic acid at the N terminal of the light chain occurred in some of the purified antibodies.

INCORPORATION BY REFERENCE

The entire disclosures of all patent and non-patent publications cited herein are each incorporated by reference in their entireties for all purposes.

Other Embodiments

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

APPENDIX A: SEQUENCE REFERENCE TABLE

| SEQ ID NO | Molecule | Region | Sequence |
| --- | --- | --- | --- |
| 1 | MAB1 | VH FR1 | QVQLVQSGAGVKKPGASVKVSCKASG |
| 2 | MAB2 | VH FR1 | QVQLVQSGAEVKKPGASVKVSCKASG |
| 3 | MAB3 | VH FR1 | QAQLVQSGAEVKKPGASVKVSCKASG |
| 2 | MAB4 | VH FR1 | QVQLVQSGAEVKKPGASVKVSCKASG |
| 2 | MAB5 | VH FR1 | QVQLVQSGAEVKKPGASVKVSCKASG |
| 4 | MAB6 | VH FR1 | QVQLVQSGAKVKKPGASVKVSCKASG |
| 5 | MAB7 | VH FR1 | EVQLVESGGGLVQPGGSLRLSCAASG |
| 6 | MAB8 | VH FR1 | EVQLLESGGGLVQPGGSLRLSCAASG |
| 6 | MAB9 | VH FR1 | EVQLLESGGGLVQPGGSLRLSCAASG |
| 6 | MAB10 | VH FR1 | EVQLLESGGGLVQPGGSLRLSCAASG |
| 6 | MAB11 | VH FR1 | EVQLLESGGGLVQPGGSLRLSCAASG |
| 6 | MAB12 | VH FR1 | EVQLLESGGGLVQPGGSLRLSCAASG |
| 7 | MAB13 | VH FR1 | QVQLQQWGAGLLKPSETLSLTCAVYG |
| 7 | MAB14 | VH FR1 | QVQLQQWGAGLLKPSETLSLTCAVYG |
| 7 | MAB15 | VH FR1 | QVQLQQWGAGLLKPSETLSLTCAVYG |
| 8 | MAB1 | VH CDR1 | YTFRSYYML |
| 8 | MAB2 | VH CDR1 | YTFRSYYML |

-continued

| APPENDIX A: SEQUENCE REFERENCE TABLE | | | |
|---|---|---|---|
| SEQ ID NO | Molecule | Region | Sequence |
| 9 | MAB3 | VH CDR1 | YTFSRYYMH |
| 9 | MAB4 | VH CDR1 | YTFSRYYMH |
| 10 | MAB5 | VH CDR1 | YTFTSYYMH |
| 10 | MAB6 | VH CDR1 | YTFTSYYMH |
| 11 | MAB7 | VH CDR1 | FTFSSYWME |
| 12 | MAB8 | VH CDR1 | FTFASYAMV |
| 13 | MAB9 | VH CDR1 | FTFKSYAMV |
| 14 | MAB10 | VH CDR1 | FTFSSVAMV |
| 14 | MAB11 | VH CDR1 | FTFSSVAMV |
| 14 | MAB12 | VH CDR1 | FTFSSVAMV |
| 15 | MAB13 | VH CDR1 | GSFRGYYWE |
| 15 | MAB14 | VH CDR1 | GSFRGYYWE |
| 16 | MAB15 | VH CDR1 | GSFVKYYWS |
| 17 | MAB1 | VH FR2 | WVRQAPGQGLEWMG |
| 17 | MAB2 | VH FR2 | WVRQAPGQGLEWMG |
| 17 | MAB3 | VH FR2 | WVRQAPGQGLEWMG |
| 17 | MAB4 | VH FR2 | WVRQAPGQGLEWMG |
| 17 | MAB5 | VH FR2 | WVRQAPGQGLEWMG |
| 18 | MAB6 | VH FR2 | WVRQVPGQGLEWMG |
| 19 | MAB7 | VH FR2 | WVRQAPGKGLEWVA |
| 20 | MAB8 | VH FR2 | WVRQAPGKGLEWVS |
| 20 | MAB9 | VH FR2 | WVRQAPGKGLEWVS |
| 20 | MAB10 | VH FR2 | WVRQAPGKGLEWVS |
| 20 | MAB11 | VH FR2 | WVRQAPGKGLEWVS |
| 20 | MAB12 | VH FR2 | WVRQAPGKGLEWVS |
| 21 | MAB13 | VH FR2 | WIRQPPGKGLEWIG |
| 22 | MAB14 | VH FR2 | WSRQPPGKGLEWIG |
| 21 | MAB15 | VH FR2 | WIRQPPGKGLEWIG |
| 23 | MAB1 | VH CDR2 | IIDPSDGSTSYAQKFQG |
| 23 | MAB2 | VH CDR2 | IIDPSDGSTSYAQKFQG |
| 24 | MAB3 | VH CDR2 | IINPLGGSTLYAQKFQG |
| 24 | MAB4 | VH CDR2 | IINPLGGSTLYAQKFQG |
| 25 | MAB5 | VH CDR2 | IINPQGGDTSYAQKFQG |
| 25 | MAB6 | VH CDR2 | IINPQGGDTSYAQKFQG |
| 26 | MAB7 | VH CDR2 | RIKRDGSEKYYVDSVKG |
| 27 | MAB8 | VH CDR2 | IISGSGGSTYYADSVKG |
| 28 | MAB9 | VH CDR2 | IISGSGGATYYADSVKG |
| 29 | MAB10 | VH CDR2 | AISGSGGATYYADSVKG |

-continued

| APPENDIX A: SEQUENCE REFERENCE TABLE ||||
|---|---|---|---|
| SEQ ID NO | Molecule | Region | Sequence |
| 30 | MAB11 | VH CDR2 | AISGSGGATYYADSVEG |
| 30 | MAB12 | VH CDR2 | AISGSGGATYYADSVEG |
| 31 | MAB13 | VH CDR2 | EISHSGSTNYNPSLKS |
| 31 | MAB14 | VH CDR2 | EISHSGSTNYNPSLKS |
| 32 | MAB15 | VH CDR2 | DIWHSGMTNYNPSLKS |
| 33 | MAB1 | VH FR3 | RVTMTRDTPTSTVYMELSSLRSEDTAVYYC |
| 34 | MAB2 | VH FR3 | RVTMTRDASTSTVYMELSSLRSEDTAVYYC |
| 35 | MAB3 | VH FR3 | RVTMTRDTSTSTVYMELSSLRSEDTAVYYC |
| 35 | MAB4 | VH FR3 | RVTMTRDTSTSTVYMELSSLRSEDTAVYYC |
| 35 | MAB5 | VH FR3 | RVTMTRDTSTSTVYMELSSLRSEDTAVYYC |
| 35 | MAB6 | VH FR3 | RVTMTRDTSTSTVYMELSSLRSEDTAVYYC |
| 36 | MAB7 | VH FR3 | RFTISRDNAKNSLYLQMNSLRAEDTAVYYC |
| 37 | MAB8 | VH FR3 | RFTISRDNSKNTLYLQMNSLRAEDTAVYYC |
| 37 | MAB9 | VH FR3 | RFTISRDNSKNTLYLQMNSLRAEDTAVYYC |
| 37 | MAB10 | VH FR3 | RFTISRDNSKNTLYLQMNSLRAEDTAVYYC |
| 38 | MAB11 | VH FR3 | RFTISRDNSKNTLYLQMSSLRAEDTAVYYC |
| 37 | MAB12 | VH FR3 | RFTISRDNSKNTLYLQMNSLRAEDTAVYYC |
| 39 | MAB13 | VH FR3 | RVTISVDTSKNQFSLKLSSVTAADTAVYYC |
| 40 | MAB14 | VH FR3 | RVTISVDTSKNQFSLKLSPVTAADTAVYYC |
| 39 | MAB15 | VH FR3 | RVTISVDTSKNQFSLKLSSVTAADTAVYYC |
| 41 | MAB1 | VH CDR3 | ARGARRITGYGMDV |
| 41 | MAB2 | VH CDR3 | ARGARRITGYGMDV |
| 42 | MAB3 | VH CDR3 | ARDLGYYGSGMHA |
| 43 | MAB4 | VH CDR3 | ARDLGYYGSGMHV |
| 44 | MAB5 | VH CDR3 | ARDRGMYYASGFGP |
| 45 | MAB6 | VH CDR3 | ARDRGMYYASGFNP |
| 46 | MAB7 | VH CDR3 | ARDQGYKTPTDFDL |
| 47 | MAB8 | VH CDR3 | AKDPGYDSSRYYYSNYGMDV |
| 47 | MAB9 | VH CDR3 | AKDPGYDSSRYYYSNYGMDV |
| 47 | MAB10 | VH CDR3 | AKDPGYDSSRYYYSNYGMDV |
| 47 | MAB11 | VH CDR3 | AKDPGYDSSRYYYSNYGMDV |
| 47 | MAB12 | VH CDR3 | AKDPGYDSSRYYYSNYGMDV |
| 48 | MAB13 | VH CDR3 | ARARPYREPYGMDV |
| 48 | MAB14 | VH CDR3 | ARARPYREPYGMDV |
| 49 | MAB15 | VH CDR3 | ARGPGYDSSGYSRRFDP |
| 50 | MAB1 | VH FR4 | WGQGTTVTVSS |
| 51 | MAB2 | VH FR4 | WGQGTTVIVSS |

-continued

| SEQ ID NO | Molecule | Region | Sequence |
|---|---|---|---|
| \multicolumn{4}{c}{APPENDIX A: SEQUENCE REFERENCE TABLE} |
| 52 | MAB3 | VH FR4 | WGQGTLVTVSS |
| 52 | MAB4 | VH FR4 | WGQGTLVTVSS |
| 52 | MAB5 | VH FR4 | WGQGTLVTVSS |
| 52 | MAB6 | VH FR4 | WGQGTLVTVSS |
| 53 | MAB7 | VH FR4 | WGRGTLVTVSS |
| 50 | MAB8 | VH FR4 | WGQGTTVTVSS |
| 50 | MAB9 | VH FR4 | WGQGTTVTVSS |
| 50 | MAB10 | VH FR4 | WGQGTTVTVSS |
| 50 | MAB11 | VH FR4 | WGQGTTVTVSS |
| 50 | MAB12 | VH FR4 | WGQGTTVTVSS |
| 50 | MAB13 | VH FR4 | WGQGTTVTVSS |
| 50 | MAB14 | VH FR4 | WGQGTTVTVSS |
| 52 | MAB15 | VH FR4 | WGQGTLVTVSS |
| 54 | MAB1 | VL FR1 | DIQMTQSPSSVSASVGDRVTITC |
| 54 | MAB2 | VL FR1 | DIQMTQSPSSVSASVGDRVTITC |
| 54 | MAB3 | VL FR1 | DIQMTQSPSSVSASVGDRVTITC |
| 54 | MAB4 | VL FR1 | DIQMTQSPSSVSASVGDRVTITC |
| 55 | MAB5 | VL FR1 | EIVMTQSPGTLSLSPGERATLSC |
| 55 | MAB6 | VL FR1 | EIVMTQSPGTLSLSPGERATLSC |
| 56 | MAB7 | VL FR1 | DIQMTQSPSSLSASVGDRVTITC |
| 56 | MAB8 | VL FR1 | DIQMTQSPSSLSASVGDRVTITC |
| 56 | MAB9 | VL FR1 | DIQMTQSPSSLSASVGDRVTITC |
| 56 | MAB10 | VL FR1 | DIQMTQSPSSLSASVGDRVTITC |
| 56 | MAB11 | VL FR1 | DIQMTQSPSSLSASVGDRVTITC |
| 56 | MAB12 | VL FR1 | DIQMTQSPSSLSASVGDRVTITC |
| 57 | MAB13 | VL FR1 | DIQLTQSPSSVSASVGDRVTITC |
| 57 | MAB14 | VL FR1 | DIQLTQSPSSVSASVGDRVTITC |
| 58 | MAB15 | VL FR1 | DIQMTQSPSTLSASVGDRVTITC |
| 59 | MAB1 | VL CDR1 | RASQGISSWLA |
| 59 | MAB2 | VL CDR1 | RASQGISSWLA |
| 60 | MAB3 | VL CDR1 | RASQGISRWLA |
| 60 | MAB4 | VL CDR1 | RASQGISRWLA |
| 61 | MAB5 | VL CDR1 | RASQSVSSSYLA |
| 61 | MAB6 | VL CDR1 | RASQSVSSSYLA |
| 62 | MAB7 | VL CDR1 | QASQDITNYLN |
| 63 | MAB8 | VL CDR1 | RASQSISSYLN |
| 63 | MAB9 | VL CDR1 | RASQSISSYLN |
| 63 | MAB10 | VL CDR1 | RASQSISSYLN |

-continued

| SEQ ID NO | Molecule | Region | Sequence |
|---|---|---|---|
| 63 | MAB11 | VL CDR1 | RASQSISSYLN |
| 63 | MAB12 | VL CDR1 | RASQSISSYLN |
| 64 | MAB13 | VL CDR1 | RASQDISSWLA |
| 64 | MAB14 | VL CDR1 | RASQDISSWLA |
| 65 | MAB15 | VL CDR1 | RASQSISSWLA |
| 66 | MAB1 | VL FR2 | WYQQKPGKAPKLLIY |
| 66 | MAB2 | VL FR2 | WYQQKPGKAPKLLIY |
| 66 | MAB3 | VL FR2 | WYQQKPGKAPKLLIY |
| 66 | MAB4 | VL FR2 | WYQQKPGKAPKLLIY |
| 146 | MAB5 | VL FR2 | WYQQKPGQAPRLLIY |
| 146 | MAB6 | VL FR2 | WYQQKPGQAPRLLIY |
| 66 | MAB7 | VL FR2 | WYQQKPGKAPKLLIY |
| 66 | MAB8 | VL FR2 | WYQQKPGKAPKLLIY |
| 66 | MAB9 | VL FR2 | WYQQKPGKAPKLLIY |
| 66 | MAB10 | VL FR2 | WYQQKPGKAPKLLIY |
| 66 | MAB11 | VL FR2 | WYQQKPGKAPKLLIY |
| 66 | MAB12 | VL FR2 | WYQQKPGKAPKLLIY |
| 66 | MAB13 | VL FR2 | WYQQKPGKAPKLLIY |
| 66 | MAB14 | VL FR2 | WYQQKPGKAPKLLIY |
| 66 | MAB15 | VL FR2 | WYQQKPGKAPKLLIY |
| 67 | MAB1 | VL CDR2 | AASNLQS |
| 67 | MAB2 | VL CDR2 | AASNLQS |
| 68 | MAB3 | VL CDR2 | AASSLQS |
| 68 | MAB4 | VL CDR2 | AASSLQS |
| 69 | MAB5 | VL CDR2 | GASNRAT |
| 69 | MAB6 | VL CDR2 | GASNRAT |
| 70 | MAB7 | VL CDR2 | DASNLET |
| 71 | MAB8 | VL CDR2 | GASSLQS |
| 71 | MAB9 | VL CDR2 | GASSLQS |
| 71 | MAB10 | VL CDR2 | GASSLQS |
| 71 | MAB11 | VL CDR2 | GASSLQS |
| 71 | MAB12 | VL CDR2 | GASSLQS |
| 68 | MAB13 | VL CDR2 | AASSLQS |
| 68 | MAB14 | VL CDR2 | AASSLQS |
| 72 | MAB15 | VL CDR2 | KASSLES |
| 73 | MAB1 | VL FR3 | GVPSRFSGSGSGTDFTLTISSLQPEDFATYYC |
| 73 | MAB2 | VL FR3 | GVPSRFSGSGSGTDFTLTISSLQPEDFATYYC |

-continued

| | | | APPENDIX A: SEQUENCE REFERENCE TABLE |
|---|---|---|---|
| SEQ ID NO | Molecule | Region | Sequence |
| 73 | MAB3 | VL FR3 | GVPSRFSGSGSGTDFTLTISSLQPEDFATYYC |
| 73 | MAB4 | VL FR3 | GVPSRFSGSGSGTDFTLTISSLQPEDFATYYC |
| 74 | MAB5 | VL FR3 | GIPDRFSGSGSGTDFTLTISRLEPEDFAVYYC |
| 74 | MAB6 | VL FR3 | GIPDRFSGSGSGTDFTLTISRLEPEDFAVYYC |
| 75 | MAB7 | VL FR3 | GVPSRFSGSGSGTDFTFTISSLQPEDIATYYC |
| 73 | MAB8 | VL FR3 | GVPSRFSGSGSGTDFTLTISSLQPEDFATYYC |
| 73 | MAB9 | VL FR3 | GVPSRFSGSGSGTDFTLTISSLQPEDFATYYC |
| 73 | MAB10 | VL FR3 | GVPSRFSGSGSGTDFTLTISSLQPEDFATYYC |
| 73 | MAB11 | VL FR3 | GVPSRFSGSGSGTDFTLTISSLQPEDFATYYC |
| 73 | MAB12 | VL FR3 | GVPSRFSGSGSGTDFTLTISSLQPEDFATYYC |
| 73 | MAB13 | VL FR3 | GVPSRFSGSGSGTDFTLTISSLQPEDFATYYC |
| 73 | MAB14 | VL FR3 | GVPSRFSGSGSGTDFTLTISSLQPEDFATYYC |
| 76 | MAB15 | VL FR3 | GVPSRFSGSGSGTEFTLTISSLQPDDFATYYC |
| 77 | MAB1 | VL CDR3 | QQASVFPFT |
| 77 | MAB2 | VL CDR3 | QQASVFPFT |
| 78 | MAB3 | VL CDR3 | QQANLLPFT |
| 78 | MAB4 | VL CDR3 | QQANLLPFT |
| 79 | MAB5 | VL CDR3 | QQLSSFPIT |
| 79 | MAB6 | VL CDR3 | QQLSSFPIT |
| 80 | MAB7 | VL CDR3 | QQSDVLPIT |
| 81 | MAB8 | VL CDR3 | QQTYSLYT |
| 81 | MAB9 | VL CDR3 | QQTYSLYT |
| 81 | MAB10 | VL CDR3 | QQTYSLYT |
| 81 | MAB11 | VL CDR3 | QQTYSLYT |
| 81 | MAB12 | VL CDR3 | QQTYSLYT |
| 82 | MAB13 | VL CDR3 | QQELAFPRT |
| 82 | MAB14 | VL CDR3 | QQELAFPRT |
| 83 | MAB15 | VL CDR3 | QQLNSYPPT |
| 84 | MAB1 | VL FR4 | FGGGTKVEIK |
| 84 | MAB2 | VL FR4 | FGGGTKVEIK |
| 84 | MAB3 | VL FR4 | FGGGTKVEIK |
| 84 | MAB4 | VL FR4 | FGGGTKVEIK |
| 84 | MAB5 | VL FR4 | FGGGTKVEIK |
| 84 | MAB6 | VL FR4 | FGGGTKVEIK |
| 84 | MAB7 | VL FR4 | FGGGTKVEIK |
| 84 | MAB8 | VL FR4 | FGGGTKVEIK |
| 84 | MAB9 | VL FR4 | FGGGTKVEIK |
| 84 | MAB10 | VL FR4 | FGGGTKVEIK |

APPENDIX A: SEQUENCE REFERENCE TABLE

| SEQ ID NO | Molecule | Region | Sequence |
|---|---|---|---|
| 84 | MAB11 | VL FR4 | FGGGTKVEIK |
| 84 | MAB12 | VL FR4 | FGGGTKVEIK |
| 84 | MAB13 | VL FR4 | FGGGTKVEIK |
| 84 | MAB14 | VL FR4 | FGGGTKVEIK |
| 84 | MAB15 | VL FR4 | FGGGTKVEIK |
| 85 | MAB1 | VH Full | QVQLVQSGAGVKKPGASVKVSCKASGYTFRSYYMLWV RQAPGQGLEWMGIIDPSDGSTSYAQKFQGRVTMTRDT PTSTVYMELSSLRSEDTAVYYCARGARRITGYGMDVW GQGTTVTVSS |
| 86 | MAB2 | VH Full | QVQLVQSGAEVKKPGASVKVSCKASGYTFRSYYMLWV RQAPGQGLEWMGIIDPSDGSTSYAQKFQGRVTMTRDA STSTVYMELSSLRSEDTAVYYCARGARRITGYGMDVW GQGTTVIVSS |
| 87 | MAB3 | VH Full | QAQLVQSGAEVKKPGASVKVSCKASGYTFSRYYMHWV RQAPGQGLEWMGIINPLGGSTLYAQKFQGRVTMTRDT STSTVYMELSSLRSEDTAVYYCARDLGYYGSGMHAWG QGTLVTVSS |
| 88 | MAB4 | VH Full | QVQLVQSGAEVKKPGASVKVSCKASGYTFSRYYMHWV RQAPGQGLEWMGIINPLGGSTLYAQKFQGRVTMTRDT STSTVYMELSSLRSEDTAVYYCARDLGYYGSGMHVWG QGTLVTVSS |
| 89 | MAB5 | VH Full | QVQLVQSGAEVKKPGASVKVSCKASGYTFTSYYMHWV RQAPGQGLEWMGIINPQGGDTSYAQKFQGRVTMTRDT STSTVYMELSSLRSEDTAVYYCARDRGMYYASGFGPW GQGTLVTVSS |
| 90 | MAB6 | VH Full | QVQLVQSGAKVKKPGASVKVSCKASGYTFTSYYMHWV RQVPGQGLEWMGIINPQGGDTSYAQKFQGRVTMTRDT STSTVYMELSSLRSEDTAVYYCARDRGMYYASGFNPW GQGTLVTVSS |
| 91 | MAB7 | VH Full | EVQLVESGGGLVQPGGSLRLSCAASGFTFSSYWMEWV RQAPGKGLEWVARIKRDGSEKYYVDSVKGRFTISRDN AKNSLYLQMNSLRAEDTAVYYCARDQGYKTPTDFDLW GRGTLVTVSS |
| 92 | MAB8 | VH Full | EVQLLESGGGLVQPGGSLRLSCAASGFTFASYAMVWV RQAPGKGLEWVSIISGSGGSTYYADSVKGRFTISRDN SKNTLYLQMNSLRAEDTAVYYCAKDPGYDSSRYYYSN YGMDVWGQGTTVTVSS |
| 93 | MAB9 | VH Full | EVQLLESGGGLVQPGGSLRLSCAASGFTFKSYAMVWV RQAPGKGLEWVSIISGSGGATYYADSVKGRFTISRDN SKNTLYLQMNSLRAEDTAVYYCAKDPGYDSSRYYYSN YGMDVWGQGTTVTVSS |
| 94 | MAB10 | VH Full | EVQLLESGGGLVQPGGSLRLSCAASGFTFSSVAMVWV RQAPGKGLEWVSAISGSGGATYYADSVKGRFTISRDN SKNTLYLQMNSLRAEDTAVYYCAKDPGYDSSRYYYSN YGMDVWGQGTTVTVSS |
| 95 | MAB11 | VH Full | EVQLLESGGGLVQPGGSLRLSCAASGFTFSSVAMVWV RQAPGKGLEWVSAISGSGGATYYADSVEGRFTISRDN SKNTLYLQMSSLRAEDTAVYYCAKDPGYDSSRYYYSN YGMDVWGQGTTVTVSS |
| 96 | MAB12 | VH Full | EVQLLESGGGLVQPGGSLRLSCAASGFTFSSVAMVWV RQAPGKGLEWVSAISGSGGATYYADSVEGRFTISRDN SKNTLYLQMNSLRAEDTAVYYCAKDPGYDSSRYYYSN YGMDVWGQGTTVTVSS |
| 97 | MAB13 | VH Full | QVQLQQWGAGLLKPSETLSLTCAVYGGSFRGYYWEWI RQPPGKGLEWIGEISHSGSTNYNPSLKSRVTISVDTS KNQFSLKLSSVTAADTAVYYCARARPYREPYGMDVWG QGTTVTVSS |

APPENDIX A: SEQUENCE REFERENCE TABLE

| SEQ ID NO | Molecule | Region | Sequence |
|---|---|---|---|
| 98 | MAB14 | VH Full | QVQLQQWGAGLLKPSETLSLTCAVYGGSFRGYYWEWS RQPPGKGLEWIGEISHSGSTNYNPSLKSRVTISVDTS KNQFSLKLSPVTAADTAVYYCARARPYREPYGMDVWG QGTTVTVSS |
| 99 | MAB15 | VH Full | QVQLQQWGAGLLKPSETLSLTCAVYGGSFVKYYWSWI RQPPGKGLEWIGDIWHSGMTNYNPSLKSRVTISVDTS KNQFSLKLSSVTAADTAVYYCARGPGYDSSGYSRRFD PWGQGTLVTVSS |
| 100 | MAB1 | VL Full | DIQMTQSPSSVSASVGDRVTITCRASQGISSWLAWYQ QKPGKAPKLLIYAASNLQSGVPSRFSGSGSGTDFTLT ISSLQPEDFATYYCQQASVFPFTFGGGTKVEIK |
| 100 | MAB2 | VL Full | DIQMTQSPSSVSASVGDRVTITCRASQGISSWLAWYQ QKPGKAPKLLIYAASNLQSGVPSRFSGSGSGTDFTLT ISSLQPEDFATYYCQQASVFPFTFGGGTKVEIK |
| 101 | MAB3 | VL Full | DIQMTQSPSSVSASVGDRVTITCRASQGISRWLAWYQ QKPGKAPKLLIYAASSLQSGVPSRFSGSGSGTDFTLT ISSLQPEDFATYYCQQANLLPFTFGGGTKVEIK |
| 101 | MAB4 | VL Full | DIQMTQSPSSVSASVGDRVTITCRASQGISRWLAWYQ QKPGKAPKLLIYAASSLQSGVPSRFSGSGSGTDFTLT ISSLQPEDFATYYCQQANLLPFTFGGGTKVEIK |
| 102 | MAB5 | VL Full | EIVMTQSPGTLSLSPGERATLSCRASQSVSSSYLAWY QQKPGQAPRLLIYGASNRATGIPDRFSGSGSGTDFTL TISRLEPEDFAVYYCQQLSSFPITFGGGTKVEIK |
| 102 | MAB6 | VL Full | EIVMTQSPGTLSLSPGERATLSCRASQSVSSSYLAWY QQKPGQAPRLLIYGASNRATGIPDRFSGSGSGTDFTL TISRLEPEDFAVYYCQQLSSFPITFGGGTKVEIK |
| 103 | MAB7 | VL Full | DIQMTQSPSSLSASVGDRVTITCQASQDITNYLNWYQ QKPGKAPKLLIYDASNLETGVPSRFSGSGSGTDFTFT ISSLQPEDIATYYCQQSDVLPITFGGGTKVEIK |
| 104 | MAB8 | VL Full | DIQMTQSPSSLSASVGDRVTITCRASQSISSYLNWYQ QKPGKAPKWYGASSLQSGVPSRFSGSGSGTDFTLTIS SLQPEDFATYYCQQTYSLYTFGGGTKVEIK |
| 104 | MAB9 | VL Full | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIK |
| 104 | MAB10 | VL Full | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIK |
| 104 | MAB11 | VL Full | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIK |
| 104 | MAB12 | VL Full | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIK |
| 105 | MAB13 | VL Full | DIQLTQSPSSVSASVGDRVTITCRASQDISSWLAWYQ QKPGKAPKLLIYAASSLQSGVPSRFSGSGSGTDFTLT ISSLQPEDFATYYCQQELAFPRTFGGGTKVEIK |
| 105 | MAB14 | VL Full | DIQLTQSPSSVSASVGDRVTITCRASQDISSWLAWYQ QKPGKAPKLLIYAASSLQSGVPSRFSGSGSGTDFTLT ISSLQPEDFATYYCQQELAFPRTFGGGTKVEIK |
| 106 | MAB15 | VL Full | DIQMTQSPSTLSASVGDRVTITCRASQSISSWLAWYQ QKPGKAPKLLIYKASSLESGVPSRFSGSGSGTEFTLT ISSLQPDDFATYYCQQLNSYPPTFGGGTKVEIK |
| 107 | MAB1 | HC Full-length IgG4 S228P | QVQLVQSGAEVKKPGASVKVSCKASGYTFRSYYMLWV RQAPGQGLEWMGIIDPSDGSTSYAQKFQGRVTMTRDT PTSTVYMELSSLRSEDTAVYYCARGARRITGYGMDVW GQGTTVTVSSASTKGPSVFPLAPCSRSTSESTAALGC |

APPENDIX A: SEQUENCE REFERENCE TABLE

| SEQ ID NO | Molecule | Region | Sequence |
|---|---|---|---|
| | | | LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLGK |
| 108 | MAB2 | HC Full-length IgG4 S228P | QVQLVQSGAEVKKPGASVKVSCKASGYTFRSYYMLWV RQAPGQGLEWMGIIDPSDGSTSYAQKFQGRVTMTRDA STSTVYMELSSLRSEDTAVYYCARGARRITGYGMDVW GQGTTVIVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLGK |
| 109 | MAB3 | HC Full-length IgG4 S228P | QAQLVQSGAEVKKPGASVKVSCKASGYTFSRYYMHWV RQAPGQGLEWMGIINPLGGSTLYAQKFQGRVTMTRDT STSTVYMELSSLRSEDTAVYYCARDLGYYGSGMHAWG QGTLVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| 110 | MAB4 | HC Full-length IgG4 S228P | QVQLVQSGAEVKKPGASVKVSCKASGYTFSRYYMHWV RQAPGQGLEWMGIINPLGGSTLYAQKFQGRVTMTRDT STSTVYMELSSLRSEDTAVYYCARDLGYYGSGMHVWG QGTLVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| 111 | MAB5 | HC Full-length IgG4 S228P | QVQLVQSGAEVKKPGASVKVSCKASGYTFTSYYMHWV RQAPGQGLEWMGIINPQGGDTSYAQKFQGRVTMTRDT STSTVYMELSSLRSEDTAVYYCARDRGMYYASGFGPW GQGTLVTVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLGK |
| 112 | MAB6 | HC Full-length IgG4 S228P | QVQLVQSGAKVKKPGASVKVSCKASGYTFTSYYMHWV RQVPGQGLEWMGIINPQGGDTSYAQKFQGRVTMTRDT STSTVYMELSSLRSEDTAVYYCARDRGMYYASGFNPW GQGTLVTVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI |

-continued

| APPENDIX A: SEQUENCE REFERENCE TABLE | | | |
|---|---|---|---|
| SEQ ID NO | Molecule | Region | Sequence |
| | | | EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLGK |
| 113 | MAB7 | HC Full-length IgG4 S228P | EVQLVESGGGLVQPGGSLRLSCAASGFTFSSYWMEWV RQAPGKGLEWVARIKRDGSEKYYVDSVKGRFTISRDN AKNSLYLQMNSLRAEDTAVYYCARDQGYKTPTDFDLW GRGTLVTVSSASTKGPSVFPLAPCSRSTSESTAALGC LVKDYFPEPVTVSWNSGALTSGVHTFPAVLQSSGLYS LSSVVTVPSSSLGTKTYTCNVDHKPSNTKVDKRVESK YGPPCPPCPAPEFLGGPSVFLFPPKPKDTLMISRTPE VTCVVVDVSQEDPEVQFNWYVDGVEVHNAKTKPREEQ FNSTYRVVSVLTVLHQDWLNGKEYKCKVSNKGLPSSI EKTISKAKGQPREPQVYTLPPSQEEMTKNQVSLTCLV KGFYPSDIAVEWESNGQPENNYKTTPPVLDSDGSFFL YSRLTVDKSRWQEGNVFSCSVMHEALHNHYTQKSLSL SLGK |
| 114 | MAB8 | HC Full-length IgG4 S228P | EVQLLESGGGLVQPGGSLRLSCAASGFTFASYAMVWV RQAPGKGLEWVSIISGSGGSTYYADSVKGRFTISRDN SKNTLYLQMNSLRAEDTAVYYCAKDPGYDSSRYYYSN YGMDVWGQGTTVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLM ISRTPEVTCVVVDVSQEDPEVQFNWYVDGVEVHNAKT KPREEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLDS DGSFFLYSRLTVDKSRWQEGNVFSCSVMHEALHNHYT QKSLSLSLGK |
| 115 | MAB9 | HC Full-length IgG4 S228P | EVQLLESGGGLVQPGGSLRLSCAASGFTFKSYAMVWV RQAPGKGLEWVSIISGSGGATYYADSVKGRFTISRDN SKNTLYLQMNSLRAEDTAVYYCAKDPGYDSSRYYYSN YGMDVWGQGTTVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLM ISRTPEVTCVVVDVSQEDPEVQFNWYVDGVEVHNAKT KPREEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLDS DGSFFLYSRLTVDKSRWQEGNVFSCSVMHEALHNHYT QKSLSLSLGK |
| 116 | MAB10 | HC Full-length IgG4 S228P | EVQLLESGGGLVQPGGSLRLSCAASGFTFSSVAMVWV RQAPGKGLEWVSAISGSGGATYYADSVKGRFTISRDN SKNTLYLQMNSLRAEDTAVYYCAKDPGYDSSRYYYSN YGMDVWGQGTTVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLM ISRTPEVTCVVVDVSQEDPEVQFNWYVDGVEVHNAKT KPREEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLDS DGSFFLYSRLTVDKSRWQEGNVFSCSVMHEALHNHYT QKSLSLSLGK |
| 117 | MAB11 | HC Full-length IgG4 S228P | EVQLLESGGGLVQPGGSLRLSCAASGFTFSSVAMVWV RQAPGKGLEWVSAISGSGGATYYADSVEGRFTISRDN SKNTLYLQMSSLRAEDTAVYYCAKDPGYDSSRYYYSN YGMDVWGQGTTVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLM ISRTPEVTCVVVDVSQEDPEVQFNWYVDGVEVHNAKT KPREEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLDS DGSFFLYSRLTVDKSRWQEGNVFSCSVMHEALHNHYT QKSLSLSLGK |

APPENDIX A: SEQUENCE REFERENCE TABLE

| SEQ ID NO | Molecule | Region | Sequence |
|---|---|---|---|
| 118 | MAB12 | HC Full-length IgG4 S228P | EVQLLESGGGLVQPGGSLRLSCAASGFTFSSVAMVWV RQAPGKGLEWVSAISGSGGATYYADSVEGRFTISRDN SKNTLYLQMNSLRAEDTAVYYCAKDPGYDSSRYYYSN YGMDVWGQGTTVTVSSASTKGPSVFPLAPCSRSTSES TAALGCLVKDYFPEPVTVSWNSGALTSGVHTFPAVLQ SSGLYSLSSVVTVPSSSLGTKTYTCNVDHKPSNTKVD KRVESKYGPPCPPCPAPEFLGGPSVFLFPPKPKDTLM ISRTPEVTCVVVDVSQEDPEVQFNWYVDGVEVHNAKT KPREEQFNSTYRVVSVLTVLHQDWLNGKEYKCKVSNK GLPSSIEKTISKAKGQPREPQVYTLPPSQEEMTKNQV SLTCLVKGFYPSDIAVEWESNGQPENNYKTTPPVLDS DGSFFLYSRLTVDKSRWQEGNVFSCSVMHEALHNHYT QKSLSLSLGK |
| 119 | MAB13 | HC Full-length IgG4 S228P | QVQLQQWGAGLLKPSETLSLTCAVYGGSFRGYYWEWI RQPPGKGLEWIGEISHSGSTNYNPSLKSRVTISVDTS KNQFSLKLSSVTAADTAVYYCARARPYREPYGMDVWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| 120 | MAB14 | HC Full-length IgG4 S228P | QVQLQQWGAGLLKPSETLSLTCAVYGGSFRGYYWEWS RQPPGKGLEWIGEISHSGSTNYNPSLKSRVTISVDTS KNQFSLKLSPVTAADTAVYYCARARPYREPYGMDVWG QGTTVTVSSASTKGPSVFPLAPCSRSTSESTAALGCL VKDYFPEPVTVSWNSGALTSGVHTFPAVLQSSGLYSL SSVVTVPSSSLGTKTYTCNVDHKPSNTKVDKRVESKY GPPCPPCPAPEFLGGPSVFLFPPKPKDTLMISRTPEV TCVVVDVSQEDPEVQFNWYVDGVEVHNAKTKPREEQF NSTYRVVSVLTVLHQDWLNGKEYKCKVSNKGLPSSIE KTISKAKGQPREPQVYTLPPSQEEMTKNQVSLTCLVK GFYPSDIAVEWESNGQPENNYKTTPPVLDSDGSFFLY SRLTVDKSRWQEGNVFSCSVMHEALHNHYTQKSLSLS LGK |
| 121 | MAB15 | HC Full-length IgG4 S228P | QVQLQQWGAGLLKPSETLSLTCAVYGGSFVKYYWSWI RQPPGKGLEWIGDIWHSGMTNYNPSLKSRVTISVDTS KNQFSLKLSSVTAADTAVYYCARGPGYDSSGYSRRFD PWGQGTLVTVSSASTKGPSVFPLAPCSRSTSESTAAL GCLVKDYFPEPVTVSWNSGALTSGVHTFPAVLQSSGL YSLSSVVTVPSSSLGTKTYTCNVDHKPSNTKVDKRVE SKYGPPCPPCPAPEFLGGPSVFLFPPKPKDTLMISRT PEVTCVVVDVSQEDPEVQFNWYVDGVEVHNAKTKPRE EQFNSTYRVVSVLTVLHQDWLNGKEYKCKVSNKGLPS SIEKTISKAKGQPREPQVYTLPPSQEEMTKNQVSLTC LVKGFYPSDIAVEWESNGQPENNYKTTPPVLDSDGSF FLYSRLTVDKSRWQEGNVFSCSVMHEALHNHYTQKSL SLSLGK |
| 122 | MAB1 | LC Full-length, human kappa constant | DIQMTQSPSSVSASVGDRVTITCRASQGISSWLAWYQ QKPGKAPKLLIYAASNLQSGVPSRFSGSGSGTDFTLT ISSLQPEDFATYYCQQASVPPFTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 122 | MAB2 | LC Full-length, human kappa constant | DIQMTQSPSSVSASVGDRVTITCRASQGISSWLAWYQ QKPGKAPKLLIYAASNLQSGVPSRFSGSGSGTDFTLT ISSLQPEDFATYYCQQASVPPFTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |

| APPENDIX A: SEQUENCE REFERENCE TABLE |||| 
|---|---|---|---|
| SEQ ID NO | Molecule | Region | Sequence |
| 123 | MAB3 | LC Full-length, human kappa constant | DIQMTQSPSSVSASVGDRVTITCRASQGISRWLAWYQ QKPGKAPKLLIYAASSLQSGVPSRFSGSGSGTDFTLT ISSLQPEDFATYYCQQANLLPFTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 123 | MAB4 | LC Full-length, human kappa constant | DIQMTQSPSSVSASVGDRVTITCRASQGISRWLAWYQ QKPGKAPKLLIYAASSLQSGVPSRFSGSGSGTDFTLT ISSLQPEDFATYYCQQANLLPFTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 124 | MAB5 | LC Full-length, human kappa constant | EIVMTQSPGTLSLSPGERATLSCRASQSVSSSYLAWY QQKPGQAPRLLIYGASNRATGIPDRFSGSGSGTDFTL TISRLEPEDFAVYYCQQLSSFPITFGGGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 124 | MAB6 | LC Full-length, human kappa constant | EIVMTQSPGTLSLSPGERATLSCRASQSVSSSYLAWY QQKPGQAPRLLIYGASNRATGIPDRFSGSGSGTDFTL TISRLEPEDFAVYYCQQLSSFPITFGGGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC |
| 125 | MAB7 | LC Full-length, human kappa constant | DIQMTQSPSSLSASVGDRVTITCQASQDITNYLNWYQ QKPGKAPKLLIYDASNLETGVPSRFSGSGSGTDFTFT ISSLQPEDIATYYCQQSDVLPITFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 126 | MAB8 | LC Full-length, human kappa constant | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 126 | MAB9 | LC Full-length, human kappa constant | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 126 | MAB10 | LC Full-length, human kappa constant | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 126 | MAB11 | LC Full-length, human kappa constant | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |
| 126 | MAB12 | LC Full-length, human kappa constant | DIQMTQSPSSLSASVGDRVTITCRASQSISSYLNWYQ QKPGKAPKLLIYGASSLQSGVPSRFSGSGSGTDFTLT ISSLQPEDFATYYCQQTYSLYTFGGGTKVEIKRTVAA PSVFIFPPSDEQLKSGTASVVCLLNNFYPREAKVQWK VDNALQSGNSQESVTEQDSKDSTYSLSSTLTLSKADY EKHKVYACEVTHQGLSSPVTKSFNRGEC |

| SEQ ID NO | Molecule | Region | Sequence |
|---|---|---|---|
| 127 | MAB13 | LC Full-length, human kappa constant | DIQLTQSPSSVSASVGDRVTITCRASQDISSWLAWYQ QKPGKAPKLLIYAASSLQSGVPSRFSGSGSGTDFTLT ISSLQPEDFATYYCQQELAFPRTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 127 | MAB14 | LC Full-length, human kappa constant | DIQLTQSPSSVSASVGDRVTITCRASQDISSWLAWYQ QKPGKAPKLLIYAASSLQSGVPSRFSGSGSGTDFTLT ISSLQPEDFATYYCQQELAFPRTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 128 | MAB15 | LC Full-length | DIQMTQSPSTLSASVGDRVTITCRASQSISSWLAWYQ QKPGKAPKLLIYKASSLESGVPSRFSGSGSGTEFTLT ISSLQPDDFATYYCQQLNSYPPTFGGGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 129 | hNRP-1 | GenBank Accession No. NM_003873.5 (corresponds to NP_003864.4). | ATGGAGAGGGGGCTGCCGCTCCTCTGCGCCGTGCTCG CCCTCGTCCTCGCCCCGGCCGGCGCTTTTCGCAACGA TAAATGTGGCGATACTATAAAAATTGAAAGCCCCGGG TACCTTACATCTCCTGGTTATCCTCATTCTTATCACC CAAGTGAAAAATGCGAATGGCTGATTCAGGCTCCGGA CCCATACCAGAGAATTATGATCAACTTCAACCCTCAC TTCGATTTGGAGGACAGAGACTGCAAGTATGACTACG TGGAAGTCTTCGATGGAGAAAATGAAAATGGACATTT TAGGGGAAAGTTCTGTGGAAAGATAGCCCCTCCTCCT GTTGTGTCTTCAGGGCCATTTCTTTTTATCAAATTTG TCTCTGACTACGAAACACATGGTGCAGGATTTTCCAT ACGTTATGAAATTTTCAAGAGAGGTCCTGAATGTTCC CAGAACTACACAACACTAGTGGAGTGATAAAGTCCC CCGGATTCCCTGAAAAATATCCCAACAGCCTTGAATG CACTTATATTGTCTTTGCGCCAAAGATGTCAGAGATT ATCCTGGAATTTGAAAGCTTTGACCTGGAGCCTGACT CAAATCCTCCAGGGGGGATGTTCTGTCGCTACGACCG GCTAGAAATCTGGGATGGATTCCCTGATGTTGGCCCT CACATTGGGCGTTACTGTGGACAGAAAACACCAGGTC GAATCCGATCCTCATCGGGCATTCTCTCCATGGTTTT TTACACCGACAGCGCGATAGCAAAAGAAGGTTTCTCA GCAAACTACAGTGTCTTGCAGAGCAGTGTCTCAGAAG ATTTCAAATGTATGGAAGCTCTGGGCATGGAATCAGG AGAAATTCATTCTGACCAGATCACAGCTTCTTCCCAG TATAGCACCAACTGGTCTGCAGAGCGCTCCCGCCTGA ACTACCCTGAGAATGGGTGGACTCCCGGAGAGGATTC CTACCGAGAGTGGATACAGGTAGACTTGGGCCTTCTG CGCTTTGTCACGGCTGTCGGGACACAGGGCGCCATTT CAAAAGAAACCAAGAAGAAATATTATGTCAAGACTTA CAAGATCGACGTTAGCTCCAACGGGGAAGACTGGATC ACCATAAAAGAAGGAAACAAACCTGTTCTCTTTCAGG GAAACACCAACCCCACAGATGTTGTGGTTGCAGTATT CCCCAAACCACTGATAACTCGATTTGTCCGAATCAAG CCTGCAACTTGGGAAACTGGCATATCTATGAGATTTG AAGTATACGGTTGCAAGATAACAGATTATCCTTGCTC TGGAATGTTGGGTATGGTGTCTGGACTTATTTCTGAC TCCCAGATCACATCATCCAACCAAGGGGACAGAAACT GGATGCCTGAAAACATCCGCCTGGTAACCAGTCGCTC TGGCTGGGCACTTCCACCCGCACCTCATTCCTACATC AATGAGTGGCTCCAAATAGACCTGGGGAGGAGAAGA TCGTGAGGGGCATCATCATTCAGGGTGGGAAGCACCG AGAGAACAAGGTGTTCATGAGGAAGTTCAAGATCGGG TACAGCAACAACGGCTCGGACTGGAAGATGATCATGG ATGACAGCAAACGCAAGGCGAAGTCTTTTGAGGGCAA CAACAACTATGATACACCTGAGCTGCGGACTTTTCCA GCTCTCTCCACGCGATTCATCAGGATCTACCCCGAGA GAGCCACTCATGGCGGACTGGGGCTCAGAATGGAGCT GCTGGGCTGTGAAGTGGAAGCCCCTACAGCTGGACCG ACCACTCCCAACGGGAACTTGGTGGATGAATGTGATG ACGACCAGGCCAACTGCCACAGTGGAACAGGTGATGA CTTCCAGCTCACAGGTGGCACCACTGTGCTGGCCACA GAAAAGCCCACGGTCATAGACAGCACCATACAATCAG AGTTTCCAACATATGGTTTTAACTGTGAATTTGGCTG GGGCTCTCACAAGACCTTCTGCCACTGGGAACATGAC |

APPENDIX A: SEQUENCE REFERENCE TABLE

| SEQ ID NO | Molecule | Region | Sequence |
|---|---|---|---|
| | | | AATCACGTGCAGCTCAAGTGGAGTGTGTTGACCAGCA<br>AGACGGGACCCATTCAGGATCACACAGGAGATGGCAA<br>CTTCATCTATTCCCAAGCTGACGAAAATCAGAAGGGC<br>AAAGTGGCTCGCCTGGTGAGCCCTGTGGTTTATTCCC<br>AGAACTCTGCCCACTGCATGACCTTCTGGTATCACAT<br>GTCTGGGTCCCACGTCGGCACACTCAGGGTCAAACTG<br>CGCTACCAGAAGCCAGAGGAGTACGATCAGCTGGTCT<br>GGATGGCCATTGGACACCAAGGTGACCACTGGAAGGA<br>AGGGCGTGTCTTGCTCCACAAGTCTCTGAAACTTTAT<br>CAGGTGATTTTCGAGGGCGAAATCGGAAAAGGAAACC<br>TTGGTGGGATTGCTGTGGATGACATTAGTATTAATAA<br>CCACATTTCACAAGAAGATTGTGCAAAACCAGCAGAC<br>CTGGATAAAAGAACCCAGAAATTAAAATTGATGAAA<br>CAGGGAGCACGCCAGGATACGAAGGTGAAGGAGAAGG<br>TGACAAGAACATCTCCAGGAAGCCAGGCAATGTGTTG<br>AAGACCTTAGACCCCATCCTCATCACCATCATAGCCA<br>TGAGTGCCCTGGGGGTCCTCCTGGGGGCTGTCTGTGG<br>GGTCGTGCTGTACTGTGCCTGTTGGCATAATGGGATG<br>TCAGAAAGAAACTTGTCTGCCCTGGAGAACTATAACT<br>TTGAACTTGTGGATGGTGTGAAGTTGAAAAAAGACAA<br>ACTGAATACACAGAGTACTTATTCGGAGGCATGA |
| 130 | hNRP-1<br>Protein | Genbank<br>NP_003864.4. | MERGLPLLCAVLALVLAPAGAFRNDKCGDTIKIESPG<br>YLTSPGYPHSYHPSEKCEWLIQAPDPYQRIMINFNPH<br>FDLEDRDCKYDYVEVFDGENENGHFRGKFCGKIAPPP<br>VVSSGPFLFIKFVSDYETHGAGFSIRYEIFKRGPECS<br>QNYTTPSGVIKSPGFPEKYPNSLECTYIVFAPKMSEI<br>ILEFESFDLEPDSNPPGGMFCRYDRLEIWDGFPDVGP<br>HIGRYCGQKTPGRIRSSSGILSMVFYTDSAIAKEGFS<br>ANYSVLQSSVSEDFKCMEALGMESGEIHSDQITASSQ<br>YSTNWSAERSRLNYPENGWTPGEDSYREWIQVDLGLL<br>RFVTAVGTQGAISKETKKKYYVKTYKIDVSSNGEDWI<br>TIKEGNKPVLFQGNTNPTDVVVAVFPKPLITRFVRIK<br>PATWETGISMRFEVYGCKITDYPCSGMLGMVSGLISD<br>SQITSSNQGDRNWMPENIRLVTSRSGWALPPAPHSYI<br>NEWLQIDLGEEKIVRGIIIQGGKHRENKVFMRKFKIG<br>YSNNGSDWKMIMDDSKRKAKSFEGNNNYDTPELRTFP<br>ALSTRFIRIYPERATHGGLGLRMELLGCEVEAPTAGP<br>TTPNGNLVDECDDDQANCHSGTGDDFQLTGGTTVLAT<br>EKPTVIDSTIQSEFPTYGFNCEFGWGSHKTFCHWEHD<br>NHVQLKWSVLTSKTGPIQDHTGDGNFIYSQADENQKG<br>KVARLVSPVVYSQNSAHCMTFWYHMSGSHVGTLRVKL<br>RYQKPEEYDQLVWMAIGHQGDHWKEGRVLLHKSLKLY<br>QVIFEGEIGKGNLGGIAVDDISINNHISQEDCAKPAD<br>LDKKNPEIKIDETGSTPGYEGEGEGDKNISRKPGNVL<br>KTLDPILITIIAMSALGVLLGAVCGVVLYCACWHNGM<br>SERNLSALENYNFELVDGVKLKKDKLNTQSTYSEA |
| 131 | cNRP-1 | DNA:<br>Genbank<br>Acc No.<br>XM_005564935.2 | ATGGAGAAGGGGTTGCCGCTCCTCTGCGCCGCGCTCG<br>CCCTCGCCCTCGCCCCGGCCGGCGCTTTTCGCAACGA<br>TAAATGTGGCGATACTATAAAAATTGAAAGCCCCGGG<br>TACCTTACATCTCCTGGTTATCCTCATTCTTATCACC<br>CAAGTGAAAAATGTGAATGGCTGATTCAGGCTCCGGA<br>CCCATACCAGAGAATTATGATCAACTTCAACCCTCAC<br>TTCGATTTGGAGGACAGAGATTGCAAGTATGACTACG<br>TGGAAGTCTTCGATGGAGAAAATGAAAATGGACGTTT<br>ATGGGGAAAGTTCTGTGGAAAGATAGCCCCTCCTCCT<br>GTTGTGTCTTCAGGGCAATTTCTTTTTATCAAATTTG<br>TCTCTGACTACGAAACACACGGTGCAGGATTTTCCAT<br>ACGTTATGAAATTTTCAAGAGAGGTCCTGAATGTTCC<br>CAGAACTACACAACACCTAGTGGAGTGATAAAGTCCC<br>CCGGATTCCCTGAAAAATATCCCAACAGCCTTGAATG<br>CACTTATATTGTCTTTGCACCAAAGATGTCAGAGATT<br>ATCCTGGAATTTGAAAGCTTTGACCTGGAGCCTGACT<br>CAAATCCTCCAGGGGGGATGTTCTGTCGCTACGACCG<br>GCTGGAAATCTGGGATGGATTCCCTGACGTTGGCCCT<br>CACATTGGGCGTTACTGTGGACAGAAAACACCAGGTC<br>GAATCCGATCCTCATCGGGCATTCTCTCCATGGTTTT<br>TTACACCGACAGCGCAATAGCAAAAGAAGGTTTCTCA<br>GCAAACTACAGTGTCTTGCAGAGCAGTGTCTCAGAAG<br>ATTTCAAATGTATGGAAGCTGTGGGCATGGAATCAGG<br>AGAAATTCATTCTGACCAGATCACAGCTTCTTCCCAG<br>TACAGCACCAACTGGTCTGCAGAGCGCTCCCGCCTGA<br>ACTATCCTGAGAATGGGTGGACTCCCGGAGAAGATTC<br>CTACCGAGAGTGGATACAGGTGGACTTGGGCCTTCTA |

APPENDIX A: SEQUENCE REFERENCE TABLE

| SEQ ID NO | Molecule | Region | Sequence |
|---|---|---|---|
| | | | CGCTTCGTTACGGCTGTCGGGACACAGGGCGCCATTT<br>CAAAAGAAACCAAGAAGAAATATTATGTCAAGACTTA<br>CAAAATTGACATTAGCTCCAACGGGGAAGACTGGATC<br>ACCATAAAAGAAGGAAACAAACCTGTTCTCTTTCAGG<br>GAAACACCAACCCCACAGACGTTGTGGTTGCAGTATT<br>CCCCAAGCCACTGATAACTCGATTTGTCCGAATCAAG<br>CCTGCAACTTGGGAAACTGGCATATCTCTGAGATTTG<br>AAGTATATGGTTGCAAGATAACAGATTATCCTTGCTC<br>CGGAATGTTGGGTATGGTGTCTGGACTTATTTCTGAC<br>TCCCAGATCACATCATCCAACCAAGGGGACAGAAACT<br>GGATGCCTGAAAACATCCGCCTGGTAACCAGTCGCTC<br>CGGCTGGGCACTGCCACCCGCACCTCATTCCTACGTC<br>AATGAGTGGCTCCAAATAGACCTGGGGGAGGAGAAGA<br>TCGTGAGGGGCATCATCATTCAGGGTGGGAAGCACCG<br>AGAGAACAAGGTATTCATGAGGAAGTTCAAGATCGGG<br>TACAGCAACAACGGCTCCGACTGGAAGATGATCATGG<br>ACGACAGCAAACGCAAGGCAAAGTCTTTTGAGGGCAA<br>CAACAACTATGACACACCTGAGCTGCGGACTTTTCCA<br>GCTCTCTCCACGCGATTCATCAGGATCTACCCCGAGA<br>GAGCCACTCATGGCGGACTGGGGCTCCGAATGGAGCT<br>GCTGGGCTGTGAAGTGGAAGCCCCTACAGCTGGACCG<br>ACCACTCCCAACGGGAACCCGGTGGATGAATGTGATG<br>ACGACCAGGCCAACTGCCACAGTGGAACAGGTGATGA<br>CTTCCAGCTCACAGGTGGCACCACTGTGCTGGCCACA<br>GAAAAGCCCACGGTCATAGACAGCACCATACAATCAG<br>AGTTTCCTACATATGGTTTTAACTGTGAATTTGGCTG<br>GGGCTCTCACAAGACCTTCTGCCACTGGGAACATGAC<br>AATCACGTGCAGCTCAAGTGGAGTGTGTTGACCAGCA<br>AGACGGGACCCATTCAGGATCACACAGGAGATGGCAA<br>CTTCATCTATTCCCAAGCTGATGAAAATCAGAAGGGC<br>AAAGTGGCTCGCCTGGTGAGCCCTGTGGTTTATTCCC<br>AGAACTCTGCCCACTGCATGACCTTCTGGTATCACAT<br>GTCTGGGTCCCACGTCGGCACACTCAGGGTCAAACTG<br>CGCTACCAGAAGCCAGAGGAGTACGATCAGCTGGTCT<br>GGATGGCCATTGGACACCAAGGTGACCACTGGAAGGA<br>AGGGCGTGTCTTGCTTCACAAGTCTCTGAAACTTTAT<br>CAGGTGATTTTCGAGGGCGAAATCGGAAAGGAAACC<br>TTGGTGGGATTGCTGTGGATGACATTAGTATCAATAA<br>CCACATTTCACAAGAAGATTGTGCAAAACCAGCAGAC<br>CTGGATAAAAAGAACCCAGAAATTAAAATTGATGAAA<br>CAGGGAGCACACCAGGATATGAAGGTGAAGGAGAAGG<br>TGACAAGAACATCTCCAGGAAACCAGGCAATGTGTTG<br>AAGACCTTAGACCCCATCCTCATCACCATCATAGCCA<br>TGAGCGCCCTGGGGGTCCTCCTGGGGGCTGTGTGCGG<br>GGTCGTGCTGTACTGTGCCTGTTGGCATAATGGGATG<br>TCAGAAAGAAACTTGTCTGCCCTGGAGAACTATAACT<br>TTGAACTTGTGGACGGTGTGAAGTTGAAAAAAGACAA<br>ACTGAATACACAGAGTACTTATTCGGAGGCATGA |
| 132 | cNRP-1 | Protein:<br>UniProtK<br>B-G7PEQ1 | MEKGLPLLCAALALALAPAGAFRNDKCGDTIKIESPG<br>YLTSPGYPHSYHPSEKCEWLIQAPDPYQRIMINFNPH<br>FDLEDRDCKYDYVEVFDGENENGRLWGKFCGKIAPPP<br>VVSSGQFLFIKFVSDYETHGAGFSIRYEIFKRGPECS<br>QNYTTPSGVIKSPGFPEKYPNSLECTYIVFAPKMSEI<br>ILEFESFDLEPDSNPPGGMFCRYDRLEIWDGFPDVGP<br>HIGRYCGQKTPGRIRSSSGILSMVFYTDSAIAKEGFS<br>ANYSVLQSSVSEDFKCMEAVGMESGEIHSDQITASSQ<br>YSTNWSAERSRLNYPENGWTPGEDSYREWIQVDLGLL<br>RFVTAVGTQGAISKETKKKYYVKTYKIDISSNGEDWI<br>TIKEGNKPVLFQGNTNPTDVVVAVFPKPLITRFVRIK<br>PATWETGISLRFEVYGCKITDYPCSGMLGMVSGLISD<br>SQITSSNQGDRNWMPENIRLVTSRSGWALPPAPHSYV<br>NEWLQIDLGEEKIVRGIIQGGKHRENKVFMRKFKIG<br>YSNNGSDWKMIMDDSKRKAKSFEGNNNYDTPELRTFP<br>ALSTRFIRIYPERATHGGLGLRMELLGCEVEAPTAGP<br>TTPNGNPVDECDDDQANCHSGTGDDFQLTGGTTVLAT<br>EKPTVIDSTIQSEFPTYGFNCEFGWGSHKTFCHWEHD<br>NHVQLKWSVLTSKTGPIQDHTGDGNFIYSQADENQKG<br>KVARLVSPVVYSQNSAHCMTFWYHMSGSHVGTLRVKL<br>RYQKPEEYDQLVWMAIGHQGDHWKEGRVLLHKSLKLY<br>QVIFEGEIGKGNLGGIAVDDISINNHISQEDCAKPAD<br>LDKKNPEIKIDETGSTPGYEGEGEGDKNISRKPGNVL<br>KTLDPILITIIAMSALGVLLGAVCGVVLYCACWHNGM<br>SERNLSALENYNFELVDGVKLKKDKLNTQSTYSEA |

APPENDIX A: SEQUENCE REFERENCE TABLE

| SEQ ID NO | Molecule | Region | Sequence |
|---|---|---|---|
| 133 | mNRP-1 | GenBank Acc. No. NM008737 | ATGGAGAGGGGGCTGCCGTTGCTGTGCGCCACGCTCG CCCTTGCCCTCGCCCTGGCGGGCGCTTTCCGCAGCGA CAAATGTGGCGGGACCATAAAAATCGAAAACCCAGGG TACCTCACATCTCCCGGTTACCCTCATTCTTACCATC CAAGTGAGAAGTGTGAATGGCTAATCCAAGCTCCGGA ACCCTACCAGAGAATCATGATCAACTTCAACCCACAT TTCGATTTGGAGGACAGAGACTGCAAGTATGACTACG TGGAAGTAATCGATGGGGAGAATGAAGGCGGCCGCCT GTGGGGGAAGTTCTGTGGGAAGATTGCACCTTCTCCT GTGGTGTCTTCAGGGCCCTTTCTCTTCATCAAATTTG TCTCTGACTATGAGACACATGGGGCAGGGTTTTCCAT CCGCTATGAAATCTTCAAGAGAGGGCCCGAATGTTCT CAGAACTATACAGCACCTACTGGAGTGATAAAGTCCC CTGGGTTCCCTGAAAAATACCCCAACAGCTTGGAGTG CACCTACATCATCTTTGCACCAAAGATGTCTGAGATA ATCCTGGAGTTTGAAAGTTTTGACCTGGAGCAAGACT CGAATCCTCCCGGAGGAATGTTCTGTCGCTATGACCG GCTGGAGATCTGGGATGGATTCCCTGAAGTTGGCCCT CACATTGGGCGTTATTGTGGGCAGAAAACTCCTGGCC GGATCCGCTCCTCTTCAGGCGTTCTATCCATGGTCTT TTACACTGACAGCGCAATAGCAAAAGAAGGTTTCTCA GCCAACTACAGTGTGCTACAGAGCAGCATCTCTGAAG ATTTTAAGTGTATGGAGGCTCTGGGCATGGAATCTGG AGAGATCCATTCTGATCAGATCACTGCATCTTCACAG TATGGTACCAACTGGTCTGTAGAGCGCTCCCGCCTGA ACTACCCTGAAAATGGGTGGACTCCAGGAGAAGACTC CTACAAGGAGTGGATCCAGGTGGACTTGGGCCTCCTG CGATTCGTTACTGCTGTAGGGACACAGGGTGCCATTT CCAAGGAAACCAAGAAGAAATATTATGTCAAGACTTA CAGAGTAGACATCAGCTCCAACGGAGAGGACTGGATC TCCCTGAAAGAGGGAAATAAAGCCATTATCTTTCAGG GAAACACCAACCCCACAGATGTTGTCTTAGGAGTTTT CTCCAAACCACTGATAACTCGATTTGTCCGAATCAAA CCTGTATCCTGGGAAACTGGTATATCTATGAGATTTG AAGTTTATGGCTGCAAGATAACAGATTATCCTTGCTC TGGAATGTTGGGCATGGTGTCTGGACTTATTTCAGAC TCCCAGATTACAGCATCCAATCAAGCCGACAGGAATT GGATGCCAGAAAACATCCGTCTGGTGACCAGTCGTAC CGGCTGGGCACTGCCACCCTCACCCCACCCATACACC AATGAATGGCTCCAAGTGGACCTGGGAGATGAGAAGA TAGTAAGAGGTGTCATCATTCAGGGTGGGAAGCACCG AGAAAACAAGGTGTTCATGAGGAAGTTCAAGATCGCC TATAGTAACAATGGCTCTGACTGGAAAACTATCATGG ATGACAGCAAGCGCAAGGCTAAGTCGTTCGAAGGCAA CAACAACTATGACACACCTGAGCTTCGGACGTTTTCA CCTCTCTCCACAAGGTTCATCAGGATCTACCCTGAGA GAGCCACACACAGTGGGCTTGGGCTGAGGATGGAGCT ACTGGGCTGTGAAGTGGAAGCACCTACAGCTGGACCA ACCACACCCAATGGGAACCCAGTGGATGAGTGTGACG ACGACCAGGCCAACTGCCACAGTGGCACAGGTGATGA CTTCCAGCTCACAGGAGGCACCACTGTCCTGGCCACA GAGAAGCCAACCATTATAGACAGCACCATCCAATCAG AGTTCCCGACATACGGTTTTAACTGCGAGTTTGGCTG GGGCTCTCACAAGACATTCTGCCACTGGGAGCATGAC AGCCATGCACAGCTCAGGTGGAGTGTGCTGACCAGCA AGACAGGGCCGATTCAGGACCATACAGGAGATGGCAA CTTCATCTATTCCCAAGCTGATGAAAATCAGAAAGGC AAAGTAGCCCGCCTGGTGAGCCCTGTGGTCTATTCCC AGAGCTCTGCCCACTGTATGACCTTCTGGTATCACAT GTCCGGCTCTCATGTGGGTACACTGAGGGTCAAACTA CGCTACCAGAAGCCAGAGGAATATGATCAACTGGTCT GGATGGTGGTTGGGCACCAAGGAGACCACTGGAAAGA AGGACGTGTCTTGCTGCACAAATCTCTGAAACTATAT CAGGTTATTTTGAAGGTGAAATCGGAAAAGGAAACC TTGGTGGAATTGCTGTGGATGATATCAGTATTAACAA CCATATTTCTCAGGAAGACTGTGCAAAACCAACAGAC CTAGATAAAAAGAACACAGAAATTAAAATTGATGAAA CAGGGAGCACTCCAGGATATGAAGGAGAAGGGGAAGG TGACAAGAACATCTCCAGGAAGCCAGGCAATGTGCTT AAGACCCTGGATCCCATCCTGATCACCATCATAGCCA TGAGTGCCCTGGGAGTACTCCTGGGTGCAGTCTGTGG AGTTGTGCTGTACTGTGCCTGTTGGCACAATGGGATG TCAGAAAGGAACCTATCTGCCCTGGAGAACTATAACT TTGAACTTGTGGATGGTGTAAAGTTGAAAAAAGATAA ACTGAACCCACAGAGTAATTACTCAGAGGCGTGA |

APPENDIX A: SEQUENCE REFERENCE TABLE

| SEQ ID NO | Molecule | Region | Sequence |
|---|---|---|---|
| 134 | mNRP-1 | UniProtKB-P97333 | MERGLPLLCATLALALALAGAFRSDKCGGTIKIENPG<br>YLTSPGYPHSYHPSEKCEWLIQAPEPYQRIMINFNPH<br>FDLEDRDCKYDYVEVIDGENEGGRLWGKFCGKIAPSP<br>VVSSGPFLFIKFVSDYETHGAGFSIRYEIFKRGPECS<br>QNYTAPTGVIKSPGFPEKYPNSLECTYIIFAPKMSEI<br>ILEFESFDLEQDSNPPGGMFCRYDRLEIVVDGFPEVG<br>PHIGRYCGQKTPGRIRSSSGVLSMVFYTDSAIAKEGF<br>SANYSVLQSSISEDFKCMEALGMESGEIHSDQITASS<br>QYGTNWSVERSRLNYPENGWTPGEDSYKEWIQVDLGL<br>LRFVTAVGTQGAISKETKKKYYVKTYRVDISSNGEDW<br>ISLKEGNKAIIFQGNTNPTDVVLGVFSKPLITRFVRI<br>KPVSWETGISMRFEVYGCKITDYPCSGMLGMVSGLIS<br>DSQITASNQADRNWMPENIRLVTSRTGWALPPSPHPY<br>TNEWLQVDLGDEKIVRGVIIQGGKHRENKVFMRKFKI<br>AYSNNGSDWKTIMDDSKRKAKSFEGNNNYDTPELRTF<br>SPLSTRFIRIYPERATHSGLGLRMELLGCEVEAPTAG<br>PTTPNGNPVDECDDDQANCHSGTGDDFQLTGGTTVLA<br>TEKPTIIDSTIQSEFPTYGFNCEFGWGSHKTFCHWEH<br>DSHAQLRWSVLTSKTGPIQDHTGDGNFIYSQADENQK<br>GKVARLVSPVVYSQSSAHCMTFWYHMSGSHVGTLRVK<br>LRYQKPEEYDQLVWMVVGHQGDHWKEGRVLLHKSLKL<br>YQVIFEGEIGKGNLGGIAVDDISINNHISQEDCAKPT<br>DLDKKNTEIKIDETGSTPGYEGEGEGDKNISRKPGNV<br>LKTLDPILITIIAMSALGVLLGAVCGVVLYCACWHNG<br>MSERNLSALENYNFELVDGVKLKKDKLNPQSNYSEA |
| 135 | rNRP-1 | UniProtKB-Q9QWJ9 | MERGLPLLCATLALALALAGAFRSDKCGGTIKIENPG<br>YLTSPGYPHSYHPSEKCEWLIQAPEPYQRIMINFNPH<br>FDLEDRDCKYDYVEVIDGENEGGRLWGKFCGKIAPSP<br>VVSSGPFLFIKFVSDYETHGAGFSIRYEIFKRGPECS<br>QNYTAPTGVIKSPGFPEKYPNSLECTYIIFAPKMSEI<br>ILEFESFDLEQDSNPPGGVFCRYDRLEIWDGFPEVGP<br>HIGRYCGQKTPGRIRSSSGILSMVFYTDSAIAKEGFS<br>ANYSVLQSSISEDFKCMEALGMESGEIHSDQITASSQ<br>YGTNWSVERSRLNYPENGWTPGEDSYREWIQVDLGLL<br>RFVTAVGTQGAISKETKKKYYVKTYRVDISSNGEDWI<br>TLKEGNKAIIFQGNTNPTDVVFGVFPKPLITRFVRIK<br>PASWETGISMRFEVYGCKITDYPCSGMLGMVSGLISD<br>SQITASNQGDRNWMPENIRLVTSRTGWALPPSPHPYI<br>NEWLQVDLGDEKIVRGVIIQGGKHRENKVFMRKFKIA<br>YSNNGSDWKMIMDDSKRKAKSFEGNNNYDTPELRAFT<br>PLSTRFIRIYPERATHSGLGLRMELLGCEVEVPTAGP<br>TTPNGNPVDECDDDQANCHSGTGDDFQLTGGTTVLAT<br>EKPTIIDSTIQSEFPTYGFNCEFGWGSHKTFCHWEHD<br>SHAQLRWRVLTSKTGPIQDHTGDGNFIYSQADENQKG<br>KVARLVSPVVYSQSSAHCMTFWYHMSGSHVGTLRVKL<br>HYQKPEEYDQLVWMVVGHQGDHWKEGRVLLHKSLKLY<br>QVIFEGEIGKGNLGGIAVDDISINNHIPQEDCAKPTD<br>LDKKNTEIKIDETGSTPGYEEGKGDKNISRKPGNVLK<br>TLDPILITIIAMSALGVLLGAVCGVVLYCACWHNGMS<br>ERNLSALENYNFELVDGVKLKKDKLNPQSNYSEA |
| 136 | MABs 8-12 | VHCDR2 Consensus | $X_1$ISGSGG$X_2$TYYADSV$X_3$G, wherein $X_1$ is I or A, $X_2$ is S or A, and $X_3$ is K or E |
| 137 | MABs 8-12 | VHCDR1 Consensus | FTF$X_1$S$X_2$AMV, wherein $X_1$ is A, K, or S, $X_2$ is Y or V |
| 138 | MABs 3-4 | VHCDR3 Consensus | ARDLGYYGSGMHX, wherein X is A or V |
| 139 | MABs 5-6 | VHCDR3 Consensus | ARDRGMYYASGFXP, wherein X is G or N |
| 140 | | Linker consensus | (GGGGS)$_n$, wherein n is an integer |
| 141 | anti-NRP Antibody SEC10 | IgG1 | EVQLVESGGGLVQPGGSLRLSCAASGFTFSSYAMSWV<br>RQAPGKGLEWVSQISPAGGYTNYADSVKGRFTISADT<br>SKNTAYLQMNSLRAEDTAVYYCARGELPYYRMSKVMD<br>VWGQGTLVTVSSASTKGPSVFPLAPSSKSTSGGTAAL<br>GCLVKDYFPEPVTVSWNSGALTSGVHTFPAVLQSSGL<br>YSLSSVVTVPSSSLGTQTYICNVNHKPSNTKVDKKVE<br>PKSCDKTHTCPPCPAPELLGGPSVFLFPPKPKDTLMI |

| SEQ ID NO | Molecule | Region | Sequence |
|---|---|---|---|
| | | | SRTPEVTCVVVDVSHEDPEVKFNWYVDGVEVHNAKTK PREEQYNSTYRVVSVLTVLHQDWLNGKEYKCKVSNKA LPAPIEKTISKAKGQPREPQVYTLPPSREEMTKNQVS LTCLVKGFYPSDIAVEWESNGQPENNYKTTPPVLDSD GSFFLYSKLTVDKSRWQQGNVFSCSVMHEALHNHYTQ KSLSLSPGK |
| 142 | anti-NRP Antibody SEC10 | Kappa light chain | DIQMTQSPSSLSASVGDRVTITCRASQYFSSYLAWYQ QKPGKAPKLLIYGASSRASGVPSRFSGSGSGTDFTLT ISSLQPEDFATYYCQQYLGSPPTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 143 | Human NRP-1 | UniProt O14786. Has minor SNP, V179 | MERGLPLLCAVLALVLAPAGAFRNDKCGDTIKIESPG YLTSPGYPHSYHPSEKCEWLIQAPDPYQRIMINFNPH FDLEDRDCKYDYVEVFDGENENGHFRGKFCGKIAPPP VVSSGPFLFIKFVSDYETHGAGFSIRYEIFKRGPECS QNYTTPSGVIKSPGFPEKYPNSLECTYIVFVPKMSEI ILEFESFDLEPDSNPPGGMFCRYDRLEIWDGFPDVGP HIGRYCGQKTPGRIRSSSGILSMVFYTDSAIAKEGFS ANYSVLQSSVSEDFKCMEALGMESGEIHSDQITASSQ YSTNWSAERSRLNYPENGWTPGEDSYREWIQVDLGLL RFVTAVGTQGAISKETKKKYYVKTYKIDVSSNGEDWI TIKEGNKPVLFQGNTNPTDVVVAVFPKPLITRFVRIK PATWETGISMRFEVYGCKITDYPCSGMLGMVSGLISD SQITSSNQGDRNWMPENIRLVTSRSGWALPPAPHSYI NEWLQIDLGEEKIVRGIIIQGGKHRENKVFMRKFKIG YSNNGSDWKMIMDDSKRKAKSFEGNNNYDTPELRTFP ALSTRFIRIYPERATHGGLGLRMELLGCEVEAPTAGP TTPNGNLVDECDDDQANCHSGTGDDFQLTGGTTVLAT EKPTVIDSTIQSEFPTYGFNCEFGWGSHKTFCHWEHD NHVQLKWSVLTSKTGPIQDHTGDGNFIYSQADENQKG KVARLVSPVVYSQNSAHCMTFWYHMSGSHVGTLRVKL RYQKPEEYDQLVWMAIGHQGDHWKEGRVLLHKSLKLY QVIFEGEIGKGNLGGIAVDDISINNHISQEDCAKPAD LDKKNPEIKIDETGSTPGYEGEGEGDKNISRKPGNVL KTLDPILITIIAMSALGVLLGAVCGVVLYCACWHNGM SERNLSALENYNFELVDGVKLKKDKLNTQSTYSEA |
| 144 | SEC3 | light chain | DIQMTQSPSSLSASVGDRVTITCRASQDVSTAVAWYQ QKPGKAPKLLIYSASFLYSGVPSRFSGSGSGTDFTLT ISSLQPEDFATYYCQQAWAYLPTFGQGTKVEIKRTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| 145 | SEC3 | Heavy Chain | EVQLVESGGGLVQPGGSLRLSCAASGFTISGYGIHWV RQAPGKGLEWVAYIYPDSGYTDYADSVKGRFTISADT SKNTAYLQMNSLRAEDTAVYYCAREDFRNRRRLWYVM DYWGQGTLVTVSSASTKGPSVFPLAPSSKSTSGGTAA LGCLVKDYFPEPVTVSWNSGALTSGVHTFPAVLQSSG LYSLSSVVTVPSSSLGTQTYICNVNHKPSNTKVDKKV EPKSCDKTHTCPPCPAPELLGGPSVFLFPPKPKDTLM ISRTPEVTCVVVDVSHEDPEVKFNWYVDGVEVHNAKT KPREEQYNSTYRVVSVLTVLHQDWLNGKEYKCKVSNK ALPAPIEKTISKAKGQPREPQVYTLPPSREEMTKNQV SLTCLVKGFYPSDIAVEWESNGQPENNYKTTPPVLDS DGSFFLYSKLTVDKSRWQQGNVFSCSVMHEALHNHYT QKSLSLSPGK |

What is claimed is:

1. An isolated antigen binding protein (ABP) that specifically binds human NRP-1 (hNRP-1; SEQ ID NO:130), wherein the ABP comprises the following six CDR sequences:
   (a) a CDR-H3 having the sequence set forth in SEQ ID NO:47;

(b) a CDR-H2 having the sequence $X_1$ISGSGG$X_2$TYYADSV$X_3$G, wherein $X_1$ is I or A, $X_2$ is S or A, and $X_3$ is K or E, as set forth in SEQ ID NO:136;

(c) a CDR-H1 having the sequence FTF$X_1$S$X_2$AMV, wherein $X_1$ is A, K, or S and $X_2$ is Y or V, as set forth in SEQ ID NO:137;

(d) a CDR-L3 having the sequence set forth in SEQ ID NO:81;

(e) a CDR-L2 having the sequence set forth in SEQ ID NO:71; and (f) a CDR-L1 having the sequence set forth in SEQ ID NO:63.

2. The ABP of claim 1, wherein the ABP comprises:

(a) a CDR-H3 of SEQ ID NO:47, a CDR-H2 of SEQ ID NO:27, a CDR-H1 of SEQ ID NO:12, a CDR-L3 of SEQ ID NO:81, a CDR-L2 of SEQ ID NO:71, and a CDR-L1 of SEQ ID NO:63;

(b) a CDR-H3 of SEQ ID NO:47, a CDR-H2 of SEQ ID NO:28, a CDR-H1 of SEQ ID NO:13, a CDR-L3 of SEQ ID NO:81, a CDR-L2 of SEQ ID NO:71, and a CDR-L1 of SEQ ID NO:63;

(c) a CDR-H3 of SEQ ID NO:47, a CDR-H2 of SEQ ID NO:29, a CDR-H1 of SEQ ID NO:14, a CDR-L3 of SEQ ID NO:81, a CDR-L2 of SEQ ID NO:71, and a CDR-L1 of SEQ ID NO:63; or (d) a CDR-H3 of SEQ ID NO:47, a CDR-H2 of SEQ ID NO:30, a CDR-H1 of SEQ ID NO:14, a CDR-L3 of SEQ ID NO:81, a CDR-L2 of SEQ ID NO:71, and a CDR-L1 of SEQ ID NO:63.

3. The ABP of claim 2, wherein:

(a) the ABP of claim 2(a) comprises a $V_H$ sequence of SEQ ID NO:92 and a $V_L$ sequence of SEQ ID NO:104;

(b) the ABP of claim 2(b) comprises a $V_H$ sequence of SEQ ID NO:93 and a $V_L$ sequence of SEQ ID NO:104;

(c) the ABP of claim 2(c) comprises a $V_H$ sequence of SEQ ID NO:94 and a $V_L$ sequence of SEQ ID NO:104;

(d) the ABP of claim 2(d) comprises a $V_H$ sequence of SEQ ID NO:95 and a $V_L$ sequence of SEQ ID NO:104; or (e) the ABP of claim 2(d) comprises a $V_H$ sequence of SEQ ID NO:96 and a $V_L$ sequence of SEQ ID NO:104.

4. The ABP of claim 2, wherein the ABP of claim 2(d) comprises a $V_H$ sequence of SEQ ID NO:96 and a $V_L$ sequence of SEQ ID NO:104.

5. The ABP of claim 3, wherein:

(a) the ABP of claim 2 (a) comprises a heavy chain of SEQ ID NO:114 and a light chain of SEQ ID NO:126;

(b) the ABP of claim 2(b) comprises a heavy chain of SEQ ID NO:115 and a light chain of SEQ ID NO:126;

(c) the ABP of claim 2(c) comprises a heavy chain of SEQ ID NO:116 and a light chain of SEQ ID NO:126;

(d) the ABP of claim 2(d) comprises a heavy chain of SEQ ID NO:117 and a light chain of SEQ ID NO:126; or (e) the ABP of claim 2(d) comprises a heavy chain of SEQ ID NO:118 and a light chain of SEQ ID NO:126.

6. The ABP of claim 3, wherein the ABP of claim 2(d) comprises a heavy chain of SEQ ID NO:118 and a light chain of SEQ ID NO:126.

7. The ABP of claim 3, wherein the ABP of claim 2(d) consists of a heavy chain of SEQ ID NO:118 and a light chain of SEQ ID NO:126.

8. The ABP of claim 1, wherein the ABP competes for binding to human NRP-1 with an antibody selected from the group consisting of MAB1, MAB2, MAB3, MAB4, MAB5, MAB6, MAB7, MAB8, MAB9, MAB10, MAB11, MAB12, MAB13, MAB14, and MAB15.

9. The ABP of claim 1, wherein the ABP specifically antagonizes human NRP-1 binding to a neuropilin-1 ligand and modulating an immune response in a human.

10. The ABP of claim 1, wherein the ABP specifically binds one or more residues on human NRP-1(SEQ ID NO:130) chosen from the group consisting of specifically binds one or more of human NRP-1 residues selected from the group consisting of Y297, T316, D320, E348, T349, K350, K351, K352, Y353, Y354, E412, T413, G414, and I415.

11. The ABP of claim 1, wherein the ABP specifically binds to NRP-1 from humans, mice, and cynomolgus monkeys.

12. The ABP of claim 1, wherein the ABP binds to a different epitope on human NRP-1 than the epitope on human NRP-1 to which SEC10 binds.

13. The ABP of claim 1, wherein the ABP specifically binds to the b1 domain of human NRP-1.

14. The ABP of claim 1, wherein the ABP antagonizes the interaction between a human NRP-1 polypeptide and one or both of a human vascular endothelial cell growth factor (VEGF) polypeptide and a human semaphorin (SEMA) polypeptide.

15. The ABP of claim 14, wherein the human semaphorin polypeptide is a human SEMA3 polypeptide.

16. The ABP of claim 1, wherein the ABP does not substantially bind platelets.

17. The ABP of claim 1, wherein the ABP inhibits Treg suppression in a human subject.

18. The ABP of claim 1, wherein the ABP comprises two antigen-binding domains.

19. The ABP of claim 1, wherein the ABP comprises a CDR-H3 of SEQ ID NO:47, a CDR-H2 of SEQ ID NO:30, a CDR-H1 of SEQ ID NO:14, a CDR-L3 of SEQ ID NO:81, a CDR-L2 of SEQ ID NO:71, and a CDR-L1 of SEQ ID NO:63.

20. A pharmaceutical composition comprising an ABP of claim 1 and a pharmaceutically acceptable excipient.

* * * * *

SEQUENCE LISTING

<160> NUMBER OF SEQ ID NOS: 148

<210> SEQ ID NO 1
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Gln Val Gln Leu Val Gln Ser Gly Ala Gly Val Lys Lys Pro Gly Ala
1               5                   10                  15

Ser Val Lys Val Ser Cys Lys Ala Ser Gly
            20                  25

<210> SEQ ID NO 2
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 3
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln Ala Gln Leu Val Gln Ser Gly Ala Glu Val Lys Lys Pro Gly Ala
1               5                   10                  15

Ser Val Lys Val Ser Cys Lys Ala Ser Gly
            20                  25

<210> SEQ ID NO 4
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gln Val Gln Leu Val Gln Ser Gly Ala Lys Val Lys Lys Pro Gly Ala
1               5                   10                  15

Ser Val Lys Val Ser Cys Lys Ala Ser Gly
            20                  25

<210> SEQ ID NO 5
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 6
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 7
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly
            20                  25

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Tyr Thr Phe Arg Ser Tyr Tyr Met Leu
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Tyr Thr Phe Ser Arg Tyr Tyr Met His
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 10

Tyr Thr Phe Thr Ser Tyr Tyr Met His
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Phe Thr Phe Ser Ser Tyr Trp Met Glu
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Phe Thr Phe Ala Ser Tyr Ala Met Val
1               5

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Phe Thr Phe Lys Ser Tyr Ala Met Val
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Phe Thr Phe Ser Ser Val Ala Met Val
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Ser Phe Arg Gly Tyr Tyr Trp Glu
```

```
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Ser Phe Val Lys Tyr Tyr Trp Ser
1               5

<210> SEQ ID NO 17
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Trp Val Arg Gln Ala Pro Gly Gln Gly Leu Glu Trp Met Gly
1               5                   10

<210> SEQ ID NO 18
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Trp Val Arg Gln Val Pro Gly Gln Gly Leu Glu Trp Met Gly
1               5                   10

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Trp Val Arg Gln Ala Pro Gly Lys Gly Leu Glu Trp Val Ala
1               5                   10

<210> SEQ ID NO 20
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Trp Val Arg Gln Ala Pro Gly Lys Gly Leu Glu Trp Val Ser
1               5                   10

<210> SEQ ID NO 21
```

```
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Trp Ile Arg Gln Pro Pro Gly Lys Gly Leu Glu Trp Ile Gly
1               5                   10

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Trp Ser Arg Gln Pro Pro Gly Lys Gly Leu Glu Trp Ile Gly
1               5                   10

<210> SEQ ID NO 23
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ile Ile Asp Pro Ser Asp Gly Ser Thr Ser Tyr Ala Gln Lys Phe Gln
1               5                   10                  15

Gly

<210> SEQ ID NO 24
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Ile Ile Asn Pro Leu Gly Gly Ser Thr Leu Tyr Ala Gln Lys Phe Gln
1               5                   10                  15

Gly

<210> SEQ ID NO 25
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ile Ile Asn Pro Gln Gly Gly Asp Thr Ser Tyr Ala Gln Lys Phe Gln
1               5                   10                  15

Gly
```

```
<210> SEQ ID NO 26
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Arg Ile Lys Arg Asp Gly Ser Glu Lys Tyr Tyr Val Asp Ser Val Lys
1               5                   10                  15

Gly

<210> SEQ ID NO 27
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Ile Ile Ser Gly Ser Gly Gly Ser Thr Tyr Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Ile Ile Ser Gly Ser Gly Gly Ala Thr Tyr Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ala Ile Ser Gly Ser Gly Gly Ala Thr Tyr Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30
```

Ala Ile Ser Gly Ser Gly Gly Ala Thr Tyr Tyr Ala Asp Ser Val Glu
1               5                   10                  15

Gly

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Glu Ile Ser His Ser Gly Ser Thr Asn Tyr Asn Pro Ser Leu Lys Ser
1               5                   10                  15

<210> SEQ ID NO 32
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Asp Ile Trp His Ser Gly Met Thr Asn Tyr Asn Pro Ser Leu Lys Ser
1               5                   10                  15

<210> SEQ ID NO 33
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Arg Val Thr Met Thr Arg Asp Thr Pro Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 34
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Arg Val Thr Met Thr Arg Asp Ala Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 35
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys
            20                  25                  30

<210> SEQ ID NO 36
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 37
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 38
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Arg Phe Thr Ile Ser Arg Asp Asn Ser Lys Asn Thr Leu Tyr Leu Gln
1               5                   10                  15

Met Ser Ser Leu Arg Ala Glu Asp Thr Ala Val Tyr Tyr Cys
            20                  25                  30

<210> SEQ ID NO 39
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 40
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Arg Val Thr Ile Ser Val Asp Thr Ser Lys Asn Gln Phe Ser Leu Lys
1               5                   10                  15

Leu Ser Pro Val Thr Ala Ala Asp Thr Ala Val Tyr Tyr Cys
            20                  25                  30

<210> SEQ ID NO 41
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Ala Arg Gly Ala Arg Arg Ile Thr Gly Tyr Gly Met Asp Val
1               5                   10

<210> SEQ ID NO 42
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ala Arg Asp Leu Gly Tyr Tyr Gly Ser Gly Met His Ala
1               5                   10

<210> SEQ ID NO 43
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Ala Arg Asp Leu Gly Tyr Tyr Gly Ser Gly Met His Val
1               5                   10

<210> SEQ ID NO 44
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

```
Ala Arg Asp Arg Gly Met Tyr Tyr Ala Ser Gly Phe Gly Pro
1               5                   10
```

```
<210> SEQ ID NO 45
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45
```

```
Ala Arg Asp Arg Gly Met Tyr Tyr Ala Ser Gly Phe Asn Pro
1               5                   10
```

```
<210> SEQ ID NO 46
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 46
```

```
Ala Arg Asp Gln Gly Tyr Lys Thr Pro Thr Asp Phe Asp Leu
1               5                   10
```

```
<210> SEQ ID NO 47
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47
```

```
Ala Lys Asp Pro Gly Tyr Asp Ser Ser Arg Tyr Tyr Tyr Ser Asn Tyr
1               5                   10                  15

Gly Met Asp Val
            20
```

```
<210> SEQ ID NO 48
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48
```

```
Ala Arg Ala Arg Pro Tyr Arg Glu Pro Tyr Gly Met Asp Val
1               5                   10
```

```
<210> SEQ ID NO 49
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49
```

```
Ala Arg Gly Pro Gly Tyr Asp Ser Ser Gly Tyr Ser Arg Arg Phe Asp
```

-continued

```
                1               5                  10                  15
Pro

<210> SEQ ID NO 50
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Trp Gly Gln Gly Thr Thr Val Thr Val Ser Ser
1               5                   10

<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Trp Gly Gln Gly Thr Thr Val Ile Val Ser Ser
1               5                   10

<210> SEQ ID NO 52
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Trp Gly Gln Gly Thr Leu Val Thr Val Ser Ser
1               5                   10

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Trp Gly Arg Gly Thr Leu Val Thr Val Ser Ser
1               5                   10

<210> SEQ ID NO 54
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

Asp Ile Gln Met Thr Gln Ser Pro Ser Ser Val Ser Ala Ser Val Gly
1               5                   10                  15
```

Asp Arg Val Thr Ile Thr Cys
            20

<210> SEQ ID NO 55
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 55

Glu Ile Val Met Thr Gln Ser Pro Gly Thr Leu Ser Leu Ser Pro Gly
1               5                   10                  15

Glu Arg Ala Thr Leu Ser Cys
            20

<210> SEQ ID NO 56
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 57
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Asp Ile Gln Leu Thr Gln Ser Pro Ser Ser Val Ser Ala Ser Val Gly
1               5                   10                  15

Asp Arg Val Thr Ile Thr Cys
            20

<210> SEQ ID NO 58
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 59
<211> LENGTH: 11
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 59

Arg Ala Ser Gln Gly Ile Ser Ser Trp Leu Ala
1               5                   10

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 60

Arg Ala Ser Gln Gly Ile Ser Arg Trp Leu Ala
1               5                   10

<210> SEQ ID NO 61
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Arg Ala Ser Gln Ser Val Ser Ser Ser Tyr Leu Ala
1               5                   10

<210> SEQ ID NO 62
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Gln Ala Ser Gln Asp Ile Thr Asn Tyr Leu Asn
1               5                   10

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Arg Ala Ser Gln Ser Ile Ser Ser Tyr Leu Asn
1               5                   10

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 64

Arg Ala Ser Gln Asp Ile Ser Ser Trp Leu Ala
1               5                   10

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 65

Arg Ala Ser Gln Ser Ile Ser Ser Trp Leu Ala
1               5                   10

<210> SEQ ID NO 66
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 66

Trp Tyr Gln Gln Lys Pro Gly Lys Ala Pro Lys Leu Leu Ile Tyr
1               5                   10                  15

<210> SEQ ID NO 67
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 67

Ala Ala Ser Asn Leu Gln Ser
1               5

<210> SEQ ID NO 68
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Ala Ser Ser Leu Gln Ser
1               5

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Gly Ala Ser Asn Arg Ala Thr
1               5

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Asp Ala Ser Asn Leu Glu Thr
1               5

<210> SEQ ID NO 71
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Gly Ala Ser Ser Leu Gln Ser
1               5

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Lys Ala Ser Ser Leu Glu Ser
1               5

<210> SEQ ID NO 73
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 74
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Gly Ile Pro Asp Arg Phe Ser Gly Ser Gly Ser Gly Thr Asp Phe Thr

```
1               5                   10                  15
Leu Thr Ile Ser Arg Leu Glu Pro Glu Asp Phe Ala Val Tyr Tyr Cys
                20                  25                  30
```

<210> SEQ ID NO 75
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

```
Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
                20                  25                  30
```

<210> SEQ ID NO 76
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

```
Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
                20                  25                  30
```

<210> SEQ ID NO 77
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 77

```
Gln Gln Ala Ser Val Phe Pro Phe Thr
1               5
```

<210> SEQ ID NO 78
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 78

```
Gln Gln Ala Asn Leu Leu Pro Phe Thr
1               5
```

<210> SEQ ID NO 79
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:

-continued

Synthetic peptide"

<400> SEQUENCE: 79

Gln Gln Leu Ser Ser Phe Pro Ile Thr
1               5

<210> SEQ ID NO 80
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gln Gln Ser Asp Val Leu Pro Ile Thr
1               5

<210> SEQ ID NO 81
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 81

Gln Gln Thr Tyr Ser Leu Tyr Thr
1               5

<210> SEQ ID NO 82
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Gln Gln Glu Leu Ala Phe Pro Arg Thr
1               5

<210> SEQ ID NO 83
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gln Gln Leu Asn Ser Tyr Pro Pro Thr
1               5

<210> SEQ ID NO 84
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

```
Phe Gly Gly Gly Thr Lys Val Glu Ile Lys
1               5                   10
```

<210> SEQ ID NO 85
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

```
Gln Val Gln Leu Val Gln Ser Gly Ala Gly Val Lys Lys Pro Gly Ala
1               5                   10                  15

Ser Val Lys Val Ser Cys Lys Ala Ser Gly Tyr Thr Phe Arg Ser Tyr
                20                  25                  30

Tyr Met Leu Trp Val Arg Gln Ala Pro Gly Gln Gly Leu Glu Trp Met
            35                  40                  45

Gly Ile Ile Asp Pro Ser Asp Gly Ser Thr Ser Tyr Ala Gln Lys Phe
        50                  55                  60

Gln Gly Arg Val Thr Met Thr Arg Asp Thr Pro Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Arg Ile Thr Gly Tyr Gly Met Asp Val Trp Gly
            100                 105                 110

Gln Gly Thr Thr Val Thr Val Ser Ser
        115                 120
```

<210> SEQ ID NO 86
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Arg Ser Tyr
                20                  25                  30

Tyr Met Leu Trp Val Arg Gln Ala Pro Gly Gln Gly Leu Glu Trp Met
            35                  40                  45

Gly Ile Ile Asp Pro Ser Asp Gly Ser Thr Ser Tyr Ala Gln Lys Phe
        50                  55                  60

Gln Gly Arg Val Thr Met Thr Arg Asp Ala Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Arg Ile Thr Gly Tyr Gly Met Asp Val Trp Gly
            100                 105                 110

Gln Gly Thr Thr Val Ile Val Ser Ser
        115                 120
```

<210> SEQ ID NO 87
<211> LENGTH: 120
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 87

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Met His Trp Val Arg Gln Ala Pro Gly Gln Gly Leu Glu Trp Met
        35                  40                  45

Gly Ile Ile Asn Pro Leu Gly Gly Ser Thr Leu Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Tyr Tyr Gly Ser Gly Met His Ala Trp Gly Gln
            100                 105                 110

Gly Thr Leu Val Thr Val Ser Ser
        115                 120

<210> SEQ ID NO 88
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Met His Trp Val Arg Gln Ala Pro Gly Gln Gly Leu Glu Trp Met
        35                  40                  45

Gly Ile Ile Asn Pro Leu Gly Gly Ser Thr Leu Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Tyr Tyr Gly Ser Gly Met His Val Trp Gly Gln
            100                 105                 110

Gly Thr Leu Val Thr Val Ser Ser
        115                 120

<210> SEQ ID NO 89
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 89

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Gln Gly Gly Asp Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Met Tyr Tyr Ala Ser Gly Phe Gly Pro Trp Gly
                100                 105                 110

Gln Gly Thr Leu Val Thr Val Ser Ser
            115                 120
```

<210> SEQ ID NO 90
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

```
Gln Val Gln Leu Val Gln Ser Gly Ala Lys Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Val Pro Gly Gln Gly Leu Glu Trp Met
            35                  40                  45

Gly Ile Ile Asn Pro Gln Gly Gly Asp Thr Ser Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Met Tyr Tyr Ala Ser Gly Phe Asn Pro Trp Gly
                100                 105                 110

Gln Gly Thr Leu Val Thr Val Ser Ser
            115                 120
```

<210> SEQ ID NO 91
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

```
Trp Met Glu Trp Val Arg Gln Ala Pro Gly Lys Gly Leu Glu Trp Val
            35                  40                  45

Ala Arg Ile Lys Arg Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gln Gly Tyr Lys Thr Pro Thr Asp Phe Asp Leu Trp Gly
                100                 105                 110

Arg Gly Thr Leu Val Thr Val Ser Ser
            115                 120
```

<210> SEQ ID NO 92
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Ser Tyr
                 20                  25                  30

Ala Met Val Trp Val Arg Gln Ala Pro Gly Lys Gly Leu Glu Trp Val
            35                  40                  45

Ser Ile Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Pro Gly Tyr Asp Ser Ser Arg Tyr Tyr Tyr Ser Asn Tyr
                100                 105                 110

Gly Met Asp Val Trp Gly Gln Gly Thr Thr Val Thr Val Ser Ser
            115                 120                 125
```

<210> SEQ ID NO 93
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 93

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Ser Tyr
                 20                  25                  30

Ala Met Val Trp Val Arg Gln Ala Pro Gly Lys Gly Leu Glu Trp Val
            35                  40                  45

Ser Ile Ile Ser Gly Ser Gly Gly Ala Thr Tyr Tyr Ala Asp Ser Val
 50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95

Ala Lys Asp Pro Gly Tyr Asp Ser Ser Arg Tyr Tyr Tyr Ser Asn Tyr
                100                 105                 110

Gly Met Asp Val Trp Gly Gln Gly Thr Thr Val Thr Val Ser Ser
            115                 120                 125

<210> SEQ ID NO 94
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
            100                 105                 110

Gly Met Asp Val Trp Gly Gln Gly Thr Thr Val Thr Val Ser Ser
        115                 120                 125

<210> SEQ ID NO 95
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
            100                 105                 110
```

-continued

Gly Met Asp Val Trp Gly Gln Gly Thr Thr Val Thr Val Ser Ser
            115                 120                 125

<210> SEQ ID NO 96
<211> LENGTH: 127
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
            100                 105                 110

Gly Met Asp Val Trp Gly Gln Gly Thr Thr Val Thr Val Ser Ser
        115                 120                 125

<210> SEQ ID NO 97
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Gly Tyr
            20                  25                  30

Tyr Trp Glu Trp Ile Arg Gln Pro Pro Gly Lys Gly Leu Glu Trp Ile
        35                  40                  45

Gly Glu Ile Ser His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Pro Tyr Arg Glu Pro Tyr Gly Met Asp Val Trp Gly Gln
            100                 105                 110

Gly Thr Thr Val Thr Val Ser Ser
        115                 120

<210> SEQ ID NO 98
<211> LENGTH: 120

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 98

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Gly Tyr
            20                  25                  30

Tyr Trp Glu Trp Ser Arg Gln Pro Pro Gly Lys Gly Leu Glu Trp Ile
        35                  40                  45

Gly Glu Ile Ser His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Pro Val Thr Ala Ala Asp Thr Ala Val Tyr Tyr Cys Ala
                85                  90                  95

Arg Ala Arg Pro Tyr Arg Glu Pro Tyr Gly Met Asp Val Trp Gly Gln
            100                 105                 110

Gly Thr Thr Val Thr Val Ser Ser
        115                 120

<210> SEQ ID NO 99
<211> LENGTH: 123
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 99

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Val Lys Tyr
            20                  25                  30

Tyr Trp Ser Trp Ile Arg Gln Pro Pro Gly Lys Gly Leu Glu Trp Ile
        35                  40                  45

Gly Asp Ile Trp His Ser Gly Met Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Gly Tyr Asp Ser Ser Gly Tyr Ser Arg Arg Phe Asp Pro
            100                 105                 110

Trp Gly Gln Gly Thr Leu Val Thr Val Ser Ser
        115                 120

<210> SEQ ID NO 100
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Val Phe Pro Phe
                85                  90                  95

Thr Phe Gly Gly Gly Thr Lys Val Glu Ile Lys
            100                 105

<210> SEQ ID NO 101
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Leu Leu Pro Phe
                85                  90                  95

Thr Phe Gly Gly Gly Thr Lys Val Glu Ile Lys
            100                 105

<210> SEQ ID NO 102
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Ser Ser Phe Pro
                85                  90                  95

Ile Thr Phe Gly Gly Gly Thr Lys Val Glu Ile Lys
            100                 105

<210> SEQ ID NO 103
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Val Leu Pro Ile
                85                  90                  95

Thr Phe Gly Gly Gly Thr Lys Val Glu Ile Lys
            100                 105

<210> SEQ ID NO 104
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Leu Tyr Thr
                85                  90                  95

Phe Gly Gly Gly Thr Lys Val Glu Ile Lys
        100                 105

<210> SEQ ID NO 105
<211> LENGTH: 107

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Leu Ala Phe Pro Arg
                85                  90                  95

Thr Phe Gly Gly Gly Thr Lys Val Glu Ile Lys
            100                 105

<210> SEQ ID NO 106
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys
            100                 105

<210> SEQ ID NO 107
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Gln Val Gln Leu Val Gln Ser Gly Ala Gly Val Lys Lys Pro Gly Ala
1               5                   10                  15

Ser Val Lys Val Ser Cys Lys Ala Ser Gly Tyr Thr Phe Arg Ser Tyr
```

```
            20                  25                  30
Tyr Met Leu Trp Val Arg Gln Ala Pro Gly Gln Gly Leu Glu Trp Met
         35                  40                  45
Gly Ile Ile Asp Pro Ser Asp Gly Ser Thr Ser Tyr Ala Gln Lys Phe
         50                  55                  60
Gln Gly Arg Val Thr Met Thr Arg Asp Thr Pro Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Gly Ala Arg Arg Ile Thr Gly Tyr Gly Met Asp Val Trp Gly
                100                 105                 110
Gln Gly Thr Thr Val Thr Val Ser Ser Ala Ser Thr Lys Gly Pro Ser
                115                 120                 125
Val Phe Pro Leu Ala Pro Cys Ser Arg Ser Thr Ser Glu Ser Thr Ala
                130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
                180                 185                 190
Pro Ser Ser Ser Leu Gly Thr Lys Thr Tyr Thr Cys Asn Val Asp His
                195                 200                 205
Lys Pro Ser Asn Thr Lys Val Asp Lys Arg Val Glu Ser Lys Tyr Gly
                210                 215                 220
Pro Pro Cys Pro Pro Cys Pro Ala Pro Glu Phe Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser Gln Glu Asp Pro
                260                 265                 270
Glu Val Gln Phe Asn Trp Tyr Val Asp Gly Val Glu Val His Asn Ala
                275                 280                 285
Lys Thr Lys Pro Arg Glu Glu Gln Phe Asn Ser Thr Tyr Arg Val Val
                290                 295                 300
Ser Val Leu Thr Val Leu His Gln Asp Trp Leu Asn Gly Lys Glu Tyr
305                 310                 315                 320
Lys Cys Lys Val Ser Asn Lys Gly Leu Pro Ser Ser Ile Glu Lys Thr
                325                 330                 335
Ile Ser Lys Ala Lys Gly Gln Pro Arg Glu Pro Gln Val Tyr Thr Leu
                340                 345                 350
Pro Pro Ser Gln Glu Glu Met Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Arg Leu Thr Val Asp Lys Ser
                405                 410                 415
Arg Trp Gln Glu Gly Asn Val Phe Ser Cys Ser Val Met His Glu Ala
                420                 425                 430
Leu His Asn His Tyr Thr Gln Lys Ser Leu Ser Leu Ser Leu Gly Lys
                435                 440                 445
```

<210> SEQ ID NO 108
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 108

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Arg Ser Tyr
            20                  25                  30

Tyr Met Leu Trp Val Arg Gln Ala Pro Gly Gln Gly Leu Glu Trp Met
        35                  40                  45

Gly Ile Ile Asp Pro Ser Asp Gly Ser Thr Tyr Ala Gln Lys Phe
    50                  55                  60

Gln Gly Arg Val Thr Met Thr Arg Asp Ala Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Arg Arg Ile Thr Gly Tyr Gly Met Asp Val Trp Gly
            100                 105                 110

Gln Gly Thr Thr Val Ile Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

```
Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 109
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 109

Gln Ala Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Met His Trp Val Arg Gln Ala Pro Gly Gln Gly Leu Glu Trp Met
        35                  40                  45

Gly Ile Ile Asn Pro Leu Gly Gly Ser Thr Leu Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Tyr Tyr Gly Ser Gly Met His Ala Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
```

```
                    260                 265                 270
Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 110
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Arg Tyr
            20                  25                  30

Tyr Met His Trp Val Arg Gln Ala Pro Gly Gln Gly Leu Glu Trp Met
        35                  40                  45

Gly Ile Ile Asn Pro Leu Gly Gly Ser Thr Leu Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Gly Tyr Tyr Gly Ser Gly Met His Val Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

Leu Gln Ser Ser Gly Leu Tyr Ser Leu Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
        210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 111
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Gln Gly Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg Asp Arg Gly Met Tyr Tyr Ala Ser Gly Phe Gly Pro Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 112
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 112

Gln Val Gln Leu Val Gln Ser Gly Ala Lys Val Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Val Pro Gly Gln Gly Leu Glu Trp Met
        35                  40                  45

Gly Ile Ile Asn Pro Gln Gly Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Met Tyr Tyr Ala Ser Gly Phe Asn Pro Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415
```

```
Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
            435                 440                 445

<210> SEQ ID NO 113
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Glu Trp Val Arg Gln Ala Pro Gly Lys Gly Leu Glu Trp Val
        35                  40                  45

Ala Arg Ile Lys Arg Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Tyr Lys Thr Pro Thr Asp Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

-continued

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 114
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Ser Tyr
            20                  25                  30

Ala Met Val Trp Val Arg Gln Ala Pro Gly Lys Gly Leu Glu Trp Val
        35                  40                  45

Ser Ile Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Tyr Asp Ser Ser Arg Tyr Tyr Ser Asn Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
```

```
225                 230                 235                 240

Phe Leu Gly Gly Pro Ser Val Phe Leu Phe Pro Pro Lys Pro Lys Asp
                    245                 250                 255

Thr Leu Met Ile Ser Arg Thr Pro Glu Val Thr Cys Val Val Val Asp
                    260                 265                 270

Val Ser Gln Glu Asp Pro Glu Val Gln Phe Asn Trp Tyr Val Asp Gly
                    275                 280                 285

Val Glu Val His Asn Ala Lys Thr Lys Pro Arg Glu Glu Gln Phe Asn
                    290                 295                 300

Ser Thr Tyr Arg Val Val Ser Val Leu Thr Val Leu His Gln Asp Trp
    305                 310                 315                 320

Leu Asn Gly Lys Glu Tyr Lys Cys Lys Val Ser Asn Lys Gly Leu Pro
                    325                 330                 335

Ser Ser Ile Glu Lys Thr Ile Ser Lys Ala Lys Gly Gln Pro Arg Glu
                    340                 345                 350

Pro Gln Val Tyr Thr Leu Pro Pro Ser Gln Glu Glu Met Thr Lys Asn
                    355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
    385                 390                 395                 400

Thr Pro Pro Val Leu Asp Ser Asp Gly Ser Phe Phe Leu Tyr Ser Arg
                    405                 410                 415

Leu Thr Val Asp Lys Ser Arg Trp Gln Glu Gly Asn Val Phe Ser Cys
                    420                 425                 430

Ser Val Met His Glu Ala Leu His Asn His Tyr Thr Gln Lys Ser Leu
                    435                 440                 445

Ser Leu Ser Leu Gly Lys
        450

<210> SEQ ID NO 115
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Glu Val Gln Leu Leu Glu Ser Gly Gly Gly Leu Val Gln Pro Gly Gly
    1               5                   10                  15

Ser Leu Arg Leu Ser Cys Ala Ala Ser Gly Phe Thr Phe Lys Ser Tyr
                    20                  25                  30

Ala Met Val Trp Val Arg Gln Ala Pro Gly Lys Gly Leu Glu Trp Val
                35                  40                  45

Ser Ile Ile Ser Gly Ser Gly Gly Ala Thr Tyr Tyr Ala Asp Ser Val
        50                  55                  60

Lys Gly Arg Phe Thr Ile Ser Arg Asp Asn Ser Lys Asn Thr Leu Tyr
    65                  70                  75                  80

Leu Gln Met Asn Ser Leu Arg Ala Glu Asp Thr Ala Val Tyr Tyr Cys
                    85                  90                  95

Ala Lys Asp Pro Gly Tyr Asp Ser Ser Arg Tyr Tyr Tyr Ser Asn Tyr
                    100                 105                 110

Gly Met Asp Val Trp Gly Gln Gly Thr Thr Val Thr Val Ser Ser Ala
                115                 120                 125
```

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 116
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 116

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Ser Ser Val
            20                  25                  30
Ala Met Val Trp Val Arg Gln Ala Pro Gly Lys Gly Leu Glu Trp Val
        35                  40                  45
Ser Ala Ile Ser Gly Ser Gly Gly Ala Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Asp Pro Gly Tyr Asp Ser Ser Arg Tyr Tyr Tyr Ser Asn Tyr
            100                 105                 110
Gly Met Asp Val Trp Gly Gln Gly Thr Thr Val Thr Val Ser Ser Ala
        115                 120                 125
Ser Thr Lys Gly Pro Ser Val Phe Pro Leu Ala Pro Cys Ser Arg Ser
130                 135                 140
Thr Ser Glu Ser Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Lys Thr Tyr
        195                 200                 205
Thr Cys Asn Val Asp His Lys Pro Ser Asn Thr Lys Val Asp Lys Arg
210                 215                 220
Val Glu Ser Lys Tyr Gly Pro Pro Cys Pro Pro Cys Pro Ala Pro Glu
225                 230                 235                 240
Phe Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
            260                 265                 270
Val Ser Gln Glu Asp Pro Glu Val Gln Phe Asn Trp Tyr Val Asp Gly
        275                 280                 285
Val Glu Val His Asn Ala Lys Thr Lys Pro Arg Glu Glu Gln Phe Asn
290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Gly Leu Pro
                325                 330                 335
Ser Ser Ile Glu Lys Thr Ile Ser Lys Ala Lys Gly Gln Pro Arg Glu
            340                 345                 350
Pro Gln Val Tyr Thr Leu Pro Pro Ser Gln Glu Glu Met Thr Lys Asn
        355                 360                 365
Gln Val Ser Leu Thr Cys Leu Val Lys Gly Phe Tyr Pro Ser Asp Ile
370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Arg
                405                 410                 415
Leu Thr Val Asp Lys Ser Arg Trp Gln Glu Gly Asn Val Phe Ser Cys
            420                 425                 430
Ser Val Met His Glu Ala Leu His Asn His Tyr Thr Gln Lys Ser Leu
```

Ser Leu Ser Leu Gly Lys
        450

<210> SEQ ID NO 117
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

```
Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
    450

<210> SEQ ID NO 118
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Val
            20                  25                  30

Ala Met Val Trp Val Arg Gln Ala Pro Gly Lys Gly Leu Glu Trp Val
        35                  40                  45

Ser Ala Ile Ser Gly Ser Gly Gly Ala Thr Tyr Tyr Ala Asp Ser Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Tyr Asp Ser Ser Arg Tyr Tyr Tyr Ser Asn Tyr
                100                 105                 110

Gly Met Asp Val Trp Gly Gln Gly Thr Thr Val Thr Val Ser Ser Ala
            115                 120                 125

Ser Thr Lys Gly Pro Ser Val Phe Pro Leu Ala Pro Cys Ser Arg Ser
        130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
    210                 215                 220
```

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
        275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
            340                 345                 350

Pro Gln Val Tyr Thr Leu Pro Pro Ser Gln Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
            405                 410                 415

Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
        435                 440                 445

Ser Leu Ser Leu Gly Lys
    450

<210> SEQ ID NO 119
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Gly Tyr
            20                  25                  30

Tyr Trp Glu Trp Ile Arg Gln Pro Pro Gly Lys Gly Leu Glu Trp Ile
        35                  40                  45

Gly Glu Ile Ser His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95

Arg Ala Arg Pro Tyr Arg Glu Pro Tyr Gly Met Asp Val Trp Gly Gln
        100                 105                 110

Gly Thr Thr Val Thr Val Ser Ser Ala Ser Thr Lys Gly Pro Ser Val

|   |   |   |   |   | 115 |   |   |   |   | 120 |   |   |   |   | 125 |   |   |
|---|---|---|---|---|---|---|---|---|---|---|---|---|---|---|---|---|---|

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 120
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Arg Gly Tyr
            20                  25                  30

Tyr Trp Glu Trp Ser Arg Gln Pro Pro Gly Lys Gly Leu Glu Trp Ile
    35                  40                  45

Gly Glu Ile Ser His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Pro Val Thr Ala Ala Asp Thr Ala Val Tyr Tyr Cys Ala
                85                  90                  95

Arg Ala Arg Pro Tyr Arg Glu Pro Tyr Gly Met Asp Val Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

```
<210> SEQ ID NO 121
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Val Lys Tyr
            20                  25                  30

Tyr Trp Ser Trp Ile Arg Gln Pro Pro Gly Lys Gly Leu Glu Trp Ile
        35                  40                  45

Gly Asp Ile Trp His Ser Gly Met Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Gly Tyr Asp Ser Ser Gly Tyr Ser Arg Arg Phe Asp Pro
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
```

```
                355                 360                 365
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
                435                 440                 445

Gly Lys
    450

<210> SEQ ID NO 122
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Val Phe Pro Phe
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 123
<211> LENGTH: 214
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 123
```

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Leu Leu Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 124
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 124
```

Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Ser Phe Pro
                85                  90                  95

Ile Thr Phe Gly Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
        210                 215

<210> SEQ ID NO 125
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Ser Asp Val Leu Pro Ile
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 126
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Leu Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 127
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 127

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Glu Leu Ala Phe Pro Arg
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210
```

<210> SEQ ID NO 128
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 128

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Leu Asn Ser Tyr Pro Pro
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205
```

Phe Asn Arg Gly Glu Cys
     210

<210> SEQ ID NO 129
<211> LENGTH: 2772
<212> TYPE: DNA
<213> ORGANISM: Homo sapiens

<400> SEQUENCE: 129

| | | | | | |
|---|---|---|---|---|---|
| atggagaggg | ggctgccgct | cctctgcgcc | gtgctcgccc | tcgtcctcgc | cccggccggc | 60 |
| gcttttcgca | acgataaatg | tggcgatact | ataaaaattg | aaagccccgg | gtaccttaca | 120 |
| tctcctggtt | atcctcattc | ttatcaccca | agtgaaaaat | gcgaatggct | gattcaggct | 180 |
| ccggacccat | accagagaat | tatgatcaac | ttcaaccctc | acttcgattt | ggaggacaga | 240 |
| gactgcaagt | atgactacgt | ggaagtcttc | gatggagaaa | atgaaaatgg | acattttagg | 300 |
| ggaaagttct | gtggaaagat | agcccctcct | cctgttgtgt | cttcagggcc | atttcttttt | 360 |
| atcaaatttg | tctctgacta | cgaaacacat | ggtgcaggat | tttccatacg | ttatgaaatt | 420 |
| ttcaagagag | gtcctgaatg | ttcccagaac | tacacaacac | ctagtggagt | gataaagtcc | 480 |
| cccggattcc | ctgaaaaata | tcccaacagc | cttgaatgca | cttatattgt | ctttgcgcca | 540 |
| aagatgtcag | agattatcct | ggaatttgaa | agctttgacc | tggagcctga | ctcaaatcct | 600 |
| ccaggggga | tgttctgtcg | ctacgaccgg | ctagaaatct | gggatggatt | ccctgatgtt | 660 |
| ggccctcaca | ttgggcgtta | ctgtggacag | aaaacaccag | gtcgaatccg | atcctcatcg | 720 |
| ggcattctct | ccatggtttt | ttacaccgac | agcgcgatag | caaaagaagg | tttctcagca | 780 |
| aactacagtg | tcttgcagag | cagtgtctca | gaagatttca | atgtatgga | agctctgggc | 840 |
| atggaatcag | gagaaattca | ttctgaccag | atcacagctt | cttcccagta | tagcaccaac | 900 |
| tggtctgcag | agcgctcccg | cctgaactac | cctgagaatg | ggtggactcc | cggagaggat | 960 |
| tcctaccgag | agtggataca | ggtagacttg | ggccttctgc | gctttgtcac | ggctgtcggg | 1020 |
| acacagggcg | ccatttcaaa | agaaaccaag | aagaaatatt | atgtcaagac | ttacaagatc | 1080 |
| gacgttagct | ccaacgggga | agactggatc | accataaaag | aaggaaacaa | acctgttctc | 1140 |
| tttcagggaa | acaccaaccc | cacagatgtt | gtggttgcag | tattccccaa | accactgata | 1200 |
| actcgatttg | tccgaatcaa | gcctgcaact | tgggaaactg | gcatatctat | gagatttgaa | 1260 |
| gtatacggtt | gcaagataac | agattatcct | tgctctggaa | tgttgggtat | ggtgtctgga | 1320 |
| cttatttctg | actcccagat | cacatcatcc | aaccaagggg | acagaaactg | gatgcctgaa | 1380 |
| aacatccgcc | tggtaaccag | tcgctctggc | tgggcacttc | cacccgcacc | tcattcctac | 1440 |
| atcaatgagt | ggctccaaat | agacctgggg | gaggagaaga | tcgtgagggg | catcatcatt | 1500 |
| cagggtggga | agcaccgaga | gaacaaggtg | ttcatgagga | agttcaagat | cgggtacagc | 1560 |
| aacaacggct | cggactggaa | gatgatcatg | gatgacagca | aacgcaaggc | gaagtctttt | 1620 |
| gagggcaaca | caactatga | tacacctgag | ctgcggactt | ttccagctct | ctccacgcga | 1680 |
| ttcatcagga | tctaccccga | gagagccact | catggcggac | tggggctcag | aatggagctg | 1740 |
| ctgggctgtg | aagtggaagc | ccctacagct | ggaccgacca | ctcccaacgg | gaacttggtg | 1800 |
| gatgaatgtg | atgacgacca | ggccaactgc | cacagtggaa | caggtgatga | cttccagctc | 1860 |
| acaggtggca | ccactgtgct | ggccacagaa | aagcccacgg | tcatagacag | caccatacaa | 1920 |
| tcagagtttc | caacatatgg | ttttaactgt | gaatttggct | ggggctctca | caagaccttc | 1980 |
| tgccactggg | aacatgacaa | tcacgtgcag | ctcaagtgga | gtgtgttgac | cagcaagacg | 2040 |

```
ggacccattc aggatcacac aggagatggc aacttcatct attcccaagc tgacgaaaat   2100
cagaagggca aagtggctcg cctggtgagc cctgtggttt attcccagaa ctctgcccac   2160
tgcatgacct tctggtatca catgtctggg tcccacgtcg gcacactcag ggtcaaactg   2220
cgctaccaga agccagagga gtacgatcag ctggtctgga tggccattgg acaccaaggt   2280
gaccactgga aggaagggcg tgtcttgctc cacaagtctc tgaaacttta tcaggtgatt   2340
ttcgagggcg aaatcggaaa aggaaacctt ggtgggattg ctgtggatga cattagtatt   2400
aataaccaca tttcacaaga agattgtgca aaaccagcag acctggataa aagaacccca   2460
gaaattaaaa ttgatgaaac agggagcacg ccaggatacg aaggtgaagg agaaggtgac   2520
aagaacatct ccaggaagcc aggcaatgtg ttgaagacct tagaccccat cctcatcacc   2580
atcatagcca tgagtgccct gggggtcctc ctgggggctg tctgtggggt cgtgctgtac   2640
tgtgcctgtt ggcataatgg gatgtcagaa agaaacttgt ctgccctgga gaactataac   2700
tttgaacttg tggatggtgt gaagttgaaa aagacaaac tgaatacaca gagtacttat   2760
tcggaggcat ga                                                       2772
```

<210> SEQ ID NO 130
<211> LENGTH: 923
<212> TYPE: PRT
<213> ORGANISM: Homo sapiens

<400> SEQUENCE: 130

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly His Phe Arg Gly Lys Phe Cys Gly Lys Ile Ala Pro Pro Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240
```

```
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Ser Thr Asn Trp Ser Ala Glu
    290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Lys Ile Asp Val Ser Ser Asn Gly Glu Asp
        355                 360                 365
Trp Ile Thr Ile Lys Glu Gly Asn Lys Pro Val Leu Phe Gln Gly Asn
    370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Ser Ser Asn Gln Gly Asp Arg Asn Trp Met Pro Glu Asn Ile Arg Leu
    450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
            500                 505                 510
Arg Lys Phe Lys Ile Gly Tyr Ser Asn Asn Gly Ser Asp Trp Lys Met
        515                 520                 525
Ile Met Asp Asp Ser Lys Arg Lys Ala Lys Ser Phe Glu Gly Asn Asn
    530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Leu Val Asp Glu Cys Asp Asp Gln Ala
        595                 600                 605
Asn Cys His Ser Gly Thr Gly Asp Asp Phe Gln Leu Thr Gly Gly Thr
    610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
```

```
             660                 665                 670
Trp Ser Val Leu Thr Ser Lys Thr Gly Pro Ile Gln Asp His Thr Gly
            675                 680                 685
Asp Gly Asn Phe Ile Tyr Ser Gln Ala Asp Glu Asn Gln Lys Gly Lys
            690                 695                 700
Val Ala Arg Leu Val Ser Pro Val Val Tyr Ser Gln Asn Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
            740                 745                 750
Trp Met Ala Ile Gly His Gln Gly Asp His Trp Lys Glu Gly Arg Val
            755                 760                 765
Leu Leu His Lys Ser Leu Lys Leu Tyr Gln Val Ile Phe Glu Gly Glu
            770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
                805                 810                 815
Lys Lys Asn Pro Glu Ile Lys Ile Asp Glu Thr Gly Ser Thr Pro Gly
            820                 825                 830
Tyr Glu Gly Glu Gly Gly Asp Lys Asn Ile Ser Arg Lys Pro Gly
            835                 840                 845
Asn Val Leu Lys Thr Leu Asp Pro Ile Leu Ile Thr Ile Ala Met
850                 855                 860
Ser Ala Leu Gly Val Leu Leu Gly Ala Val Cys Gly Val Val Leu Tyr
865                 870                 875                 880
Cys Ala Cys Trp His Asn Gly Met Ser Glu Arg Asn Leu Ser Ala Leu
                885                 890                 895
Glu Asn Tyr Asn Phe Glu Leu Val Asp Gly Val Lys Leu Lys Lys Asp
                900                 905                 910
Lys Leu Asn Thr Gln Ser Thr Tyr Ser Glu Ala
            915                 920

<210> SEQ ID NO 131
<211> LENGTH: 2772
<212> TYPE: DNA
<213> ORGANISM: Macaca fascicularis

<400> SEQUENCE: 131
atggagaagg ggttgccgct cctctgcgcc gcgctcgccc tcgccctcgc cccggccggc       60
gcttttcgca acgataaatg tggcgatact ataaaaattg aaagccccgg gtaccttaca      120
tctcctggtt atcctcattc ttatcaccca agtgaaaaat gtgaatggct gattcaggct      180
ccggacccat accagagaat tatgatcaac ttcaaccctc acttcgattt ggaggacaga      240
gattgcaagt atgactacgt ggaagtcttc gatggagaaa atgaaaatgg acgtttatgg      300
ggaaagttct gtggaaagat agcccctcct cctgttgtgt cttcagggca atttctttt       360 atcaaatttg tctctgacta cgaaacacac ggtgcaggat tttccatacg ttatgaaatt      420
ttcaagagag gtcctgaatg ttcccagaac tacacaacac ctagtggagt gataaagtcc      480
cccggattcc ctgaaaaata cccaacagcc ttgatgcact tatattgtc ctttgcacca       540 aagatgtcag agattatcct ggaatttgaa agctttgacc tggagcctga ctcaaatcct      600
ccagggggga tgttctgtcg ctacgaccgg ctggaaatct gggatggatt ccctgacgtt      660
```

```
ggccctcaca ttgggcgtta ctgtggacag aaaacaccag gtcgaatccg atcctcatcg      720
ggcattctct ccatggtttt ttacaccgac agcgcaatag caaaagaagg tttctcagca      780
aactacagtg tcttgcagag cagtgtctca gaagatttca aatgtatgga agctgtgggc      840
atggaatcag gagaaattca ttctgaccag atcacagctt cttcccagta cagcaccaac      900
tggtctgcag agcgctcccg cctgaactat cctgagaatg ggtggactcc cggagaagat      960
tcctaccgag agtggataca ggtggacttg ggccttctac gcttcgttac ggctgtcggg     1020
acacagggcg ccatttcaaa agaaaccaag aagaaatatt atgtcaagac ttacaaaatt     1080
gacattagct ccaacgggga agactggatc accataaaag aaggaaacaa acctgttctc     1140
tttcagggaa acaccaaccc cacagacgtt gtggttgcag tattccccaa gccactgata     1200
actcgatttg tccgaatcaa gcctgcaact tgggaaactg gcatatctct gagatttgaa     1260
gtatatggtt gcaagataac agattatcct tgctccggaa tgttgggtat ggtgtctgga     1320
cttatttctg actcccagat cacatcatcc aaccaagggg acagaaactg gatgcctgaa     1380
aacatccgcc tggtaaccag tcgctccggc tgggcactgc caccgcacc tcattcctac      1440 gtcaatgagt ggctccaaat agacctgggg gaggagaaga tcgtgagggg catcatcatt     1500
cagggtggga agcaccgaga gaacaaggta ttcatgagga agttcaagat cgggtacagc     1560
aacaacggct ccgactggaa gatgatcatg gacgacagca acgcaaggc aaagtctttt      1620 gagggcaaca acaactatga cacacctgag ctgcggactt ttccagctct ctccacgcga     1680
ttcatcagga tctaccccga gagagccact catggcggac tggggctccg aatggagctg     1740
ctgggctgtg aagtggaagc ccctacagct ggaccgacca ctcccaacgg gaacccggtg     1800
gatgaatgtg atgacgacca ggccaactgc acagtggaa caggtgatga cttccagctc      1860
acaggtggca ccactgtgct ggccacagaa aagcccacgg tcatagacag caccatacaa     1920
tcagagtttc ctacatatgg tttttaactgt gaatttggct ggggctctca caagaccttc     1980
tgccactggg aacatgacaa tcacgtgcag ctcaagtgga gtgtgttgac cagcaagacg     2040
ggacccattc aggatcacac aggagatggc aacttcatct attcccaagc tgatgaaaat     2100
cagaagggca aagtggctcg cctggtgagc cctgtggttt attcccagaa ctctgcccac     2160
tgcatgacct tctggtatca catgtctggg tcccacgtcg gcacactcag ggtcaaactg     2220
cgctaccaga agccagagga gtacgatcag ctggtctgga tggccattgg acaccaaggt     2280
gaccactgga aggaagggcg tgtcttgctt cacaagtctc tgaaacttta tcaggtgatt     2340
ttcgagggca aaatcggaaa aggaaacctt ggtgggattg ctgtggatga cattagtatc     2400
aataaccaca tttcacaaga agattgtgca aaaccagcag acctggataa aaagaaccca     2460
gaaattaaaa ttgatgaaac agggagcaca ccaggatatg aaggtgaagg agaaggtgac     2520
aagaacatct ccaggaaacc aggcaatgtg ttgaagacct tagaccccat cctcatcacc     2580
atcatagcca tgagcgccct gggggtcctc ctggggctg tgtgcggggt cgtgctgtac      2640
tgtgcctgtt ggcataatgg gatgtcagaa agaaacttgt ctgccctgga gaactataac     2700
tttgaacttg tggacggtgt gaagttgaaa aaagacaaac tgaatacaca gagtacttat     2760
tcggaggcat ga                                                        2772
```

<210> SEQ ID NO 132
<211> LENGTH: 923
<212> TYPE: PRT
<213> ORGANISM: Macaca fascicularis

<400> SEQUENCE: 132

```
Met Glu Lys Gly Leu Pro Leu Leu Cys Ala Ala Leu Ala Leu Ala Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
                85                  90                  95

Gly Arg Leu Trp Gly Lys Phe Cys Gly Lys Ile Ala Pro Pro Pro Val
            100                 105                 110

Val Ser Ser Gly Gln Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Thr Pro Ser Gly Val Ile Lys Ser
145                 150                 155                 160

Pro Gly Phe Pro Glu Lys Tyr Pro Asn Ser Leu Glu Cys Thr Tyr Ile
                165                 170                 175

Val Phe Ala Pro Lys Met Ser Glu Ile Ile Leu Glu Phe Glu Ser Phe
            180                 185                 190

Asp Leu Glu Pro Asp Ser Asn Pro Pro Gly Gly Met Phe Cys Arg Tyr
        195                 200                 205

Asp Arg Leu Glu Ile Trp Asp Gly Phe Pro Asp Val Gly Pro His Ile
    210                 215                 220

Gly Arg Tyr Cys Gly Gln Lys Thr Pro Gly Arg Ile Arg Ser Ser Ser
225                 230                 235                 240

Gly Ile Leu Ser Met Val Phe Tyr Thr Asp Ser Ala Ile Ala Lys Glu
                245                 250                 255

Gly Phe Ser Ala Asn Tyr Ser Val Leu Gln Ser Ser Val Ser Glu Asp
            260                 265                 270

Phe Lys Cys Met Glu Ala Val Gly Met Glu Ser Gly Glu Ile His Ser
        275                 280                 285

Asp Gln Ile Thr Ala Ser Ser Gln Tyr Ser Thr Asn Trp Ser Ala Glu
    290                 295                 300

Arg Ser Arg Leu Asn Tyr Pro Glu Asn Gly Trp Thr Pro Gly Glu Asp
305                 310                 315                 320

Ser Tyr Arg Glu Trp Ile Gln Val Asp Leu Gly Leu Leu Arg Phe Val
                325                 330                 335

Thr Ala Val Gly Thr Gln Gly Ala Ile Ser Lys Glu Thr Lys Lys Lys
            340                 345                 350

Tyr Tyr Val Lys Thr Tyr Lys Ile Asp Ile Ser Ser Asn Gly Glu Asp
        355                 360                 365

Trp Ile Thr Ile Lys Glu Gly Asn Lys Pro Val Leu Phe Gln Gly Asn
    370                 375                 380

Thr Asn Pro Thr Asp Val Val Val Ala Val Phe Pro Lys Pro Leu Ile
385                 390                 395                 400

Thr Arg Phe Val Arg Ile Lys Pro Ala Thr Trp Glu Thr Gly Ile Ser
                405                 410                 415
```

Leu Arg Phe Glu Val Tyr Gly Cys Lys Ile Thr Asp Tyr Pro Cys Ser
            420                 425             430

Gly Met Leu Gly Met Val Ser Gly Leu Ile Ser Asp Ser Gln Ile Thr
            435                 440             445

Ser Ser Asn Gln Gly Asp Arg Asn Trp Met Pro Glu Asn Ile Arg Leu
450                 455                 460

Val Thr Ser Arg Ser Gly Trp Ala Leu Pro Ala Pro His Ser Tyr
465                 470                 475             480

Val Asn Glu Trp Leu Gln Ile Asp Leu Gly Glu Lys Ile Val Arg
            485                 490             495

Gly Ile Ile Ile Gln Gly Lys His Arg Glu Asn Lys Val Phe Met
            500                 505             510

Arg Lys Phe Lys Ile Gly Tyr Ser Asn Asn Gly Ser Asp Trp Lys Met
            515                 520             525

Ile Met Asp Asp Ser Lys Arg Lys Ala Lys Ser Phe Glu Gly Asn Asn
        530                 535             540

Asn Tyr Asp Thr Pro Glu Leu Arg Thr Phe Pro Ala Leu Ser Thr Arg
545                 550                 555                 560

Phe Ile Arg Ile Tyr Pro Glu Arg Ala Thr His Gly Gly Leu Gly Leu
                565                 570                 575

Arg Met Glu Leu Leu Gly Cys Glu Val Glu Ala Pro Thr Ala Gly Pro
            580                 585                 590

Thr Thr Pro Asn Gly Asn Pro Val Asp Glu Cys Asp Asp Gln Ala
            595                 600             605

Asn Cys His Ser Gly Thr Gly Asp Asp Phe Gln Leu Thr Gly Gly Thr
            610                 615             620

Thr Val Leu Ala Thr Glu Lys Pro Thr Val Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Asn His Val Gln Leu Lys
            660                 665             670

Trp Ser Val Leu Thr Ser Lys Thr Gly Pro Ile Gln Asp His Thr Gly
            675                 680             685

Asp Gly Asn Phe Ile Tyr Ser Gln Ala Asp Glu Asn Gln Lys Gly Lys
            690                 695             700

Val Ala Arg Leu Val Ser Pro Val Val Tyr Ser Gln Asn Ser Ala His
705                 710                 715                 720

Cys Met Thr Phe Trp Tyr His Met Ser Gly Ser His Val Gly Thr Leu
            725                 730             735

Arg Val Lys Leu Arg Tyr Gln Lys Pro Glu Glu Tyr Asp Gln Leu Val
            740                 745             750

Trp Met Ala Ile Gly His Gln Gly Asp His Trp Lys Glu Gly Arg Val
            755                 760             765

Leu Leu His Lys Ser Leu Lys Leu Tyr Gln Val Ile Phe Glu Gly Glu
            770                 775             780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Ala Asp Leu Asp
                805                 810                 815

Lys Lys Asn Pro Glu Ile Lys Ile Asp Glu Thr Gly Ser Thr Pro Gly
            820                 825             830

```
            Tyr Glu Gly Glu Gly Glu Asp Lys Asn Ile Ser Arg Lys Pro Gly
                835                 840                 845

Asn Val Leu Lys Thr Leu Asp Pro Ile Leu Ile Thr Ile Ile Ala Met
            850                 855                 860

Ser Ala Leu Gly Val Leu Leu Gly Ala Val Cys Gly Val Val Leu Tyr
            865                 870                 875                 880

Cys Ala Cys Trp His Asn Gly Met Ser Glu Arg Asn Leu Ser Ala Leu
                            885                 890                 895

Glu Asn Tyr Asn Phe Glu Leu Val Asp Gly Val Lys Leu Lys Lys Asp
                        900                 905                 910

Lys Leu Asn Thr Gln Ser Thr Tyr Ser Glu Ala
                        915                 920

<210> SEQ ID NO 133
<211> LENGTH: 2772
<212> TYPE: DNA
<213> ORGANISM: Mus musculus

<400> SEQUENCE: 133
atggagaggg ggctgccgtt gctgtgcgcc acgctcgccc ttgccctcgc cctggcgggc      60
gctttccgca gcgacaaatg tggcgggacc ataaaaatcg aaaacccagg gtacctcaca    120
tctcccggtt accctcattc ttaccatcca agtgagaagt gtgaatggct aatccaagct    180
ccggaaccct accagagaat catgatcaac ttcaacccac atttcgattt ggaggacaga    240
gactgcaagt atgactacgt ggaagtaatc gatggggaga tgaaggcgg ccgcctgtgg     300 gggaagttct gtgggaagat tgcaccttct cctgtggtgt cttcagggcc ctttctcttc    360
atcaaatttg tctctgacta tgagacacat ggggcagggt tttccatccg ctatgaaatc    420
ttcaagagag ggcccgaatg ttctcagaac tatacagcac ctactggagt gataaagtcc    480
cctgggttcc ctgaaaaata ccccaacagc ttggagtgca cctacatcat ctttgcacca    540
aagatgtctg agataatcct ggagtttgaa agttttgacc tggagcaaga ctcgaatcct    600
cccggaggaa tgttctgtcg ctatgaccgg ctggagatct gggatggatt ccctgaagtt    660
ggccctcaca ttgggcgtta ttgtgggcag aaaactcctg ccggatccg ctcctcttca     720 ggcgttctat ccatggtctt ttacactgac agcgcaatag caaaagaagg tttctcagcc    780
aactacagtg tgctacagag cagcatctct gaagatttta gtgtatgga ggctctgggc     840 atggaatctg gagagatcca ttctgatcag atcactgcat cttcacagta tggtaccaac    900
tggtctgtag agcgctcccg cctgaactac cctgaaaatg ggtggactcc aggagaagac    960
tcctacaagg agtggatcca ggtggacttg ggcctcctgc gattcgttac tgctgtaggg    1020
acacagggtg ccatttccaa ggaaaccaag aagaaatatt atgtcaagac ttacagagta    1080
gacatcagct ccaacggaga ggactggatc tccctgaaag agggaaataa agccattatc    1140
tttcagggaa acaccaaccc cacagatgtt gtcttaggag tttttctccaa accactgata   1200 actcgatttg tccgaatcaa acctgtatcc tgggaaactg gtatatctat gagatttgaa   1260
gtttatggct gcaagataac agattatcct tgctctggaa tgttgggcat ggtgtctgga   1320
cttatttcag actcccagat tacagcatcc aatcaagccg acaggaattg gatgccagaa   1380
aacatccgtc tggtgaccag tcgtaccggc tgggcactgc accctcacc ccacccatac    1440 accaatgaat ggctccaagt ggacctggga gatgagaaga tagtaagagg tgtcatcatt   1500
cagggtggga agcaccgaga aaacaaggtg ttcatgagga agttcaagat cgcctatagt   1560
aacaatggct ctgactggaa aactatcatg gatgacagca gcgcaaggc taagtcgttc    1620
```

```
gaaggcaaca acaactatga cacacctgag cttcggacgt tttcacctct ctccacaagg    1680
ttcatcagga tctaccctga gagagccaca cacagtgggc ttgggctgag gatggagcta    1740
ctgggctgtg aagtggaagc acctacagct ggaccaacca cacccaatgg gaacccagtg    1800
gatgagtgtg acgacgacca ggccaactgc cacagtggca caggtgatga cttccagctc    1860
acaggaggca ccactgtcct ggccacagag aagccaacca ttatagacag caccatccaa    1920
tcagagttcc cgacatacgg ttttaactgc gagtttggct ggggctctca caagacattc    1980
tgccactggg agcatgacag ccatgcacag ctcaggtgga gtgtgctgac cagcaagaca    2040
gggccgattc aggaccatac aggagatggc aacttcatct attcccaagc tgatgaaaat    2100
cagaaaggca aagtagcccg cctggtgagc cctgtggtct attcccagag ctctgcccac    2160
tgtatgacct tctggtatca catgtccggc tctcatgtgg gtacactgag ggtcaaacta    2220
cgctaccaga agccagagga atatgatcaa ctggtctgga tggtggttgg gcaccaagga    2280
gaccactgga agaaggacg tgtcttgctg cacaaatctc tgaaactata tcaggttatt    2340
tttgaaggtg aaatcggaaa aggaaacctt ggtggaattg ctgtggatga tatcagtatt    2400
aacaaccata tttctcagga agactgtgca aaaccaacag acctagataa aaagaacaca    2460
gaaattaaaa ttgatgaaac agggagcact ccaggatatg aaggagaagg ggaaggtgac    2520
aagaacatct ccaggaagcc aggcaatgtg cttaagaccc tggatcccat cctgatcacc    2580
atcatagcca tgagtgccct gggagtactc ctgggtgcag tctgtggagt tgtgctgtac    2640
tgtgcctgtt ggcacaatgg gatgtcagaa aggaacctat ctgccctgga aactataaac    2700
tttgaacttg tggatggtgt aaagttgaaa aaagataaac tgaacccaca gagtaattac    2760
tcagaggcgt ga                                                        2772
```

<210> SEQ ID NO 134
<211> LENGTH: 923
<212> TYPE: PRT
<213> ORGANISM: Mus musculus

<400> SEQUENCE: 134

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
            20                  25                  30

Ile Glu Asn Pro Gly Tyr Leu Thr Ser Pro Gly Tyr Pro His Ser Tyr
        35                  40                  45

His Pro Ser Glu Lys Cys Glu Trp Leu Ile Gln Ala Pro Glu Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Ile Asp Gly Glu Asn Glu Gly
                85                  90                  95

Gly Arg Leu Trp Gly Lys Phe Cys Gly Lys Ile Ala Pro Ser Pro Val
            100                 105                 110

Val Ser Ser Gly Pro Phe Leu Phe Ile Lys Phe Val Ser Asp Tyr Glu
        115                 120                 125

Thr His Gly Ala Gly Phe Ser Ile Arg Tyr Glu Ile Phe Lys Arg Gly
    130                 135                 140

Pro Glu Cys Ser Gln Asn Tyr Thr Ala Pro Thr Gly Val Ile Lys Ser
145                 150                 155                 160

```
Pro Gly Phe Pro Glu Lys Tyr Pro Asn Ser Leu Glu Cys Thr Tyr Ile
            165                 170                 175
Ile Phe Ala Pro Lys Met Ser Glu Ile Ile Leu Glu Phe Glu Ser Phe
        180                 185                 190
Asp Leu Glu Gln Asp Ser Asn Pro Pro Gly Met Phe Cys Arg Tyr
        195                 200                 205
Asp Arg Leu Glu Ile Trp Asp Gly Phe Pro Glu Val Gly Pro His Ile
        210                 215                 220
Gly Arg Tyr Cys Gly Gln Lys Thr Pro Gly Arg Ile Arg Ser Ser Ser
225                 230                 235                 240
Gly Val Leu Ser Met Val Phe Tyr Thr Asp Ser Ala Ile Ala Lys Glu
            245                 250                 255
Gly Phe Ser Ala Asn Tyr Ser Val Leu Gln Ser Ser Ile Ser Glu Asp
            260                 265                 270
Phe Lys Cys Met Glu Ala Leu Gly Met Glu Ser Gly Glu Ile His Ser
        275                 280                 285
Asp Gln Ile Thr Ala Ser Ser Gln Tyr Gly Thr Asn Trp Ser Val Glu
        290                 295                 300
Arg Ser Arg Leu Asn Tyr Pro Glu Asn Gly Trp Thr Pro Gly Glu Asp
305                 310                 315                 320
Ser Tyr Lys Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
            340                 345                 350
Tyr Tyr Val Lys Thr Tyr Arg Val Asp Ile Ser Ser Asn Gly Glu Asp
            355                 360                 365
Trp Ile Ser Leu Lys Glu Gly Asn Lys Ala Ile Ile Phe Gln Gly Asn
        370                 375                 380
Thr Asn Pro Thr Asp Val Val Leu Gly Val Phe Ser Lys Pro Leu Ile
385                 390                 395                 400
Thr Arg Phe Val Arg Ile Lys Pro Val Ser Trp Glu Thr Gly Ile Ser
            405                 410                 415
Met Arg Phe Glu Val Tyr Gly Cys Lys Ile Thr Asp Tyr Pro Cys Ser
            420                 425                 430
Gly Met Leu Gly Met Val Ser Gly Leu Ile Ser Asp Ser Gln Ile Thr
        435                 440                 445
Ala Ser Asn Gln Ala Asp Arg Asn Trp Met Pro Glu Asn Ile Arg Leu
        450                 455                 460
Val Thr Ser Arg Thr Gly Trp Ala Leu Pro Pro Ser Pro His Pro Tyr
465                 470                 475                 480
Thr Asn Glu Trp Leu Gln Val Asp Leu Gly Asp Glu Lys Ile Val Arg
                485                 490                 495
Gly Val Ile Ile Gln Gly Gly Lys His Arg Glu Asn Lys Val Phe Met
            500                 505                 510
Arg Lys Phe Lys Ile Ala Tyr Ser Asn Asn Gly Ser Asp Trp Lys Thr
        515                 520                 525
Ile Met Asp Asp Ser Lys Arg Lys Ala Lys Ser Phe Glu Gly Asn Asn
        530                 535                 540
Asn Tyr Asp Thr Pro Glu Leu Arg Thr Phe Pro Leu Ser Thr Arg
545                 550                 555                 560
Phe Ile Arg Ile Tyr Pro Glu Arg Ala Thr His Ser Gly Leu Gly Leu
                565                 570                 575
Arg Met Glu Leu Leu Gly Cys Glu Val Glu Ala Pro Thr Ala Gly Pro
```

```
                    580                 585                 590
Thr Thr Pro Asn Gly Asn Pro Val Asp Glu Cys Asp Asp Gln Ala
            595                 600                 605

Asn Cys His Ser Gly Thr Gly Asp Asp Phe Gln Leu Thr Gly Gly Thr
        610                 615                 620

Thr Val Leu Ala Thr Glu Lys Pro Thr Ile Ile Asp Ser Thr Ile Gln
625                 630                 635                 640

Ser Glu Phe Pro Thr Tyr Gly Phe Asn Cys Glu Phe Gly Trp Gly Ser
                645                 650                 655

His Lys Thr Phe Cys His Trp Glu His Asp Ser His Ala Gln Leu Arg
            660                 665                 670

Trp Ser Val Leu Thr Ser Lys Thr Gly Pro Ile Gln Asp His Thr Gly
        675                 680                 685

Asp Gly Asn Phe Ile Tyr Ser Gln Ala Asp Glu Asn Gln Lys Gly Lys
    690                 695                 700

Val Ala Arg Leu Val Ser Pro Val Val Tyr Ser Gln Ser Ser Ala His
705                 710                 715                 720

Cys Met Thr Phe Trp Tyr His Met Ser Gly Ser His Val Gly Thr Leu
                725                 730                 735

Arg Val Lys Leu Arg Tyr Gln Lys Pro Glu Glu Tyr Asp Gln Leu Val
            740                 745                 750

Trp Met Val Val Gly His Gln Gly Asp His Trp Lys Glu Gly Arg Val
        755                 760                 765

Leu Leu His Lys Ser Leu Lys Leu Tyr Gln Val Ile Phe Glu Gly Glu
    770                 775                 780

Ile Gly Lys Gly Asn Leu Gly Gly Ile Ala Val Asp Asp Ile Ser Ile
785                 790                 795                 800

Asn Asn His Ile Ser Gln Glu Asp Cys Ala Lys Pro Thr Asp Leu Asp
                805                 810                 815

Lys Lys Asn Thr Glu Ile Lys Ile Asp Glu Thr Gly Ser Thr Pro Gly
            820                 825                 830

Tyr Glu Gly Glu Gly Glu Gly Asp Lys Asn Ile Ser Arg Lys Pro Gly
        835                 840                 845

Asn Val Leu Lys Thr Leu Asp Pro Ile Leu Ile Thr Ile Ile Ala Met
    850                 855                 860

Ser Ala Leu Gly Val Leu Leu Gly Ala Val Cys Gly Val Val Leu Tyr
865                 870                 875                 880

Cys Ala Cys Trp His Asn Gly Met Ser Glu Arg Asn Leu Ser Ala Leu
                885                 890                 895

Glu Asn Tyr Asn Phe Glu Leu Val Asp Gly Val Lys Leu Lys Lys Asp
            900                 905                 910

Lys Leu Asn Pro Gln Ser Asn Tyr Ser Glu Ala
        915                 920

<210> SEQ ID NO 135
<211> LENGTH: 922
<212> TYPE: PRT
<213> ORGANISM: Rattus norvegicus

<400> SEQUENCE: 135

Met Glu Arg Gly Leu Pro Leu Leu Cys Ala Thr Leu Ala Leu Ala Leu
1               5                   10                  15

Ala Leu Ala Gly Ala Phe Arg Ser Asp Lys Cys Gly Gly Thr Ile Lys
                20                  25                  30
```

```
Ile Glu Asn Pro Gly Tyr Leu Thr Ser Pro Gly Tyr Pro His Ser Tyr
         35                  40                  45
His Pro Ser Glu Lys Cys Glu Trp Leu Ile Gln Ala Pro Glu Pro Tyr
 50                  55                  60
Gln Arg Ile Met Ile Asn Phe Asn Pro His Phe Asp Leu Glu Asp Arg
 65                  70                  75                  80
Asp Cys Lys Tyr Asp Tyr Val Glu Val Ile Asp Gly Glu Asn Glu Gly
                 85                  90                  95
Gly Arg Leu Trp Gly Lys Phe Cys Gly Lys Ile Ala Pro Ser Pro Val
                100                 105                 110
Val Ser Ser Gly Pro Phe Leu Phe Ile Lys Phe Val Ser Asp Tyr Glu
                115                 120                 125
Thr His Gly Ala Gly Phe Ser Ile Arg Tyr Glu Ile Phe Lys Arg Gly
         130                 135                 140
Pro Glu Cys Ser Gln Asn Tyr Thr Ala Pro Thr Gly Val Ile Lys Ser
145                 150                 155                 160
Pro Gly Phe Pro Glu Lys Tyr Pro Asn Ser Leu Glu Cys Thr Tyr Ile
                165                 170                 175
Ile Phe Ala Pro Lys Met Ser Glu Ile Ile Leu Glu Phe Glu Ser Phe
                180                 185                 190
Asp Leu Glu Gln Asp Ser Asn Pro Pro Gly Gly Val Phe Cys Arg Tyr
         195                 200                 205
Asp Arg Leu Glu Ile Trp Asp Gly Phe Pro Glu Val Gly Pro His Ile
         210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Ile Ser Glu Asp
                260                 265                 270
Phe Lys Cys Met Glu Ala Leu Gly Met Glu Ser Gly Glu Ile His Ser
         275                 280                 285
Asp Gln Ile Thr Ala Ser Ser Gln Tyr Gly Thr Asn Trp Ser Val Glu
         290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
         340                 345                 350
Tyr Tyr Val Lys Thr Tyr Arg Val Asp Ile Ser Ser Asn Gly Glu Asp
         355                 360                 365
Trp Ile Thr Leu Lys Glu Gly Asn Lys Ala Ile Ile Phe Gln Gly Asn
370                 375                 380
Thr Asn Pro Thr Asp Val Val Phe Gly Val Phe Pro Lys Pro Leu Ile
385                 390                 395                 400
Thr Arg Phe Val Arg Ile Lys Pro Ala Ser Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
         435                 440                 445
Ala Ser Asn Gln Gly Asp Arg Asn Trp Met Pro Glu Asn Ile Arg Leu
```

```
                450              455              460
Val Thr Ser Arg Thr Gly Trp Ala Leu Pro Ser Pro His Pro Tyr
465              470              475              480

Ile Asn Glu Trp Leu Gln Val Asp Leu Gly Asp Glu Lys Ile Val Arg
                485              490              495

Gly Val Ile Ile Gln Gly Lys His Arg Glu Asn Lys Val Phe Met
                500              505              510

Arg Lys Phe Lys Ile Ala Tyr Ser Asn Asn Gly Ser Asp Trp Lys Met
        515              520              525

Ile Met Asp Asp Ser Lys Arg Lys Ala Lys Ser Phe Glu Gly Asn Asn
        530              535              540

Asn Tyr Asp Thr Pro Glu Leu Arg Ala Phe Thr Pro Leu Ser Thr Arg
545              550              555              560

Phe Ile Arg Ile Tyr Pro Glu Arg Ala Thr His Ser Gly Leu Gly Leu
                565              570              575

Arg Met Glu Leu Leu Gly Cys Glu Val Glu Val Pro Thr Ala Gly Pro
                580              585              590

Thr Thr Pro Asn Gly Asn Pro Val Asp Glu Cys Asp Asp Gln Ala
                595              600              605

Asn Cys His Ser Gly Thr Gly Asp Asp Phe Gln Leu Thr Gly Gly Thr
        610              615              620

Thr Val Leu Ala Thr Glu Lys Pro Thr Ile Ile Asp Ser Thr Ile Gln
625              630              635              640

Ser Glu Phe Pro Thr Tyr Gly Phe Asn Cys Glu Phe Gly Trp Gly Ser
                645              650              655

His Lys Thr Phe Cys His Trp Glu His Asp Ser His Ala Gln Leu Arg
                660              665              670

Trp Arg Val Leu Thr Ser Lys Thr Gly Pro Ile Gln Asp His Thr Gly
        675              680              685

Asp Gly Asn Phe Ile Tyr Ser Gln Ala Asp Glu Asn Gln Lys Gly Lys
        690              695              700

Val Ala Arg Leu Val Ser Pro Val Val Tyr Ser Gln Ser Ser Ala His
705              710              715              720

Cys Met Thr Phe Trp Tyr His Met Ser Gly Ser His Val Gly Thr Leu
                725              730              735

Arg Val Lys Leu His Tyr Gln Lys Pro Glu Glu Tyr Asp Gln Leu Val
                740              745              750

Trp Met Val Val Gly His Gln Gly Asp His Trp Lys Glu Gly Arg Val
        755              760              765

Leu Leu His Lys Ser Leu Lys Leu Tyr Gln Val Ile Phe Glu Gly Glu
770              775              780

Ile Gly Lys Gly Asn Leu Gly Ile Ala Val Asp Asp Ile Ser Ile
785              790              795              800

Asn Asn His Ile Pro Gln Glu Asp Cys Ala Lys Pro Thr Asp Leu Asp
                805              810              815

Lys Lys Asn Thr Glu Ile Lys Ile Asp Glu Thr Gly Ser Thr Pro Gly
                820              825              830

Tyr Glu Glu Gly Lys Gly Asp Lys Asn Ile Ser Arg Lys Pro Gly Asn
        835              840              845

Val Leu Lys Thr Leu Asp Pro Ile Leu Ile Thr Ile Ala Met Ser
850              855              860

Ala Leu Gly Val Leu Leu Gly Ala Val Cys Gly Val Val Leu Tyr Cys
865              870              875              880
```

-continued

```
Ala Cys Trp His Asn Gly Met Ser Glu Arg Asn Leu Ser Ala Leu Glu
            885                 890                 895

Asn Tyr Asn Phe Glu Leu Val Asp Gly Val Lys Leu Lys Lys Asp Lys
        900                 905                 910

Leu Asn Pro Gln Ser Asn Tyr Ser Glu Ala
        915                 920

<210> SEQ ID NO 136
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Ala"
<220> FEATURE:
<221> NAME/KEY: VARIANT
<222> LOCATION: (8)..(8)
<223> OTHER INFORMATION: /replace="Ala"
<220> FEATURE:
<221> NAME/KEY: VARIANT
<222> LOCATION: (16)..(16)
<223> OTHER INFORMATION: /replace="Glu"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 136

Ile Ile Ser Gly Ser Gly Gly Ser Thr Tyr Tyr Ala Asp Ser Val Lys
1               5                   10                  15

Gly

<210> SEQ ID NO 137
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (4)..(4)
<223> OTHER INFORMATION: /replace="Lys" or "Ser"
<220> FEATURE:
<221> NAME/KEY: VARIANT
<222> LOCATION: (6)..(6)
<223> OTHER INFORMATION: /replace="Val"
<220> FEATURE:
<221> NAME/KEY: MISC_FEATURE
<222> LOCATION: (1)..(9)
<223> OTHER INFORMATION: /note="Variant residues given in the sequence
      have no preference with respect to those in the annotations
      for variant positions"

<400> SEQUENCE: 137

Phe Thr Phe Ala Ser Tyr Ala Met Val
1               5

<210> SEQ ID NO 138
<211> LENGTH: 13
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (13)..(13)
<223> OTHER INFORMATION: /replace="Val"
<220> FEATURE:
<221> NAME/KEY: MISC_FEATURE
<222> LOCATION: (1)..(13)
<223> OTHER INFORMATION: /note="Variant residues given in the sequence
      have no preference with respect to those in the annotations
      for variant positions"

<400> SEQUENCE: 138

Ala Arg Asp Leu Gly Tyr Tyr Gly Ser Gly Met His Ala
1               5                   10

<210> SEQ ID NO 139
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (13)..(13)
<223> OTHER INFORMATION: /replace="Asn"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"

<400> SEQUENCE: 139

Ala Arg Asp Arg Gly Met Tyr Tyr Ala Ser Gly Phe Gly Pro
1               5                   10

<210> SEQ ID NO 140
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Gly Gly Gly Gly Ser
1               5

<210> SEQ ID NO 141
<211> LENGTH: 453
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
```

```
                35                  40                  45
Ser Gln Ile Ser Pro Ala Gly Gly Tyr Thr Asn Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Glu Leu Pro Tyr Tyr Arg Met Ser Lys Val Met Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450
```

<210> SEQ ID NO 142
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 142

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 143
<211> LENGTH: 923
<212> TYPE: PRT
<213> ORGANISM: Homo sapiens

<400> SEQUENCE: 143

```
Met Glu Arg Gly Leu Pro Leu Leu Cys Ala Val Leu Ala Leu Val Leu
1               5                   10                  15

Ala Pro Ala Gly Ala Phe Arg Asn Asp Lys Cys Gly Asp Thr Ile Lys
            20                  25                  30

Ile Glu Ser Pro Gly Tyr Leu Thr Ser Pro Gly Tyr Pro His Ser Tyr
        35                  40                  45

His Pro Ser Glu Lys Cys Glu Trp Leu Ile Gln Ala Pro Asp Pro Tyr
    50                  55                  60

Gln Arg Ile Met Ile Asn Phe Asn Pro His Phe Asp Leu Glu Asp Arg
65                  70                  75                  80

Asp Cys Lys Tyr Asp Tyr Val Glu Val Phe Asp Gly Glu Asn Glu Asn
```

```
                    85                  90                  95
Gly His Phe Arg Gly Lys Phe Cys Gly Lys Ile Ala Pro Pro Val
                100                 105                 110
Val Ser Ser Gly Pro Phe Leu Phe Ile Lys Phe Val Ser Asp Tyr Glu
                115                 120                 125
Thr His Gly Ala Gly Phe Ser Ile Arg Tyr Glu Ile Phe Lys Arg Gly
                130                 135                 140
Pro Glu Cys Ser Gln Asn Tyr Thr Thr Pro Ser Gly Val Ile Lys Ser
145                 150                 155                 160
Pro Gly Phe Pro Glu Lys Tyr Pro Asn Ser Leu Glu Cys Thr Tyr Ile
                165                 170                 175
Val Phe Val Pro Lys Met Ser Glu Ile Ile Leu Glu Phe Glu Ser Phe
                180                 185                 190
Asp Leu Glu Pro Asp Ser Asn Pro Pro Gly Met Phe Cys Arg Tyr
                195                 200                 205
Asp Arg Leu Glu Ile Trp Asp Gly Phe Pro Asp Val Gly Pro His Ile
                210                 215                 220
Gly Arg Tyr Cys Gly Gln Lys Thr Pro Gly Arg Ile Arg Ser Ser Ser
225                 230                 235                 240
Gly Ile Leu Ser Met Val Phe Tyr Thr Asp Ser Ala Ile Ala Lys Glu
                245                 250                 255
Gly Phe Ser Ala Asn Tyr Ser Val Leu Gln Ser Ser Val Ser Glu Asp
                260                 265                 270
Phe Lys Cys Met Glu Ala Leu Gly Met Glu Ser Gly Glu Ile His Ser
                275                 280                 285
Asp Gln Ile Thr Ala Ser Ser Gln Tyr Ser Thr Asn Trp Ser Ala Glu
                290                 295                 300
Arg Ser Arg Leu Asn Tyr Pro Glu Asn Gly Trp Thr Pro Gly Glu Asp
305                 310                 315                 320
Ser Tyr Arg Glu Trp Ile Gln Val Asp Leu Gly Leu Leu Arg Phe Val
                325                 330                 335
Thr Ala Val Gly Thr Gln Gly Ala Ile Ser Lys Glu Thr Lys Lys Lys
                340                 345                 350
Tyr Tyr Val Lys Thr Tyr Lys Ile Asp Val Ser Ser Asn Gly Glu Asp
                355                 360                 365
Trp Ile Thr Ile Lys Glu Gly Asn Lys Pro Val Leu Phe Gln Gly Asn
                370                 375                 380
Thr Asn Pro Thr Asp Val Val Ala Val Phe Pro Lys Pro Leu Ile
385                 390                 395                 400
Thr Arg Phe Val Arg Ile Lys Pro Ala Thr Trp Glu Thr Gly Ile Ser
                405                 410                 415
Met Arg Phe Glu Val Tyr Gly Cys Lys Ile Thr Asp Tyr Pro Cys Ser
                420                 425                 430
Gly Met Leu Gly Met Val Ser Gly Leu Ile Ser Asp Ser Gln Ile Thr
                435                 440                 445
Ser Ser Asn Gln Gly Asp Arg Asn Trp Met Pro Glu Asn Ile Arg Leu
450                 455                 460
Val Thr Ser Arg Ser Gly Trp Ala Leu Pro Pro Ala Pro His Ser Tyr
465                 470                 475                 480
Ile Asn Glu Trp Leu Gln Ile Asp Leu Gly Glu Glu Lys Ile Val Arg
                485                 490                 495
Gly Ile Ile Ile Gln Gly Gly Lys His Arg Glu Asn Lys Val Phe Met
                500                 505                 510
```

```
Arg Lys Phe Lys Ile Gly Tyr Ser Asn Asn Gly Ser Asp Trp Lys Met
            515                 520                 525
Ile Met Asp Asp Ser Lys Arg Lys Ala Lys Ser Phe Glu Gly Asn Asn
530                 535                 540
Asn Tyr Asp Thr Pro Glu Leu Arg Thr Phe Pro Ala Leu Ser Thr Arg
545                 550                 555                 560
Phe Ile Arg Ile Tyr Pro Glu Arg Ala Thr His Gly Gly Leu Gly Leu
                565                 570                 575
Arg Met Glu Leu Leu Gly Cys Glu Val Glu Ala Pro Thr Ala Gly Pro
            580                 585                 590
Thr Thr Pro Asn Gly Asn Leu Val Asp Glu Cys Asp Asp Gln Ala
            595                 600                 605
Asn Cys His Ser Gly Thr Gly Asp Asp Phe Gln Leu Thr Gly Gly Thr
            610                 615                 620
Thr Val Leu Ala Thr Glu Lys Pro Thr Val Ile Asp Ser Thr Ile Gln
625                 630                 635                 640
Ser Glu Phe Pro Thr Tyr Gly Phe Asn Cys Glu Phe Gly Trp Gly Ser
                645                 650                 655
His Lys Thr Phe Cys His Trp Glu His Asp Asn His Val Gln Leu Lys
            660                 665                 670
Trp Ser Val Leu Thr Ser Lys Thr Gly Pro Ile Gln Asp His Thr Gly
            675                 680                 685
Asp Gly Asn Phe Ile Tyr Ser Gln Ala Asp Glu Asn Gln Lys Gly Lys
            690                 695                 700
Val Ala Arg Leu Val Ser Pro Val Val Tyr Ser Gln Asn Ser Ala His
705                 710                 715                 720
Cys Met Thr Phe Trp Tyr His Met Ser Gly Ser His Val Gly Thr Leu
                725                 730                 735
Arg Val Lys Leu Arg Tyr Gln Lys Pro Glu Glu Tyr Asp Gln Leu Val
            740                 745                 750
Trp Met Ala Ile Gly His Gln Gly Asp His Trp Lys Glu Gly Arg Val
            755                 760                 765
Leu Leu His Lys Ser Leu Lys Leu Tyr Gln Val Ile Phe Glu Gly Glu
            770                 775                 780
Ile Gly Lys Gly Asn Leu Gly Gly Ile Ala Val Asp Asp Ile Ser Ile
785                 790                 795                 800
Asn Asn His Ile Ser Gln Glu Asp Cys Ala Lys Pro Ala Asp Leu Asp
                805                 810                 815
Lys Lys Asn Pro Glu Ile Lys Ile Asp Glu Thr Gly Ser Thr Pro Gly
            820                 825                 830
Tyr Glu Gly Glu Gly Glu Gly Asp Lys Asn Ile Ser Arg Lys Pro Gly
            835                 840                 845
Asn Val Leu Lys Thr Leu Asp Pro Ile Leu Ile Thr Ile Ala Met
850                 855                 860
Ser Ala Leu Gly Val Leu Gly Ala Val Cys Gly Val Val Leu Tyr
865                 870                 875                 880
Cys Ala Cys Trp His Asn Gly Met Ser Glu Arg Asn Leu Ser Ala Leu
                885                 890                 895
Glu Asn Tyr Asn Phe Glu Leu Val Asp Gly Val Lys Leu Lys Lys Asp
                900                 905                 910
Lys Leu Asn Thr Gln Ser Thr Tyr Ser Glu Ala
            915                 920
```

<210> SEQ ID NO 144
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Trp Ala Tyr Leu Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 145
<211> LENGTH: 454
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Gly Tyr
            20                  25                  30

Gly Ile His Trp Val Arg Gln Ala Pro Gly Lys Gly Leu Glu Trp Val
        35                  40                  45

Ala Tyr Ile Tyr Pro Asp Ser Gly Tyr Thr Asp Tyr Ala Asp Ser Val
    50                  55                  60

Lys Gly Arg Phe Thr Ile Ser Ala Asp Thr Ser Lys Asn Thr Ala Tyr

```
            65                  70                  75                  80
Leu Gln Met Asn Ser Leu Arg Ala Glu Asp Thr Ala Val Tyr Tyr Cys
                    85                  90                  95
Ala Arg Glu Asp Phe Arg Asn Arg Arg Leu Trp Tyr Val Met Asp
                100                 105                 110
Tyr Trp Gly Gln Gly Thr Leu Val Thr Val Ser Ser Ala Ser Thr Lys
                115                 120                 125
Gly Pro Ser Val Phe Pro Leu Ala Pro Ser Ser Lys Ser Thr Ser Gly
        130                 135                 140
Gly Thr Ala Ala Leu Gly Cys Leu Val Lys Asp Tyr Phe Pro Glu Pro
145                 150                 155                 160
Val Thr Val Ser Trp Asn Ser Gly Ala Leu Thr Ser Gly Val His Thr
                165                 170                 175
Phe Pro Ala Val Leu Gln Ser Ser Gly Leu Tyr Ser Leu Ser Ser Val
                180                 185                 190
Val Thr Val Pro Ser Ser Ser Leu Gly Thr Gln Thr Tyr Ile Cys Asn
                195                 200                 205
Val Asn His Lys Pro Ser Asn Thr Lys Val Asp Lys Lys Val Glu Pro
        210                 215                 220
Lys Ser Cys Asp Lys Thr His Thr Cys Pro Pro Cys Pro Ala Pro Glu
225                 230                 235                 240
Leu Leu Gly Gly Pro Ser Val Phe Leu Phe Pro Pro Lys Pro Lys Asp
                245                 250                 255
Thr Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp Gly
                275                 280                 285
Val Glu Val His Asn Ala Lys Thr Lys Pro Arg Glu Glu Gln Tyr Asn
        290                 295                 300
Ser Thr Tyr Arg Val Val Ser Val Leu Thr Val Leu His Gln Asp Trp
305                 310                 315                 320
Leu Asn Gly Lys Glu Tyr Lys Cys Lys Val Ser Asn Lys Ala Leu Pro
                325                 330                 335
Ala Pro Ile Glu Lys Thr Ile Ser Lys Ala Lys Gly Gln Pro Arg Glu
                340                 345                 350
Pro Gln Val Tyr Thr Leu Pro Pro Ser Arg Glu Glu Met Thr Lys Asn
                355                 360                 365
Gln Val Ser Leu Thr Cys Leu Val Lys Gly Phe Tyr Pro Ser Asp Ile
        370                 375                 380
Ala Val Glu Trp Glu Ser Asn Gly Gln Pro Glu Asn Asn Tyr Lys Thr
385                 390                 395                 400
Thr Pro Pro Val Leu Asp Ser Asp Gly Ser Phe Phe Leu Tyr Ser Lys
                405                 410                 415
Leu Thr Val Asp Lys Ser Arg Trp Gln Gln Gly Asn Val Phe Ser Cys
                420                 425                 430
Ser Val Met His Glu Ala Leu His Asn His Tyr Thr Gln Lys Ser Leu
                435                 440                 445
Ser Leu Ser Pro Gly Lys
        450

<210> SEQ ID NO 146
<211> LENGTH: 15
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 146

Trp Tyr Gln Gln Lys Pro Gly Gln Ala Pro Arg Leu Leu Ile Tyr
1               5                   10                  15

<210> SEQ ID NO 147
<211> LENGTH: 4
<212> TYPE: PRT
<213> ORGANISM: Homo sapiens

<400> SEQUENCE: 147

Glu Leu Leu Gly
1

<210> SEQ ID NO 148
<211> LENGTH: 4
<212> TYPE: PRT
<213> ORGANISM: Homo sapiens

<400> SEQUENCE: 148

Glu Phe Leu Gly
1
```